US008592408B2

(12) United States Patent
Hall et al.

(10) Patent No.: US 8,592,408 B2
(45) Date of Patent: Nov. 26, 2013

(54) FUSED AMINODIHYDROTHIAZINE DERIVATIVES

(71) Applicant: Eisai R&D Management Co., Ltd., Tokyo (JP)

(72) Inventors: Adrian Hall, Hatfield (GB); Christopher Neil Farthing, Hatfield (GB)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 13/685,109

(22) Filed: Nov. 26, 2012

(65) Prior Publication Data
US 2013/0203740 A1 Aug. 8, 2013

Related U.S. Application Data

(63) Continuation of application No. 13/354,716, filed on Jan. 20, 2012, now Pat. No. 8,338,407.

(30) Foreign Application Priority Data

Jan. 21, 2011 (GB) .................................. 1101140.0

(51) Int. Cl.
C07D 513/04 (2006.01)
A61K 31/542 (2006.01)

(52) U.S. Cl.
USPC .......................................... 514/224.2; 544/48

(58) Field of Classification Search
USPC .......................................... 544/48; 514/224.2
See application file for complete search history.

(56) References Cited

U.S. PATENT DOCUMENTS

| 3,227,713 | A | 1/1966 | Behner et al. |
| 3,235,551 | A | 2/1966 | Schubert et al. |
| 7,189,715 | B2 | 3/2007 | Jerussi et al. |
| 7,648,983 | B2 | 1/2010 | Audia et al. |
| 8,158,620 | B2 | 4/2012 | Suzuki et al. |
| 8,198,269 | B2 | 6/2012 | Motoki et al. |
| 8,338,407 | B2 | 12/2012 | Hall et al. |
| 8,426,584 | B2 | 4/2013 | Mitasev et al. |
| 8,501,733 | B2 | 8/2013 | Motoki et al. |
| 2004/0110743 | A1 | 6/2004 | Miyamato et al. |
| 2006/0052406 | A1 | 3/2006 | Fisher et al. |
| 2006/0111370 | A1 | 5/2006 | Zhu et al. |
| 2007/0021454 | A1 | 1/2007 | Coburn et al. |
| 2007/0287692 | A1 | 12/2007 | Wu et al. |
| 2008/0139538 | A1 | 6/2008 | McGaughey et al. |
| 2008/0200445 | A1 | 8/2008 | Zhu et al. |
| 2009/0082560 | A1 | 3/2009 | Kobayashi et al. |
| 2009/0209755 | A1 | 8/2009 | Suzuki et al. |
| 2010/0075957 | A1 | 3/2010 | Tamura et al. |
| 2010/0093999 | A1 | 4/2010 | Motoki et al. |
| 2010/0160290 | A1 | 6/2010 | Kobayashi et al. |
| 2010/0317850 | A1 | 12/2010 | Suzuki et al. |
| 2011/0009395 | A1 | 1/2011 | Audia et al. |
| 2011/0152253 | A1 | 6/2011 | Motoki et al. |
| 2011/0207723 | A1 | 8/2011 | Motoki et al. |
| 2012/0094984 | A1 | 4/2012 | Suzuki et al. |
| 2012/0190672 | A1 | 7/2012 | Hall et al. |
| 2012/0190848 | A1 | 7/2012 | Mitasev et al. |
| 2012/0202804 | A1 | 8/2012 | Ellard et al. |
| 2012/0202828 | A1 | 8/2012 | Castro Pineiro et al. |
| 2013/0197244 | A1 | 8/2013 | Mitasev et al. |

FOREIGN PATENT DOCUMENTS

| EP | 1 942 105 | 7/2008 |
| EP | 2 233 474 | 9/2010 |
| JP | 09-067355 | 3/1997 |
| JP | 2004-149429 | 5/2004 |
| WO | WO 01/87293 | 11/2001 |
| WO | WO 02/096897 | 12/2002 |
| WO | WO 2004/014843 | 2/2004 |
| WO | WO 2004/043916 | 5/2004 |
| WO | WO 2005/058311 | 6/2005 |

(Continued)

OTHER PUBLICATIONS

Ames et al., "Methods for detecting carcinogens and mutagens with the Salmonella/mammalian-microsome mutagenicity test," *Mutat. Res.*, 31:347-364 (1975).

(Continued)

*Primary Examiner* — Kahsay Habte
(74) *Attorney, Agent, or Firm* — Fish & Richardson P.C.

(57) ABSTRACT

The present invention relates to a fused aminodihydrothiazine derivative of formula (I):

wherein
X is hydrogen or fluorine;
A is CH or N;
Y is methyl, ethyl, monofluoromethyl, difluoromethyl, trifluoromethyl, difluoroethyl, methoxy, ethoxy, methoxymethyl or —C≡N;
and pharmaceutically acceptable salts thereof;
which compound has an Aβ production inhibitory effect or a BACE1 inhibitory effect and is useful as a prophylactic or therapeutic agent for a neurodegenerative disease caused by Aβ and typified by Alzheimer-type dementia.

4 Claims, 1 Drawing Sheet

(56) References Cited

FOREIGN PATENT DOCUMENTS

| | | |
|---|---|---|
| WO | WO 2005/097767 | 10/2005 |
| WO | WO 2006/041404 | 4/2006 |
| WO | WO 2006/041405 | 4/2006 |
| WO | WO 2006/059234 | 6/2006 |
| WO | WO 2006/138264 | 12/2006 |
| WO | WO 2007/011810 | 1/2007 |
| WO | WO 2007/049532 | 5/2007 |
| WO | WO 2007/114771 | 10/2007 |
| WO | WO 2007/139230 | 12/2007 |
| WO | WO 2008/073365 | 6/2008 |
| WO | WO 2008/133273 | 11/2008 |
| WO | WO 2008/133274 | 11/2008 |
| WO | WO 2009/067081 | 5/2009 |
| WO | WO 2009/091016 | 7/2009 |
| WO | WO 2010/013302 | 2/2010 |
| WO | WO 2010/013794 | 2/2010 |
| WO | WO 2010/038686 | 4/2010 |
| WO | WO 2011/005738 | 1/2011 |
| WO | WO 2011/009897 | 1/2011 |
| WO | WO 2011/009898 | 1/2011 |
| WO | WO 2012/003274 | 1/2012 |
| WO | WO 2012/093148 | 7/2012 |
| WO | WO 2012/098461 | 7/2012 |
| WO | WO 2012/100179 | 7/2012 |

OTHER PUBLICATIONS

Arnone et al., An Enantiospecific Entry to Fluoro Substituted Aminocyclopentanols through Intramolecular Nitrile Oxide, Nitrone, and Oxime Cycloaddition Reactions, *Tetrahedron: Asymmetry* 5(6):1019-1028 (1994).
Aschwanden et al., "Reduction of 2,3-dihydroisoxazoles to beta-amino ketones and beta-amino alcohols," *Org. Lett.*, 7(25):5741-5742 (2005).
Berge et al., "Pharmaceutical salts," *J. Pharm. Sci.*, 66:1-19 (1977).
Bobrov et al., "Interaction of Quinone Oxide with Thiourea" *Chemistry and Chemical Technology*, 33(10):15-18 (1990) (original and English language translation).
Brzostwska et al., "Chiral Prodyes: Synthesis and Full Characterization of (S)-1-Phenylethylamides of the Optically Active Q-Methyldihydrofluoresceins," *Heterocycles*, 32(10):1968-1972 (1991).
Chakrabarty et al., "DBU, a highly efficient reagent for the facile regeneration of (hetero)arylamines from their acetamides and benzamides: influence of solvent, temperature, and microwave irradiation," *Synth. Commun.*, 32(2):265-272 (2002).
Cohen et al., "Synthesis of 2-Amino-5,6-dihydro-4H-1,3-thiazines and Related Compounds by Acid Catalyzed Cyclization of Allylic Isothiuronium Salts," *Journal of Heterocyclic Chemistry*, 14:717-723 (1977).
Cross et al., International Union of Pure and Applied Chemistry (IUPAC) Rules for the Nomenclature of Organic Chemistry, Section E, Stereochemistry, *Pure & Applied Chemistry*, 45:11-30 (1976).
Forman et al., "Differential Effects of the Swedish Mutant Amyloid Precursor Protein on β-Amyloid Accumulation and Secretion in Neurons and Nonneuronal Cells," *The Journal of Biological Chemistry*, 272(51):32247-32253 (1997).
Glenner et al., "Alzheimer's Disease: Initial report of the purification and characterization of a novel cerebrovascular amyloid protein," *Biochemical and Biophysical Research Communications*, 120(3):885-890 (1984).
Gloor et al., "Molecular and cellular permeability control at the blood-brain barrier," *Brain Res. Rev.*, 36:258-264 (2001).
Gong et al., "Alzheimer's disease-affected brain: Presence of oligomeric Aβ ligands (ADDLs) suggests a molecular basis for reversible memory loss," *Proceeding National Academy of Science USA*, 100(18):10417-10422 (2003).
Gouras et al., "Intraneuronal Aβ42 Accumulation in Human Brain," *American Journal of Pathology*, 156(1):15-20 (2000).

Green et al., "Mutagen testing using TRP+ reversion in *Escherichia coli*," *Mutat. Res.*, 38:3-32 (1976).
Greene et al., "Protective Groups in Organic Chemistry, Third Edition," *John Wiley & Sons*, 404-408 (1999).
Greene et al., "Protective Groups in Organic Chemistry, Third Edition," *John Wiley & Sons*, 518-525 (1999).
He et al., "Utility of unbound plasma drug levels and P-glycoprotein transport data in prediction of central nervous system exposure," *Xenobiotica*, 39:687-693 (2009).
Heany et al., "The influence of oxime stereochemistry in the generation of nitrones from omega-alkenyloximes by cyclization or 1,2-prototropy," *J Chem. Soc., Perkin Trans.*, 1:341-349 (Jan. 1, 1998).
Hitchcock et al., "Structure-brain exposure relationships," *J. Med. Chem.*, 49:7559-7583 (2006).
Hock et al., "Antibodies against β-Amyloid Slow Cognitive Decline in Alzheimer's Disease," *Neuron*, 38:547-554 (2003).
Howbert et al., "Novel agents effective against solid tumors: The diarylsulfonylureas. Synthesis, activities, and analysis of quantitative structure-activity relationships," *J Med. Chem.*, 33:2393-2407 (1990).
Hussain et al., "Oral administration of a potent and selective non-peptidic BACE—1 inhibitor decreases beta-cleavage of amyloid precursor protein and amyloid-beta production in vivo," *J. Neurochem.*, 100:802-809 (2007).
Iserloh et al., "Discovery of an orally efficaceous 4-phenoxypyrrolidine-based BACE-1 inhibitor," *Bioorg. Med. Chem. Lett.*, 18:418-422 (2008).
Ishikawa et al., "Synthesis of A-Ring Fragments of $1\alpha,25$-Dihydroxyvitamin $D_3$ and Taxane Diterpenoids: Effective Construction of Conjugated Formylcyclohexene Frameworks from Isoxazolines," *Tetrahedron*, 54(22):5869-5882 (1998).
Jarrett et al., "The Carboxy Terminus of the α Amyloid Protein is Critical for the Seeding of Amyloid Formation: Implications for the Pathogenesis of Alzheimer's Disease," *Biochemistry*, 32(18):4693-4697 (1993).
Kalvass et al., "Influence of nonspecific brain and plasma binding on CNS exposure: implications for rational drug discovery," *Biopharm. Drug Dispos.*, 23:327-338 (2002).
Katagiri et al., "Synthesis of Chiral Spiro 3-Oxazolin-5-one 3-Oxides (Chiral Nitrones) via a Nitrosoketene Intermediate and Their Asymmetric 1,3-Dipolar Cycloaddition Reactions Leading to the EPC Synthesis of Modified Amino Acids," *Tetrahedron*, 53(16):5725-5746 (1997).
Khimiya i Khimicheskaya Tekhologiya, 33(10):15-18 (1990).
Kuo et al., "A Synthesis of Estrone via Novel Intermediates, Mechanism of the Coupling Reaction of a Vinyl Carbinol with a 13 Diketone," *Journal of Organic Chemistry*, 33(8):3126-3132 (1968).
Kusuhara et al., "Efflux transport systems for drugs at the blood-brain barrier and blood-cerebrospinal fluid barrier (Part 1)," *Drug Discov. Today*, 6:150-156 (2001).
Lin et al., "Role of P-glycoprotein in pharmacokinetics: clinical implications," *Clin. Pharmacokinet.*, 42:59-98 (2003).
Lin, "How significant is the role of P-glycoprotein in drug absorption and brain uptake?," *Drugs of Today*, 40:5-22 (2004).
Liu et al., "A practical and chemoselective reduction of nitroarenes to anilines using activated iron," *Adv. Synth. Caral.*, 347:217-219 (2005).
Mahar et al., "Passive permeability and P-glycoprotein-mediated efflux differentiate central nervous system (CNS) and non-CNS marketed drugs," *J. Pharmacol. Exp. Ther.*, 303:1029-1037 (2002).
Malamas et al., "Design and synthesis of aminohydantoins as potent and selective human β-secretase (BACE1) inhibitors with enhanced brain permeability," *Bioorg. Med. Chem. Lett.*, 20:6597-6605 (2010).
Masters et al., "Amyloid plaque core protein in Alzheimer disease and Down syndrome," *Proceeding National Academy of Science USA*, 82:4245-4249 (1985).
Maurer, "Relationship between exposure and nonspecific binding of thirty-three central nervous system drugs in mice," *Drug Metab. Dispos.*, 33:175-181 (2005).
McCann et al., "Detection of carcinogens as mutagens in the Salmonella/microsome test: assay of 300 chemicals," *Proc. Natl. Acad. Sci. USA.*, 72:5135-5139 (1975).

(56) References Cited

OTHER PUBLICATIONS

McCann et al., "Detection of carcinogens as mutagens in the Salmonella/microsome test: assay of 300 chemicals: discussion," *Proc. Natl. Acad. Sci. USA*, 73:950-954 (1976).
Meredith et al., "P-glycoprotein efflux and other factors limit brain amyloid α reduction by β-site amyloid precursor protein-cleaving enzyme 1 inhibitors in mice," *J Pharmacol. Exp. Ther.*, 326:502-513 (2008).
Nahm et al., N-Methoxy-N-Methylamides as Effective Acylating Agents, *Tetrahedron Lett.*, 22(39):3815-3818 (1981).
Prakash et al., "Perfluoroalkylation with Organosilicon Reagents," *Chem. Rev.*, 97:757-786 (1997).
Romero et al., "Discovery, synthesis, and bioactivity of bis(heteroaryl)piperazines. 1. A novel class of non-nucleoside HIV-1 reverse transcriptase inhibitors," *J Med. Chem.*, 37(7):999-1014 (1994).
Rosowsky et al., "Synthesis and biological activity of the 2-desamino and 2-desamino-2-methyl analogues of aminopterin and methotrexate," *J Med. Chem.*, 34(1):227-234 (1991).
Sankaranarayanan et al., "In Vivo β-Secretase 1 Inhibition Leads to Brain AβLowering and Increased β-Secretase Processing of Amyloid Precursor Protein without Effect on Neuregulin-1," *J. Pharmacol. Exp. Ther*, 324(3):957-969 (2008).
Sankaranarayanan et al., "First demonstration of cerebrospinal fluid and plasma A beta lowering with oral administration of a beta-site amyloid precursor protein-cleaving enzyme 1 inhibitor in nonhuman primates," *J Pharmacol. Exp. Ther.*, 328:131-140 (2009).
Scheuner et al., "Secreted amyloid β-protein similar to that in the senile plaques of Alzheimer's disease is increased in vivo by the presenilin 1 and 2 and APP mutations linked to familial Alzheimer's disease," *Nature Medicine*, 2(8):864-870 (1996).
Schinkel, "P-Glycoprotein, a gatekeeper in the blood-brain barrier," *Adv. Drug Deliv. Rev.*, 36:179-194 (1999).
Shing et al., "Intramolecular nitrile oxide-alkene cycloaddition of sugar derivatives with unmasked hydroxyl group(s)," *Org. Lett.*, 9(5):753-756 (2007).
Summerfield et al., "Central nervous system drug disposition: The relationship between in situ brain permeability and brain free fraction," *J. Pharmacol. Exp. Ther.*, 322:205-213 (2007).
Trainor, "The importance of plasma protein binding in drug discovery," *Expert Opin. Drug Discov.*, 2:51-64 (2007).
Tzvetkov et al., Synthesis and photoinitiated radical cyclization of allyl- and propynyloxymethyl substituted cyclopentanones to tetrahydrocyclopenta[c]furanols, *Tetrahedron Lett.*, 46(45):7751-7755 (2005).
Ueno, "Molecular anatomy of the brain endothelial barrier: An overview of the distributional features," *Curr. Med. Chem.*, 14:1199-1206 (2007).
Uno et al., "Reaction of 2-Isoxazolines with Organolithiums in the Presence of Boron Trifluoride," *Bull. Chem. Soc. Jpn.*, 66:2730-2737 (1993).
Whisler et al., "Synthetic applications of lithiated N-Boc allylic amines as asymmetric homoenolate equivalents," *J. Org. Chem.*, 68:1207-1215 (2003).
International Search Report for App. Ser. No. PCT/EP2012/050833, mailed Apr. 18, 2012, 9 pages.
Acceptance of Complete Specification from South African Application No. 2010/04799 (Aug. 16, 2011).
Amended Claims and Specification Filed with Response to Office Action from Chilean Application No. 96-2009 and English Translation (Nov. 4, 2011).
Amendment and Response to Office Action from Mexican Application No. MX/a/2010/007337 and English Translation (Jan. 3, 2012).
Amendment and Response to Office Action from Singapore Application No. 201102027-8 (Dec. 28, 2011).
Argument and Amendment in Response to Office Action from Japanese Application No. 2009-550050 and English Translation (Apr. 12, 2010).
Argument and Amendment in Response to Office Action from New Zealand Application No. 586796 (Apr. 28, 2011).
Argument and Amendment in Response to Office Action from Pakistan Application No. 43/2009 (May 21, 2010).
Decision of Granting Patent from Japanese Application No. 2009-550050 and English Translation (May 7, 2010).
Decision of Grant dated Feb. 23, 2012 for Ukraine App. Ser. No. a201010101 and English Translation.
English Translation of Office Action from Mexican Application No. MX/a/2010/007337 (2011).
Examination Report from Australian App. Ser. No. 2009205072, dated Jul. 19, 2012.
Examination Report from Chilean App. Ser. No. 702-2-011, dated May 14, 2012 and English Translation.
Examination Report and Notice of Acceptance of Complete Specification from New Zealand Application No. 586796 (Oct. 6, 2011).
Extended Search Report from European Application No. 09701914.5 (Sep. 30, 2011).
European Search Report for App. Ser. No. EP 09 81 7719, dated Feb. 14, 2012.
International Preliminary Report on Patentability from PCT Application No. PCT/JP2009/050511 (Aug. 31, 2010).
International Search Report from PCT Application No. PCT/JP2009/050511 (Mar. 24, 2009).
Newspaper Publication of Venezuelan Application No. 2009-000078 (2011).
Notice of Acceptance for New Zealand App. Ser. No. 591878, dated May 17, 2012.
Office Action from Canadian App. Ser. No. 2,711,655, dated Jun. 5, 2012.
Office Action from Chilean Application No. 96/2009 and English Translation (2011).
Office Action from Chilean Application No. 96/2009 and English Translation (Aug. 1, 2011).
Office Action from Chilean Application No. 96/2009 and English Translation (Dec. 12, 2011).
Office Action from Chinese Application No. 200980101688.X and English Translation (Apr. 1, 2012).
Office Action from Japanese Application No. 2009-550050 and English translation (Feb. 9, 2011).
Office Action from Mexican Application No. MX/a/2010/007337 and English Translation (Oct. 19, 2011).
Office Action from New Zealand Application No. 586796 (Feb. 21, 2011).
Office Action from Pakistan Application No. 35/2012 (2012).
Office Action from Pakistan Application No. 43/2009 (Mar. 26, 2010).
Office Action from Russian App. Ser. No. 2010134403, dated May 14, 2012 and English Translation.
Official Acceptance Notice for Pakistan Application No. 43/2009 (Jun. 10, 2010).
Response to Office Action from Chilean Application No. 96/2009 and English Translation (Nov. 4, 2011).
Response to Office Action from Chilean Application No. 96/2009 and English Translation (Mar. 22, 2012).
Response to Office Action from Chinese Application No. 200980101688.X and English Translation (Jun. 15, 2012).
Restriction Requirement from U.S. Appl. No. 12/355,154 (Apr. 19, 2011).
Response to Restriction Requirement from U.S. Appl. No. 12/355,154 (May 19, 2011).
Office Action from U.S. Appl. No. 12/355,154 (Jun. 3, 2011).
Amendment in Reply to Office Action of Jun. 3, 2011 in U.S. Appl. No. 12/355,154 (Sep. 2, 2011).
Supplemental Amendment in Reply to Office Action of Jun. 3, 2011 in U.S. Appl. No. 12/355,154 (Sep. 27, 2011).
Notice of Allowance from U.S. Appl. No. 12/355,154 (Oct. 5, 2011).
Amendment filed with Request for Continued Examination from U.S. Appl. No. 12/355,154 (Jan. 5, 2012).
Notice of Allowance from U.S. Appl. No. 12/355,154 (Jan. 18, 2012).
Notice of Allowance from U.S. Appl. No. 12/355,154 (Feb. 17, 2012).
Written Opinion from Singapore Application No. 201102027-8 (Aug. 24, 2011).

(56) References Cited

OTHER PUBLICATIONS

Written Opinion from Singapore Application No. 201102027-8 (Mar. 15, 2012).
Office Action from U.S. Application No. 12/568,151 (Oct. 24, 2011).
Amendment and Response to Office Action from U.S. Appl. No. 12/568,151 (Dec. 22, 2011).
Notice of Allowance from U.S. Appl. No. 12/568,151 (Jan. 4, 2012).
Office Action from U.S. Appl. U.S. Appl. No. 13/333,238, dated Jun. 18, 2012.
Office Action from Mexican Application No. MX/a/2011/003189 and English Translation (Jun. 25, 2012).
Response to Written Opinion from Singapore Application No. 201102027-8 (Jul. 5, 2012).
Abdel-Magid et al., "Reductive Amination of Aldehydes and Ketones with Sodium Triacetoxyborohydride. Studies on Direct and Indirect Reductive Amination Procedures," *J. Org. Chem.*, 61(11):3849-3862 (1996).
Aranyos et al., "Novel Electron-Rich Bulky Phosphine Ligands Facilitate the Palladium-Catalyzed Preparation of Diaryl Ethers," *J Am Chem Soc.*, 121(18):4369-4378 (1999).
Barange et al., "A Remarkable Accelerating Effect of Ag-Salt on Intramolecular Cyclization of o-(1-Alkynyl)benzenesulfonamides," *J. Org. Chem.*, 72(22):8547-8550 (2007).
Barlow et al., "Intervalence Transitions in the Mixed-Valence Monocations of Bis(triarylamines) Linked with Vinylene and Phenylene—Vinylene Bridges," *J. Am. Chem. Soc.*, 127(48):16900-16911 (2005).
Butler et al., "A Facile Synthesis of New 5H-Indazolo[3,2-b]benzo[d]-1,3-oxazines via One-Pot Intramolecular Bis-heterocyclizations," *J. Org. Chem.*, 73(1):234-240 (2008).
Coates et al., "Annelative ring expansion via intramolecular [2 + 2] photocycloaddition of .alpha.,.beta.-unsaturated .gamma.-lactones and reductive cleavage: synthesis of hydrocyclopentacyclooctene-5-carboxylates," *J Org. Chem.*, 47(19):3597-3607 (1982).
Crisp and Meyer, "Palladium-catalyzed, carbonylative, intramolecular coupling of hydroxyvinyl triflates. Synthesis of substituted .alpha.,.beta.-butenolides,"*J. Org. Chem.*, 57(25):6972-6975 (1992).
Danheiser et al., "An annulation method for the synthesis of highly substituted polycyclic aromatic and heteroaromatic compounds," *J Am. Chem. Soc.*, 112(8):3093-3100 (1990).
De Lucca et al., "Discovery and Structure—Activity Relationship of N-(Ureidoalkyl)-Benzyl-Piperidines As Potent Small Molecule CC Chemokine Receptor-3 (CCR3) Antagonists," *J Med. Chem.*, 45(17)3794-3804 (2002).
Edwards et al., "Application of Fragment-Based Lead Generation to the Discovery of Novel, Cyclic Amidine β-Secretase Inhibitors with Nanomolar Potency, Cellular Activity, and High Ligand Efficiency," *J. Med. Chem.*, 50(24):5912-5925 (2007).
Fang et al., "Synthesis, Antibacterial, and Cytotoxic Evaluation of Certain 7-Substituted Norfloxacin Derivatives," *J. Med. Chem.*, 43(20):3809-3812 (2000).
Fuller et al., "Succinct Synthesis of β-Amino Acids via Chiral Isoxazolin," *J. Am. Chem. Soc.*, 127(15):5376-5383 (2005).
Fuller et al., "Synthesis and Structural Characteristics of Geminally Disubstituted β-Amino Acids," *SYNLETT.*, 8:1409-1413 (2004).
Fulop et al., "Synthesis of Stereoisomers 2-Phenylimino-3, 1-Perhydro-Benzoxazines and 3, 1-Perhydrobenzothiazines," *Org Prep Proced Int'l*, 20:73-82 (1988).
Greene and Wuts, "Protective Groups in Organic Chemistry, Second Edition", *John Wiley & Sons* p. 327-330 (1991).
Greene and Wuts, "Protective Groups in Organic Chemistry, Third Edition", *John Wiley & Sons*, p. 17-245 (1999).
Greene and Wuts, "Protective Groups in Organic Chemistry, Third Edition", *John Wiley & Sons*, p. 293-329 (1999).
Greene and Wuts, "Protective Groups in Organic Chemistry, Third Edition", *John Wiley & Sons*, p. 494-572 (1999).
Greene and Wuts, "Protective Groups in Organic Chemistry, Third Edition", *John Wiley & Sons*, p. 531-537 (1999).
Greene and Wuts, "Protective Groups in Organic Chemistry, Third Edition", *John Wiley & Sons*, p. 642-643 (1999).
Greene and Wuts, "Protective Groups in Organic Chemistry, Third Edition", *John Wiley & Sons*, p. 506-507 (1999).
Gu et al., "Facile One-Pot Synthesis of 6-Monosubstituted and 6,12-Disubstituted 5,11-Dihydroindolo[3,2-b]carbazoles and Preparation of Various Functionalized Derivatives," *J. Org. Chem.*, 72(19):7207-7213 (2007).
Hall et al., "Comparative pharmacokinetic-pharmacodynamic responses in rat and cynomolgus monkey for a novel BACE inhibitor ER-901356," $11^{th\ Int'l\ Conf\ on\ Alzheimer's}$ & *Parkinson's Diseases (AD/PD 2013)*, 4 pages, (Mar. 6-10, 2013).
Han et al., "Diverse Synthesis of Novel Bisterpyridines via Suzuki-Type Cross-Coupling," *Org. Lett.*, 9(4):559-562 (2007).
Hassner et al. "Stereochemistry. 82. Conformation of fused five-membered heterocyclic rings derived from the intramolecular oxime olefin cycloaddition reaction," *J. Org. Chem.*, 58(17):4539-4546 (1993).
Hassner, "Interamolecular Oxime Olefin Cycloadditions. Stereospecific Formation of Functionalized Pyrrolidines," *Tetrahedron Letters*, 29 (41):5313-5316 (1988).
Iwata et al., "Radiosynthesis of O-[$^{11}$C]methyl-L-tyrosine and O-[$^{18}$F]Fluoromethyl-L-tyrosine as potential PET tracers for imaging amino acid transport," *J Labelled Compounds & Radiopharmaceuticals*, 46(6):555-566 (2003).
Ji et al., "Synthesis and Structure—Activity Relationship Studies of 3,6-Diazabicyclo[3.2.0]heptanes as Novel α4β2 Nicotinic Acetylcholine Receptor Selective Agonists," *J Med. Chem.*, 50(22):5493-5508 (2007).
Kearney et al., "Solid-Phase Synthesis of 2-Aminothiazoles," *J Org. Chem.*, 63(1):196-200 (1998).
Knauer and Kunz, "Palladium-catalysed C-C coupling reactions in the enantioselective synthesis of 2,4-disubstituted 4,5-dehydropiperidines using galactosylamine as a stereodifferentiating auxiliary," *Tetrahedron: Asymmetry*, 16(2):529-539 (2005).
Kwong et al., "Copper-Catalyzed Coupling of Alkylamines and Aryl Iodides: An Efficient System Even in an Air Atmosphere," *Org. Lett.*, 4(4):581-584 (2002).
Leroux et al., "Trifluoromethoxy Substituted Anilines: Metalation as the Key Step for Structural Elaboration," *J. Org. Chem.*, 68(12):4693-4699 (2003).
Littke et al., "Versatile Catalysts for the Suzuki Cross-Coupling of Arylboronic Acids with Aryl and Vinyl Halides and Triflates under Mild Conditions," *J. Am. Chem. Soc.*, 122(17):4020-4028 (2000).
Matassa et al., "Synthesis and in vitro LTD4 antagonist activity of bicyclic and monocyclic cyclopentylurethane and cyclopentylacetamide N-arylsulfonyl amides," *J Med. Chem.*, 33(9):2621-2629 (1990).
Nerdinger et al., "Combined Directed ortho Metalation/Suzuki—Miyaura Cross-Coupling Strategies. Regiospecific Synthesis of Chlorodihydroxybiphenyls and Polychlorinated Biphenyls," *J. Org. Chem.*, 72(16):5960-5967 (2007).
Nussbaumer et al., "Highly selective TFAA-cleavage of tertiary 2,4-dimethoxybenzylamines and its use in the synthesis of secondary amines," *Tetrahedron*, 47(26):4591-4602 (1991).
Quach and Batey, "Ligand- and Base-Free Copper(II)-Catalyzed C-N. Bond Formation: Cross-Coupling Reactions of Organoboron Compounds with Aliphatic Amines and Anilines," *Org. Lett.*, 5(23):4397-4400 (2003).
Rao et al., "Improved Synthesis of Mirtazapine," *Org. Prep. Proced. Int.*, 39(4):399-402 (2007).
Rolandsgard et al., "Stereoselective preparation of spirane bridged, sandwiched bisarenes," *Tetrahedron*, 61(16):4128-4140 (2005).
Sapountzis et al., "Synthesis of Functionalized Nitroarylmagnesium Halides via an Iodine—Magnesium Exchange," *J. Org. Chem.*, 70(7):2445-2454 (2005).
Schwizer et al., "Antagonists of the myelin-associated glycoprotein: A new class of tetrasaccharide mimics," *Bioorg. Med. Chem.*, 14:4944-4957 (2006).
Selles and Mueller, "Expedient Synthesis of Highly Substituted Fused Heterocoumarins," *Org. Lett.*, 6(2):277-279 (2004).

(56) References Cited

OTHER PUBLICATIONS

Shao et al., "4-(2-Pyridyl)piperazine-1-benzimidazoles as potent TRPV1 antagonists," *Bioorg. Med. Chem. Lett.*, 15(3):719-723 (2005).

Tamayo et al., 'Design and synthesis of potent pyridazine inhibitors of p38 MAP kinase, *Bioorg. Med. Chem. Lett.*,15(9):2409-2413 (2005).

Tao et al., "Copper-catalyzed synthesis of aryl azides and 1-aryl-1,2,3-triazoles from boronic acids," *Tetrahedron Lett.*, 48:3525-3529 (2007).

Tzschucke et al., "Arenes to Anilines and Aryl Ethers by Sequential Iridium-Catalyzed Borylation and Copper-Catalyzed Coupling," *Org. Lett.*, 9(5):761-764 (2007).

Vedejs et al., "Enantiocontrolled Synthesis of (1S,2S)-6-Desmethyl-(methylaziridino)mitosene," *J. Am. Chem. Soc.*, 122(22):5401-5402 (2000).

Vedejs et al., "Synthetic Enantiopure Aziridinomitosenes: Preparation, Reactivity, and DNA Alkylation Studies," *J. Am. Chem. Soc.*, 125(51):15796-15806 (2003).

Watanabe et al., "A convenient method for the synthesis of $\Delta,6$-bicyclo[4.n.0]alken-2-ones," *Tetrahedron Lett.*, 40(46):8133-8136 (1999).

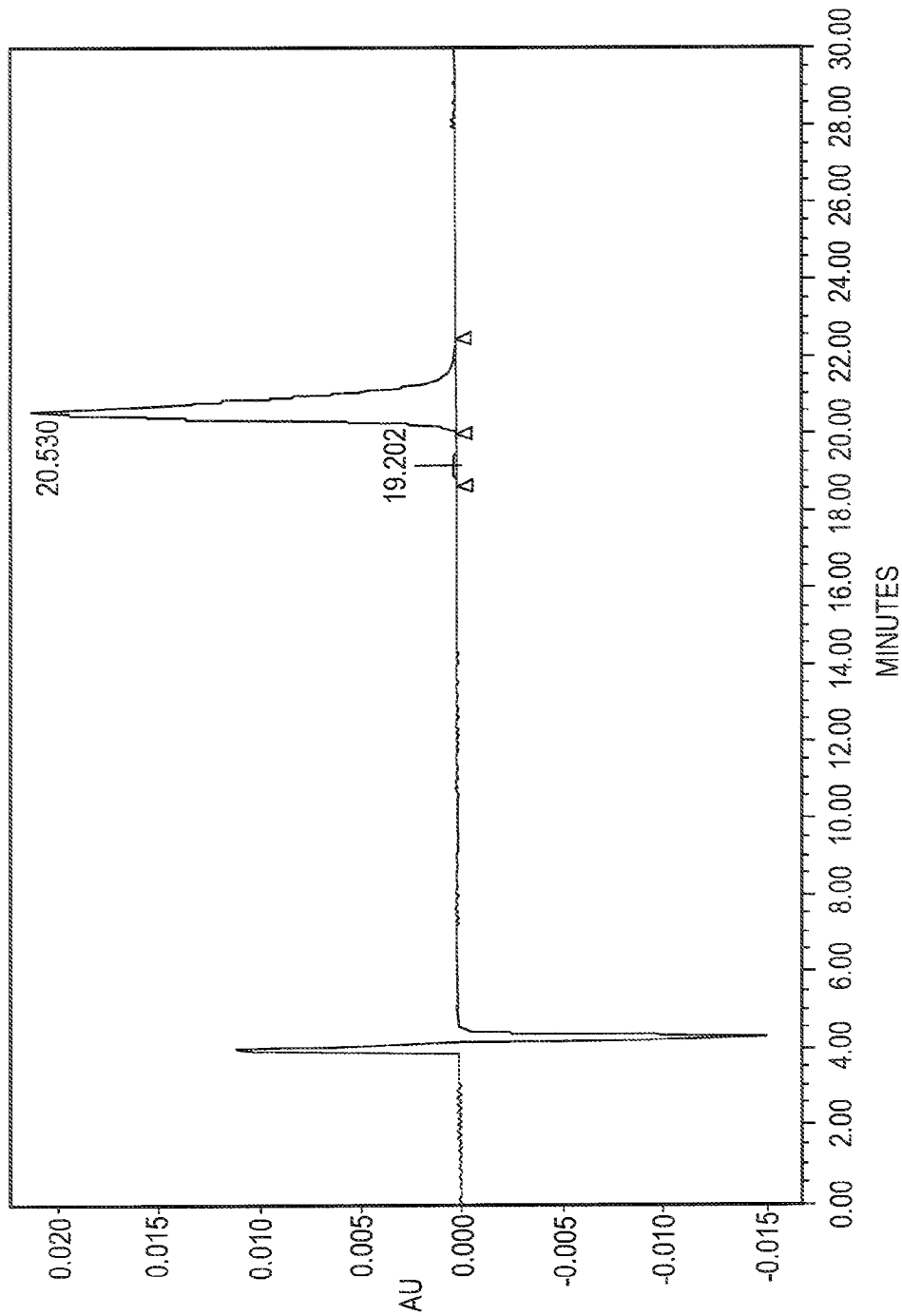

FUSED AMINODIHYDROTHIAZINE DERIVATIVES

CROSS REFERENCE TO RELATED APPLICATIONS

This application is a continuation of U.S. application Ser. No. 13/354,716, filed on Jan. 20, 2012, which issued as U.S. Pat. No. 8,338,407 on Dec. 25, 2012, which claims the benefit of priority of British application serial number 1101140.0, filed Jan. 21, 2011. The disclosure of the prior application is considered part of (and is incorporated by reference in) the disclosure of this application.

The present invention relates to a fused aminodihydrothiazine derivative and pharmaceutical use thereof. More particularly, the present invention relates to a fused aminodihydrothiazine derivative which has an amyloid-β (hereinafter referred to as Aβ protein production inhibitory effect or a beta-site amyloid-β precursor protein cleavage enzyme 1 (hereinafter referred to as BACE1 or beta-secretase) inhibitory effect and is effective for treating a neurodegenerative disease caused by Aβ protein, in particular, Alzheimer-type dementia, Down's syndrome or the like, and to a pharmaceutical composition comprising the fused aminodihydrothiazine derivative as an active ingredient.

Alzheimer's disease is a disease characterized by degeneration and loss of neurons as well as formation of senile plaques and neurofibrillary tangles. Currently, only the symptoms of Alzheimer's disease are treated using a symptom-improving agent typified by an acetylcholinesterase inhibitor, and a fundamental remedy to inhibit progression of the disease has not yet been developed. It is necessary to develop a method for controlling the cause of the onset of pathology in order to create a fundamental remedy for Alzheimer's disease.

It is assumed that Aβ-proteins as breakdown products of amyloid precursor proteins (hereinafter referred to as APP) are highly involved in degeneration and loss of neurons and onset of symptoms of dementia. Aβ-proteins have, as main components, Aβ40 consisting of 40 amino acids and Aβ42 with two amino acids added at the C-terminal. The Aβ40 and Aβ42 are known to be highly prone to aggregation and to be the main components of senile plaques. Further, it is known that the Aβ40 and Aβ42 are increased by mutations in APP and presenilin genes which is observed in familial Alzheimer's disease. Accordingly, a compound that reduces production of Aβ40 and Aβ42 is expected to be a disease progression inhibitor or prophylactic agent for Alzheimer's disease.

Aβ is produced by the cleavage of APP by beta-secretase (BACE1) and subsequently by gamma-secretase. For this reason, attempts have been made to create gamma-secretase and beta-secretase inhibitors in order to inhibit Aβ production.

Published International patent application WO2011/005738 (Eli Lilly and Company) describes compounds of formula (A) and their use as BACE inhibitors:

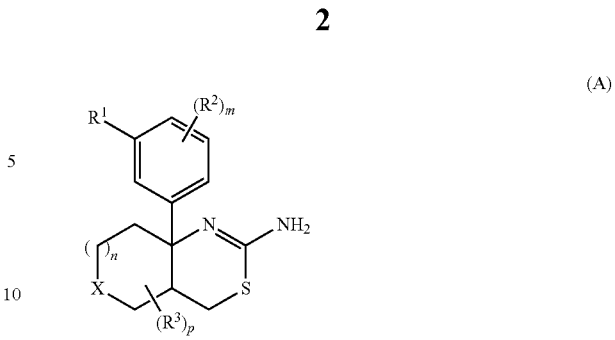

where $R^1$, $R^2$, $R^3$, X, m, n and p are defined therein.

Fused aminodihydrothiazine compounds of formula (B) have already been disclosed in published International patent application WO2009/091016 (Eisai R&D Management Co., Ltd.):

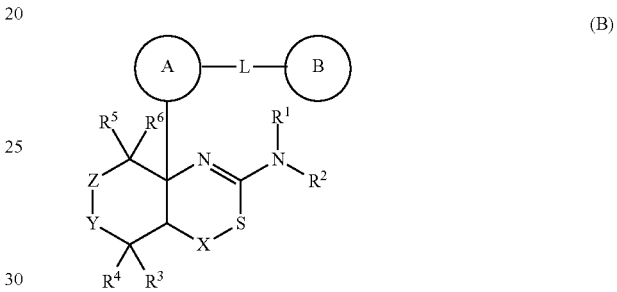

wherein ring A represents a $C_{6-14}$aryl group or the like; L represents —$NR^eCO$— [wherein $R^e$ represents a hydrogen atom or the like] or the like; ring B represents a $C_{6-14}$aryl group or the like; X represents a $C_{1-3}$alkylene group or the like; Y represents a single bond or the like; Z represents a $C_{1-3}$alkylene group or the like; $R^1$ and $R^2$ independently represent a hydrogen atom or the like; and $R^3$, $R^4$, $R^5$ and $R^6$ independently represent a hydrogen atom, a halogen atom or the like.

Further fused aminodihydrothiazine compounds of formula (C) have been disclosed in published International patent application WO2010/038686 (Eisai R&D Management Co., Ltd.):

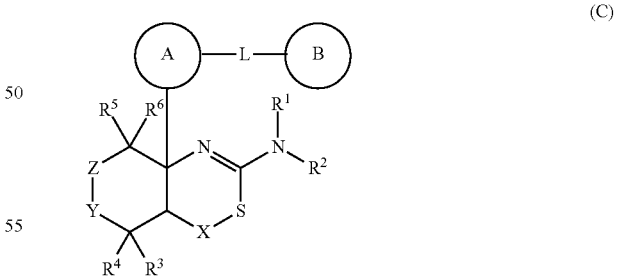

wherein ring A represents a $C_{6-14}$aryl group or the like; L represents —$NR^eCO$—[wherein $R^e$ represents a hydrogen atom or the like] or the like; the ring B represents a $C_{6-14}$aryl group or the like; X represents a $C_{1-3}$alkylene group or the like; Y represents a single bond or the like; Z represents an oxygen atom or the like; $R^1$ and $R^2$ each independently represent a hydrogen atom or the like; and $R^3$, $R^4$, $R^5$ and $R^6$ each independently represents a hydrogen atom, a halogen atom or the like.

The present invention represents a selection from the genus of compounds disclosed in WO2009/091016.

An object of the present invention is to provide further compounds that have an Aβ production inhibitory effect or a BACE1 inhibitory effect and are useful as prophylactic or therapeutic agents for a neurodegenerative disease caused by Aβ and typified by Alzheimer-type dementia, which compounds are fused aminodihydrothiazine derivatives.

Thus, the present invention provides the compound of formula (I):

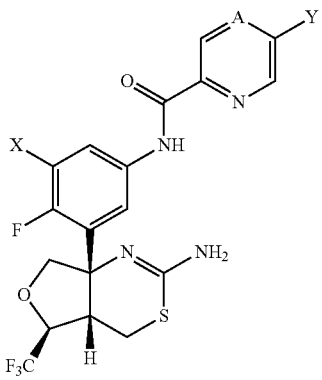

(I)

wherein
X is hydrogen or fluorine;
A is CH or N;
Y is methyl, ethyl, monofluoromethyl, difluoromethyl, trifluoromethyl, difluoroethyl, methoxy, ethoxy, methoxymethyl or —C≡N;
and pharmaceutically acceptable salts thereof.

In one embodiment of the present invention, X is hydrogen.
In another embodiment of the present invention, A is N.
In another embodiment of the present invention, Y is methyl, monofluoromethyl, difluoromethyl, trifluoromethyl or methoxy.

One favoured group of compounds of the present invention is the compound of formula (Ia) and pharmaceutically acceptable salts thereof:

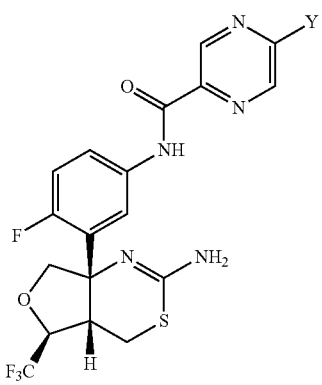

(Ia)

where Y is as hereinbefore defined. Preferably, Y is methyl, monofluoromethyl, difluoromethyl, trifluoromethyl, difluoroethyl, methoxy, ethoxy or methoxymethyl.

In one embodiment the present invention provides a compound of formula (Ia) wherein Y is methoxy or monofluoromethyl.

Another favoured group of compounds of the present invention is the compound of formula (Ib) and pharmaceutically acceptable salts thereof:

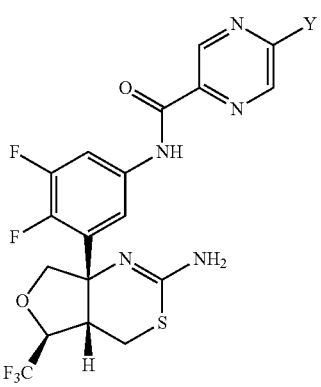

(Ib)

where Y is as hereinbefore defined. Preferably, Y is methyl, monofluoromethyl, difluoromethyl or methoxy.

A further favoured group of compounds of the present invention is the compound of formula (Ic) and pharmaceutically acceptable salts thereof:

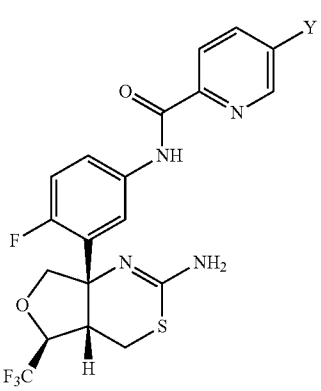

(Ic)

where Y is as hereinbefore defined. Preferably, Y is methyl, ethyl, trifluoromethyl, methoxy or —C≡N.

Preferred compounds of the present invention are:
N-(3-((4aS,5S,7aS)-2-amino-5-(trifluoromethyl)-4a,5,7,7a-tetrahydro-4H-furo[3,4-d][1,3]thiazin-7a-yl)-4-fluorophenyl)-5-methoxypyrazine-2-carboxamide:

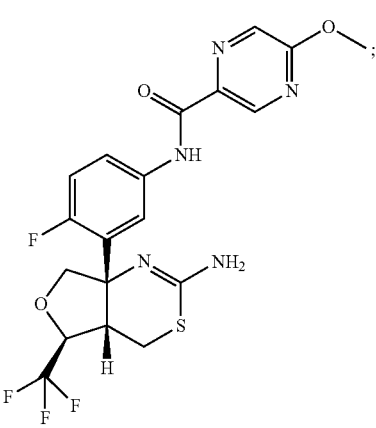 [SMILES: COc1cnc(C(=O)Nc2ccc(F)c([C@]34CO[C@H](C(F)(F)F)[C@H]3CSC(N)=N4)c2)cn1]

N-(3-((4aS,5S,7aS)-2-amino-5-(trifluoromethyl)-4a,5,7,7a-tetrahydro-4H-furo[3,4-d][1,3]thiazin-7a-yl)-4-fluorophenyl)-5-cyanopicolinamide:

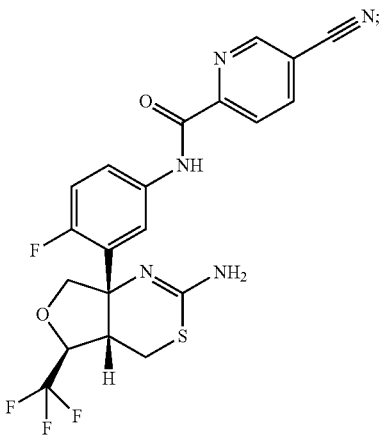 [SMILES: N#Cc1ccc(C(=O)Nc2ccc(F)c([C@]34CO[C@H](C(F)(F)F)[C@H]3CSC(N)=N4)c2)nc1]

N-(3-((4aS,5S,7aS)-2-amino-5-(trifluoromethyl)-4a,5,7,7a-tetrahydro-4H-furo[3,4-d][1,3]thiazin-7a-yl)-4-fluorophenyl)-5-methylpyrazine-2-carboxamide:

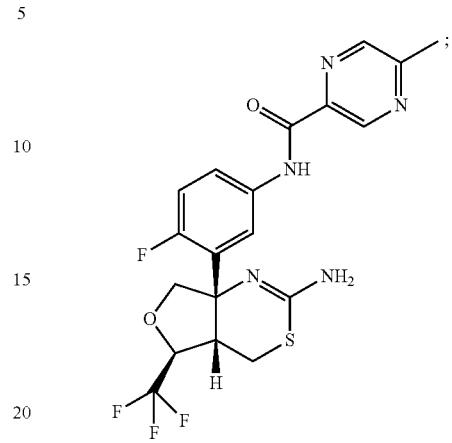

N-(3-((4aS,5S,7aS)-2-amino-5-(trifluoromethyl)-4a,5,7,7a-tetrahydro-4H-furo[3,4-d][1,3]thiazin-7a-yl)-4-fluorophenyl)-5-(difluoromethyl)pyrazine-2-carboxamide:

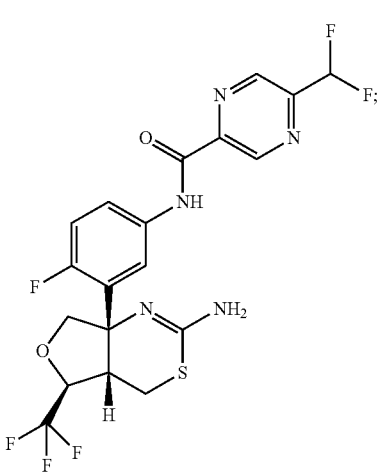 [SMILES: NC1=N[C@@]2(c3cc(NC(=O)c4cnc(C(F)F)cn4)ccc3F)CO[C@H](C(F)(F)F)[C@H]2CS1]

N-(3-((4aS,5S,7aS)-2-amino-5-(trifluoromethyl)-4a,5,7,7a-tetrahydro-4H-furo[3,4-d][1,3]thiazin-7a-yl)-4-fluorophenyl)-5-methylpicolinamide:

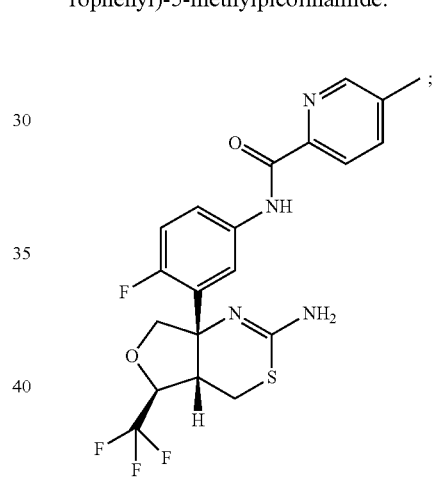

N-(3-((4aS,5S,7aS)-2-amino-5-(trifluoromethyl)-4a,5,7,7a-tetrahydro-4H-furo[3,4-d][1,3]thiazin-7a-yl)-4-fluorophenyl)-5-(trifluoromethyl)picolinamide:

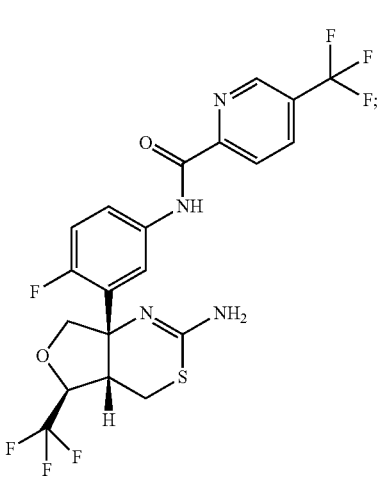 [SMILES: NC1=N[C@@]2(c3cc(NC(=O)c4ccc(C(F)(F)F)cn4)ccc3F)CO[C@H](C(F)(F)F)[C@H]2CS1]

N-(3-((4aS,5S,7aS)-2-amino-5-(trifluoromethyl)-4a,5,7,7a-tetrahydro-4H-furo[3,4-d][1,3]thiazin-7a-yl)-4-fluorophenyl)-5-ethylpicolinamide:

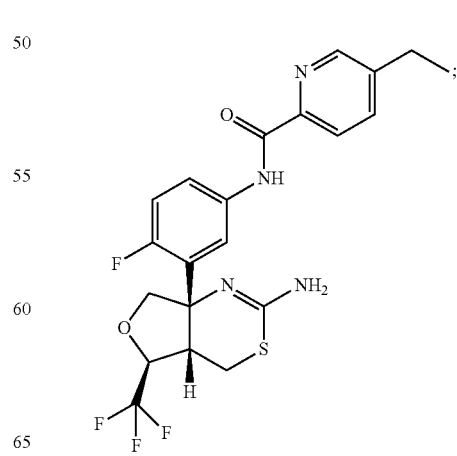

7

N-(3-((4aS,5S,7aS)-2-amino-5-(trifluoromethyl)-4a,5,7,7a-tetrahydro-4H-furo[3,4-d][1,3]thiazin-7a-yl)-4-fluorophenyl)-5-(fluoromethyl)pyrazine-2-carboxamide:

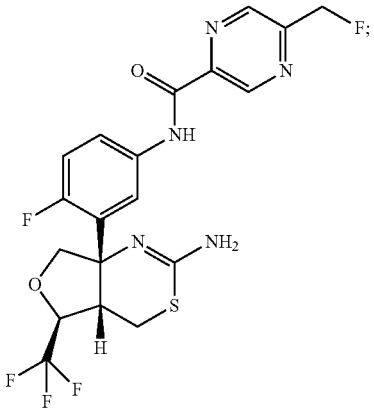 [SMILES: NC1=N[C@@]2(c3cc(NC(=O)c4cnc(CF)cn4)ccc3F)CO[C@H](C(F)(F)F)[C@H]2CS1]

N-(3-((4aS,5S,7aS)-2-amino-5-(trifluoromethyl)-4a,5,7,7a-tetrahydro-4H-furo[3,4-d][1,3]thiazin-7a-yl)-4-fluorophenyl)-5-methoxypicolinamide:

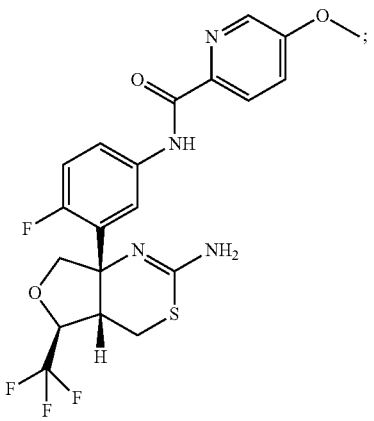 [SMILES: COc1ccc(C(=O)Nc2ccc(F)c([C@]34CO[C@H](C(F)(F)F)[C@H]3CSC(N)=N4)c2)nc1]

N-(3-((4aS,5S,7aS)-2-amino-5-(trifluoromethyl)-4a,5,7,7a-tetrahydro-4H-furo[3,4-d][1,3]thiazin-7a-yl)-4-fluorophenyl)-5-ethoxypyrazine-2-carboxamide:

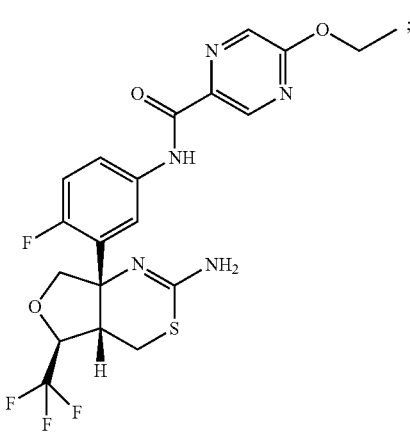 [SMILES: CCOc1cnc(C(=O)Nc2ccc(F)c([C@]34CO[C@H](C(F)(F)F)[C@H]3CSC(N)=N4)c2)cn1]

8

N-(3-((4aS,5S,7aS)-2-amino-5-(trifluoromethyl)-4a,5,7,7a-tetrahydro-4H-furo[3,4-d][1,3]thiazin-7a-yl)-4-fluorophenyl)-5-(1,1-difluoroethyl)pyrazine-2-carboxamide:

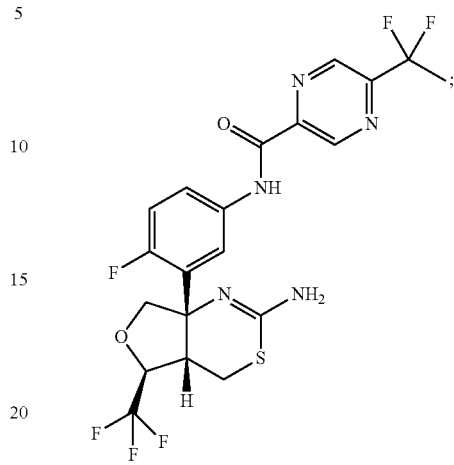

N-(3-((4aS,5S,7aS)-2-amino-5-(trifluoromethyl)-4a,5,7,7a-tetrahydro-4H-furo[3,4-d][1,3]thiazin-7a-yl)-4-fluorophenyl)-5-(trifluoromethyl)pyrazine-2-carboxamide:

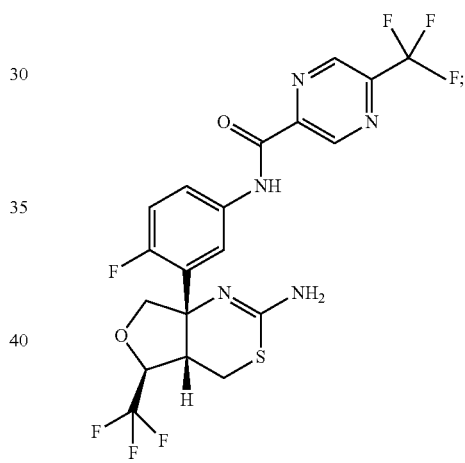

N-(3-((4aS,5S,7aS)-2-amino-5-(trifluoromethyl)-4a,5,7,7a-tetrahydro-4H-furo[3,4-d][1,3]thiazin-7a-yl)-4-fluorophenyl)-5-(methoxymethyl)pyrazine-2-carboxamide:

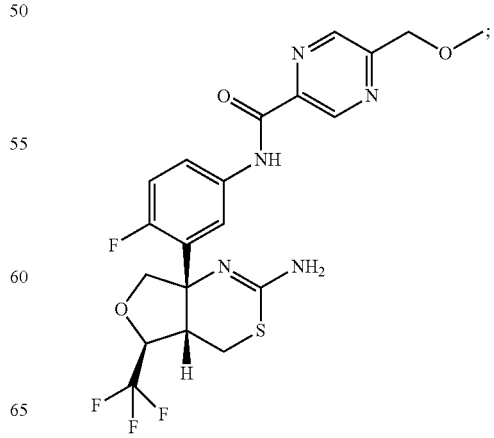

N-{3-[(4aS,5S,7aS)-2-amino-5-(trifluoromethyl)-4a,5-dihydro-4H-furo[3,4 d][1,3]thiazin-7a(7H)-yl]-4-fluorophenyl}-5-[($^2$H$_3$)methyloxy]pyrazine-2-carboxamide:

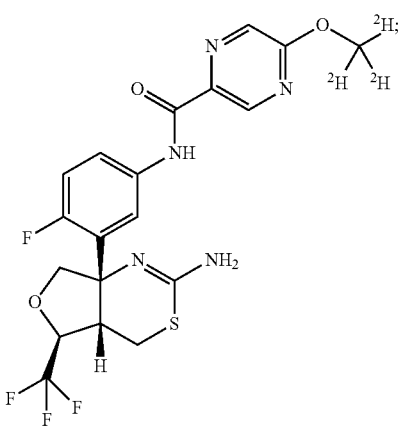

N-(3-((4aS,5S,7aS)-2-amino-5-(trifluoromethyl)-4a,5,7,7a-tetrahydro-4H-furo[3,4-d][1,3]thiazin-7a-yl)-4,5-difluorophenyl)-5-(difluoromethyl)pyrazine-2-carboxamide:

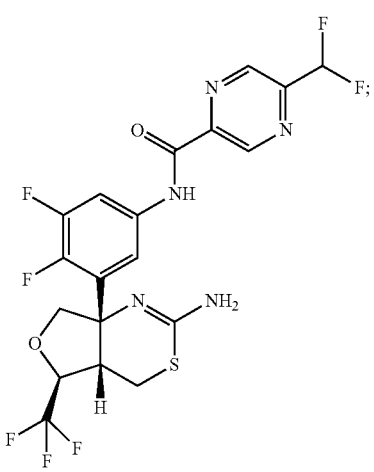 [SMILES: NC1=N[C@@]2(c3cc(NC(=O)c4cnc(C(F)F)cn4)cc(F)c3F)CO[C@H](C(F)(F)F)[C@H]2CS1]

N-(3-((4aS,5S,7aS)-2-amino-5-(trifluoromethyl)-4a,5,7,7a-tetrahydro-4H-furo[3,4-d][1,3]thiazin-7a-yl)-4,5-difluorophenyl)-5-methoxypyrazine-2-carboxamide:

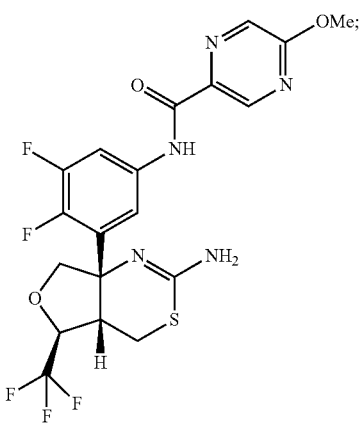 [SMILES: COc1cnc(C(=O)Nc2cc(F)c(F)c([C@]34CO[C@H](C(F)(F)F)[C@H]3CSC(N)=N4)c2)cn1]

N-(3-((4aS,5S,7aS)-2-amino-5-(trifluoromethyl)-4a,5,7,7a-tetrahydro-4H-furo[3,4-d][1,3]thiazin-7a-yl)-4,5-difluorophenyl)-5-methylpyrazine-2-carboxamide:

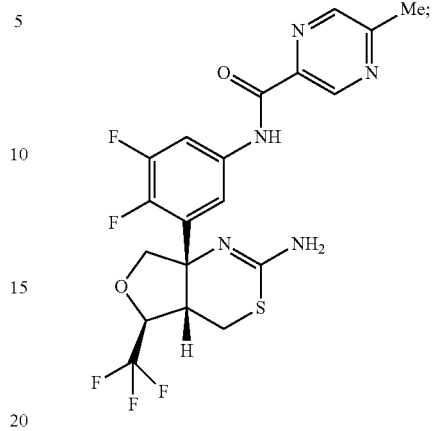

N-(3-((4aS,5S,7aS)-2-amino-5-(trifluoromethyl)-4a,5,7,7a-tetrahydro-4H-furo[3,4-d][1,3]thiazin-7a-yl)-4,5-difluorophenyl)-5-(fluoromethyl)-pyrazine-2-carboxamide:

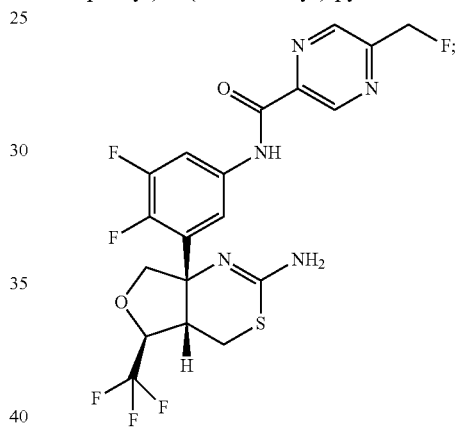

and pharmaceutically acceptable salts thereof.

In one embodiment, the present invention provides a compound which is N-(3-((4aS,5S,7aS)-2-amino-5-(trifluoromethyl)-4a,5,7,7a-tetrahydro-4H-furo[3,4-d][1,3]thiazin-7a-yl)-4-fluorophenyl)-5-methoxypyrazine-2-carboxamide, or a pharmaceutically acceptable salt thereof.

In another embodiment, the present invention provides a compound which is N-(3-((4aS,5S,7aS)-2-amino-5-(trifluoromethyl)-4a,5,7,7a-tetrahydro-4H-furo[3,4-d][1,3]thiazin-7a-yl)-4-fluorophenyl)-5-(fluoromethyl)pyrazine-2-carboxamide, or a pharmaceutically acceptable salt thereof.

Specific compounds within the scope of this invention include those named in the Examples below and their pharmaceutically acceptable salts.

As used herein, the term "difluoroethyl" refers to an alkyl group having two carbon atoms and substituted with two fluorine atoms. Examples of the group are $CH_3$—$CF_2$—, $CH_2F$—$CHF$— and $CHF_2$—$CH_2$—. In the present invention, the group is preferably $CH_3$—$CF_2$—.

The compound of formula (I) is not limited to a specific isomer and includes all possible isomers (such as a keto-enol isomer, an imine-enamine isomer and a rotamer) and mixtures thereof. For example, the compound of formula (I) includes the following tautomers:

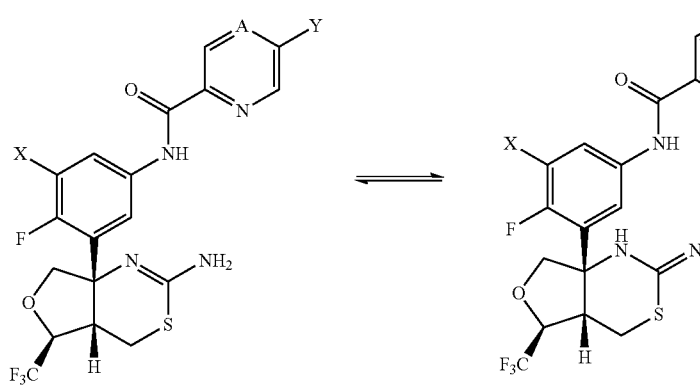

The compounds of the present invention contain three chiral centers located on the tetrahydrofuro-thiazinyl ring within formula (I). The stereochemical configuration at each of these chiral centers is preferably S, i.e. they are (4aS,5S,7aS) stereoisomers. For the avoidance of doubt the (4aS,5S,7aS) stereoisomers of the present invention may be present as a mixture with one or more of the other possible stereoisomers, for example in a racemic mixture.

In one embodiment, the present invention provides a compound of formula (I) which is stereochemically pure at the (4aS,5S,7aS) chiral centers. In the context of the present specification, the term stereochemically pure denotes a compound which has 80% or greater by weight of the (4aS,5S,7aS) stereoisomer and 20% or less by weight of other stereoisomers. In a further embodiment, the compound of formula (I) has 90% or greater by weight of the (4aS,5S,7aS) stereoisomer and 10% or less by weight of other stereoisomers. In a yet further embodiment, the compound of formula (I) has 95% or greater by weight of the (4aS,5S,7aS) stereoisomer and 5% or less by weight of other stereoisomers. In a still further embodiment, the compound of formula (I) has 97% or greater by weight of the (4aS,5S,7aS) stereoisomer and 3% or less by weight of other stereoisomers.

In the present specification, although crystal polymorphs of the compound may be present, the compound is similarly not limited thereto and may be present as a single crystal form or a mixture of single crystal forms. The compound may be an anhydride or a hydrate. Any of these forms is included in the claims of the present specification.

The present invention also includes isotopically-labelled compounds, which are identical to the compounds of formula (I), except that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, fluorine, phosphorous, chlorine, technetium and iodine, such as $^2H$, $^3H$, $^{11}C$, $^{14}C$, $^{13}N$, $^{15}O$, $^{18}F$, $^{32}P$, $^{99m}Tc$, $^{123}I$ and $^{131}I$.

Compounds of the present invention and pharmaceutically acceptable derivatives (e.g. salts) of said compounds that contain the aforementioned isotopes and/or other isotopes of other atoms are within the scope of the present invention. Isotopically-labelled compounds of the present invention, for example those into which radioactive isotopes such as $^3H$ and/or $^{14}C$ are incorporated, are useful in drug and/or substrate tissue distribution assays. $^3H$ and $^{14}C$ are considered useful due to their ease of preparation and detectability. $^{11}C$, $^{15}O$ and $^{18}F$ isotopes are considered useful in PET (positron emission tomography), and $^{99m}Tc$, $^{123}I$ and $^{131}I$ isotopes are considered useful in SPECT (single photon emission computerized tomography), all useful in brain imaging. Substitution with heavier isotopes such as $^2H$ can afford certain therapeutic advantages resulting from greater metabolic stability, for example increased in vivo half-life or reduced dosage requirements and, hence, are considered useful in some circumstances. Isotopically labelled compounds of formula (I) of this invention can generally be prepared by carrying out the procedures disclosed in the Schemes and/or in the Examples below, by substituting a readily available isotopically labelled reagent for a non-isotopically labelled reagent.

The fused aminodihydrothiazine derivative of the formula (I) according to the present invention may be a pharmaceutically acceptable salt. Pharmaceutically acceptable salts include those described by Berge, Bighley and Monkhouse, J. Pharm. Sci., 1977, 766, 1-19. Specific examples of the pharmaceutically acceptable salt include inorganic acid salts (such as sulfates, nitrates, perchlorates, phosphates, carbonates, bicarbonates, hydrofluorides, hydrochlorides, hydrobromides and hydroiodides), organic carboxylates (such as acetates, oxalates, maleates, tartrates, fumarates, citrates, malonates and lactates), organic sulfonates (such as methanesulfonates, trifluoromethanesulfonates, ethanesulfonates, benzenesulfonates, toluenesulfonates and camphorsulfonates), amino acid salts (such as aspartates and glutamates), quaternary amine salts, alkali metal salts (such as sodium salts and potassium salts) and alkali earth metal salts (such as magnesium salts and calcium salts).

The compound of the formula (I) according to the present invention can be converted to a pharmaceutically acceptable salt by a conventional method where necessary. The salt can be prepared by a method in which methods typically used in the field of organic synthetic chemistry and the like are appropriately combined. Specific examples of the method include neutralization titration of a free solution of the compound of the present invention with an acid solution.

The fused aminodihydrothiazine derivative of the formula (I) or pharmaceutically acceptable salt according to the present invention may be a solvate thereof. Examples of a solvate include a hydrate.

The compound of the formula (I) according to the present invention can be converted to a solvate by subjecting the compound to a solvate forming reaction known per se where necessary.

The present invention further provides a compound of formula (I) or a pharmaceutically acceptable salt thereof for use in therapy.

The fused aminodihydrothiazine derivative or pharmaceutically acceptable salt thereof or solvate thereof according to the present invention has an excellent Aβ production inhibitory effect or BACE1 inhibitory effect and is useful as a prophylactic or therapeutic agent for a neurodegenerative disease caused by Aβ and typified by Alzheimer-type dementia. The compounds of the invention reduce both Aβ40 and Aβ42. Furthermore, the compounds of the present invention may have a BACE 2 inhibitory effect.

Thus, in another aspect, the present invention provides a compound of formula (I) as defined above, or a pharmaceutically acceptable salt thereof, for inhibiting production of amyloid-β protein.

In a further aspect, the present invention provides a compound of formula (I) as defined above, or a pharmaceutically acceptable salt thereof, for inhibiting beta-site amyloid-β precursor protein cleaving enzyme 1 (BACE 1).

In a further aspect, the present invention provides a compound of formula (I) as defined above, or a pharmaceutically acceptable salt thereof, for treating a neurodegenerative disease. Examples of neurodegenerative diseases include Alzheimer-type dementia (AD), Down's syndrome, cerebrovascular amyloid angiopathy (CAA), mild cognitive impairment (MCI), memory loss, presenile dementia, senile dementia, hereditary cerebral hemorrhage with amyloidosis, and other degenerative dementias such as dementias of mixed vascular and degenerative origin, dementia associated with supranuclear palsy, dementia associated with cortical basal degeneration, dementia associated with Parkinson's Disease (PD), and dementia associated with diffuse Lewy Body type of AD. In one embodiment, the neurodegenerative disease is Alzheimer-type dementia (AD).

In another aspect, the invention provides the use of a compound of formula (I) as defined above, or a pharmaceutically acceptable salt thereof, for the manufacture of a medicament for the treatment or prevention of a neurodegenerative disease, such as Alzheimer-type dementia (AD), Down's syndrome, cerebrovascular amyloid angiopathy (CAA), mild cognitive impairment (MCI), memory loss, presenile dementia, senile dementia, hereditary cerebral hemorrhage with amyloidosis, and other degenerative dementias such as dementias of mixed vascular and degenerative origin, dementia associated with supranuclear palsy, dementia associated with cortical basal degeneration, dementia associated with Parkinson's Disease (PD), and dementia associated with diffuse Lewy Body type of AD. In one embodiment, the neurodegenerative disease is Alzheimer-type dementia (AD).

In another aspect, the invention provides a method of inhibiting production of amyloid-β protein and/or of treating or preventing a neurodegenerative disease, such as Alzheimer-type dementia (AD), Down's syndrome, cerebrovascular amyloid angiopathy (CAA), mild cognitive impairment (MCI), memory loss, presenile dementia, senile dementia, hereditary cerebral hemorrhage with amyloidosis, and other degenerative dementias such as dementias of mixed vascular and degenerative origin, dementia associated with supranuclear palsy, dementia associated with cortical basal degeneration, dementia associated with Parkinson's Disease (PD), and dementia associated with diffuse Lewy Body type of AD, involving administering to a human subject in need thereof a therapeutically or prophylactically effective amount of a compound of formula (I) or a pharmaceutically acceptable salt thereof. Examples of neurodegenerative diseases include those listed above. In one embodiment, the neurodegenerative disease is Alzheimer-type dementia (AD). "Effective amount" means an amount sufficient to cause a benefit to the subject or at least to cause a change in the subject's condition.

Additional conditions which may be treated by the compounds of the present invention include type 2 diabetes, Creutzfield-Jakob Disease (CJD), peripheral nerve injury, peripheral neuropathy, progressive supra-nuclear palsy, stroke, amyotrophic lateral sclerosis (ALS), autoimmune diseases, inflammation, arterial thrombosis, anxiety disorders, psychotic disorders, epilepsy, seizures, convulsions, stress disorders, vascular amyloidosis, pain, Gerstmann-Straeussler-Scheinker syndrome, scrapie, encephalopathy, spino cerebellar ataxia, Wilson's Disease, Graves Disease, Huntington's Disease, Whipple's Disease, Kostmann Disease, glaucoma, hereditary cerebral hemorrhage with amyloidosis, cerebral hemorrhage with amyloidosis, vascular amyloidosis, brain inflammation, fragile X syndrome, stroke, Tourette's syndrome, inclusion body myositis, stress disorders, depression, bipolar disorder and obsessive compulsive disorder.

In one aspect the present invention further provides a compound of formula (I) as defined above, or a pharmaceutically acceptable salt thereof, for treating type 2 diabetes. In a further aspect the present invention further provides the use of a compound of formula (I) as defined above, or a pharmaceutically acceptable salt thereof, for the manufacture of a medicament for the treatment or prevention of type 2 diabetes.

In a yet further aspect the present invention further provides a method of inhibiting production of amyloid-β protein and/or of treating or preventing type 2 diabetes involving administering to a human subject in need thereof a therapeutically or prophylactically effective amount of a compound of formula (I) or a pharmaceutically acceptable salt thereof.

A further aspect of the invention provides a pharmaceutical composition comprising a compound of formula (I) as defined above, or a pharmaceutically acceptable salt thereof, as active ingredient in association with a pharmaceutically acceptable carrier. The composition may be in any suitable form, depending on the intended method of administration. It may for example be in the form of a tablet, capsule or liquid for oral administration, or of a solution or suspension for administration parenterally.

The fused aminodihydrothiazine derivative or pharmaceutically acceptable salt thereof according to the present invention can be formulated by a conventional method. Preferable examples of the dosage form include tablets, coated tablets such as film tablets and sugar-coated tablets, fine granules, granules, powders, capsules, syrups, troches, inhalants, suppositories, injections, ointments, eye drops, nasal drops, ear drops, cataplasms and lotions.

These solid preparations such as tablets, capsules, granules and powders can contain generally 0.01 to 100 wt %, and preferably 0.1 to 100 wt % of the fused aminodihydrothiazine derivative or pharmaceutically acceptable salt thereof according to the present invention as an active ingredient.

The active ingredient is formulated by blending ingredients generally used as materials for a pharmaceutical preparation and adding an excipient, a disintegrant, a binder, a lubricant, a colorant and a corrective typically used, and adding a stabilizer, an emulsifier, an absorbefacient, a surfactant, a pH adjuster, a preservative and an antioxidant where necessary, for example, using a conventional method. Examples of such ingredients include animal and vegetable oils such as soybean oil, beef tallow and synthetic glyceride; hydrocarbons such as liquid paraffin, squalane and solid paraffin; ester oils such as octyldodecyl myristate and isopropyl myristate; higher alcohols such as cetostearyl alcohol and behenyl alcohol; a silicone resin; silicone oil; surfactants such as polyoxyethylene fatty acid ester, sorbitan fatty acid ester, glycerol fatty acid ester, polyoxyethylene sorbitan fatty acid ester, polyoxyethylene hydrogenated castor oil and a polyoxyethylene-polyoxypropylene block copolymer; water-soluble polymers such as hydroxyethylcellulose, polyacrylic acid, a carboxyvinyl polymer, polyethylene glycol, polyvinylpyrrolidone and methylcellulose; lower alcohols such as ethanol and isopropanol; polyhydric alcohols such as glycerol, propylene glycol, dipropylene glycol and sorbitol; sugars such as glucose and sucrose; inorganic powders such as silicic anhydride, magnesium aluminum silicate and aluminum silicate; and purified water. Examples of the excipient used include lactose, corn starch, saccharose, glucose, mannitol, sorbitol, crystalline cellulose and silicon dioxide. Examples of the binder used include polyvinyl alcohol, polyvinyl ether, methylcellulose, ethylcellulose, gum arabic, tragacanth, gelatin, shellac, hydroxypropylmethylcellulose, hydroxypropylcellulose, polyvinylpyrrolidone, a polypropylene glycol-polyoxyethylene block copolymer and meglumine. Examples of the disintegrant used include starch, agar, gelatin powder, crystalline cellulose, calcium carbonate, sodium bicarbonate, calcium citrate, dextrin, pectin and carboxymethylcellulose calcium. Examples of the lubricant used include magnesium stearate, talc, polyethylene glycol, silica and hydrogenated vegetable oil. Examples of the colorant used include those permitted to be added to pharmaceuticals. Examples of the corrective used include cocoa powder, menthol, empasm, mentha oil, borneol and cinnamon powder. Obviously, the ingredients are not limited to the above additive ingredients.

For example, an oral preparation is prepared by adding the fused aminodihydrothiazine derivative or pharmaceutically acceptable salt thereof according to the present invention as an active ingredient, an excipient and, where necessary, a binder, a disintegrant, a lubricant, a colorant, a corrective and the like, and then forming the mixture into powder, fine granules, granules, tablets, coated tablets, capsules or the like by a conventional method. Obviously, tablets or granules may be appropriately coated, for example, sugar coated, where necessary.

For example, a syrup or an injection preparation is prepared by adding a pH adjuster, a solubilizer, an isotonizing agent and the like, and a solubilizing agent, a stabilizer and the like where necessary by a conventional method. The injection may be a previously prepared solution, or may be powder itself or powder containing a suitable additive, which is dissolved before use. The injection can contain usually 0.01 to 100 wt %, and preferably 0.1 to 100 wt % of the active ingredient. Further, a liquid preparation for oral administration such as a suspension or a syrup can contain usually 0.01 to 100 wt %, and preferably 0.1 to 100 wt % of the active ingredient.

For example, an external preparation can be prepared by any conventional method without specific limitations. As a base material, any of various materials usually used for a pharmaceutical, a quasi drug, a cosmetic or the like can be used. Examples of the base material include materials such as animal and vegetable oils, mineral oils, ester oils, waxes, higher alcohols, fatty acids, silicone oils, surfactants, phospholipids, alcohols, polyhydric alcohols, water-soluble polymers, clay minerals and purified water. A pH adjuster, an antioxidant, a chelator, a preservative and fungicide, a colorant, a flavor or the like can be added where necessary. Further, ingredients such as an ingredient having a differentiation inducing effect, a blood flow enhancer, a bactericide, an antiphlogistic, a cell activator, vitamin, amino acid, a humectant and a keratolytic agent can be blended where necessary.

The dose of the fused aminodihydrothiazine derivative or pharmaceutically acceptable salt thereof according to the present invention varies according to the degree of symptoms, age, sex, body weight, mode of administration, type of salt and specific type of disease, for example. Typically, the active ingredient is orally administered to an adult at about 30 μg to 10 g, preferably 100 μg to 5 g, and more preferably 100 μg to 1 g per day, or is administered to an adult by injection at about 30 μg to 1 g, preferably 100 μg to 500 mg, and more preferably 100 μg to 300 mg per day, in one or several doses, respectively.

Compounds of the formula (I) may be used in combination with other therapeutic agents, for example medicaments claimed to be useful as either disease modifying or symptomatic treatments of a neurodegenerative disease such as Alzheimer's disease. Thus, in a further aspect, the present invention provides a pharmaceutical product comprising, in combination, a first active ingredient which is a compound of formula (I) or a pharmaceutically acceptable salt thereof and at least one further active ingredient useful in treating a neurodegenerative disease. In one embodiment of the invention, the neurodegenerative disease is Alzheimer-type dementia (AD). Suitable examples of such further active ingredients may be symptomatic agents, for example those known to modify cholinergic transmission such as M1 and M3 muscarinic receptor agonists or allosteric modulators, M2 muscarinic antagonists, M4 agonists or positive allosteric modulators (PAMs), acetylcholinesterase inhibitors (such as tetrahydroaminoacridine, donepezil hydrochloride and rivastigmine), nicotinic receptor agonists or allosteric modulators (such as α7 agonists or allosteric modulators or α4β2 agonists or allosteric modulators), PPAR agonists (such as PPARγ agonists), 5-HT$_4$ receptor agonists or partial agonists, histamine H3 antagonists, 5-HT$_6$ receptor antagonists or 5HT$_7$ receptor ligands and NMDA receptor antagonists or modulators, 5-HT$_{2A}$ antagonists, 5-HT$_7$ antagonists, D1 agonists or PAMs, D4 agonists or PAMs, D5 agonists or PAMs, GABA-A α5 inverse agonists or negative allosteric modulators (NAMs), GABA-A α2/3 agonists or PAMs, mGluR2 modulators (PAMs or NAMs), mGluR3PAMs, mGluR5PAMs, PDE 1 inhibitors, PDE 2 inhibitors, PDE 4 inhibitors, PDE 5 inhibitors, PDE 9 inhibitors, PDE 10 inhibitors, GlyT1 inhibitors, DAAO inhibitors, ASC1 inhibitors, AMPA modulators, SIRT1 activators or inhibitors, AT4 antagonists, GalR1 antagonists, GalR3 ligands, adenosine A1 antagonists, adenosine A2a antagonists, α2A antagonists or agonists, selective and unselective norepinephrine reuptake inhibitors (SNRIs), or potential disease modifying agents such as gamma secretase inhibitors or modulators, alpha secretase activators or modulators, amyloid aggregation inhibitors, amyloid antibodies, tau aggregation inhibitors or tau phosphorylation/kinase inhibitors, tau dephosphorylation/phosphatase activators, mitogen-activated protein kinase kinase 4 (MKK4/MEK4/MAP2K4) inhibitors, c-Jun N-terminal kinase (INK) inhibitors, casein kinase inhibitors, MK2 (mitogen activated protein kinase-activated protein kinase 2) inhibitors, MARK (microtubule affinity regulating kinase) inhibitors, CDKS (cyclin dependent kinase 5) inhibitors, GSK-3 (glycogen synthase kinase-3) inhibitors and tau-tubulin kinase-1 (TTBK1) inhibitors. Further examples of such other therapeutic agents may be calcium channel blockers, HMG-CoA (3-hydroxy-3-methyl-glutaryl-CoA) reductase inhibitors (statins) and lipid lowering agents, NGF (nerve growth factor) mimics, antioxidants, GPR3 ligands, plasmin activators, neprilysin (NEP) activators, IDE (insulin degrading enzyme) activators, melatonin MT1 and/or MT2 agonists, TLX/NR2E1 (tailless X receptor) ligands, GluR1 ligands, RAGE (receptor for advanced glycation end-products) antagonists, EGFR (epidermal growth factor receptor) inhibitors, FPRL-1 (formyl peptide-like receptor-1) ligands, GABA antagonists, and MICAL (molecule interacting with casL) inhibitors, e.g. oxoreductase inhibitors, CB1 antagonists/inverse agonists, non-steroidal anti-inflammatory drugs (NSAIDs), anti-inflammatory agents (for example agents that could be used to treat neuroinflammation either by enhancing or reducing neuroinflammation), amyloid precursor protein (APP) ligands, anti-amyloid vaccines and/or antibodies, agents that promote or enhance amyloid efflux and/or clearance, histone deacetylase (HDAC) inhibitors, EP2 antagonists, 11-beta HSD1 (hydroxysteroid dehydrogenase) inhibitors, liver X receptor (LXR) agonists or PAMs, lipoprotein receptor-related protein (LRP) mimics and/or ligands and/or enhancers and/or inhibitors, butyryl cholinesterase inhibitors, kynurinic acid antagonists and/or inhibitors of kynurenine aminotransferease (KAT), orphanin FQ/nociceptin (NOP)/opioid-like receptor 1 (ORL1) antagonists, excitatory amino acid transporter (EAAT) ligands (activators or inhibitors), and plasminogen activator inhibitor-1 (PAI-1) inhibitors, niacin and/or GPR109 agonists or PAMs in combination with cholesterol lowering agents and/or HMGCoA reductase inhibitors (statins), dimebolin or similar agents, antihistamines, metal binding/chelating agents, antibiotics, growth hormone secretagogues, cholesterol lowering agents, vitamin E, cholesterol absorption inhibitors, cholesterol efflux promoters and/or activators, and insulin upregulating agents.

In one embodiment, the present invention provides a pharmaceutical product comprising, in combination, a first active ingredient which is a compound of formula (I) or a pharmaceutically acceptable salt thereof and at least one further active ingredient selected from:—
  cholinesterase inhibitors, e.g. donepezil, galantamine, rivastigamine, tetrahydroaminoacridine and pharmaceutically acceptable salts thereof,
  $5\text{-HT}_6$ antagonists, e.g. SB-742457 and pharmaceutically acceptable salts thereof,
  HMGCoA reductase inhibitors e.g. lovastatin, rosuvastatin, atorvastatin, simvastatin, fluvastatin, pitavastatin, pravastatin and pharmaceutically acceptable salts thereof.

The individual components of such combinations may be administered either sequentially or simultaneously in separate or combined pharmaceutical formulations. Consequently, the pharmaceutical product may, for example be a pharmaceutical composition comprising the first and further active ingredients in admixture. Alternatively, the pharmaceutical product may for example comprise the first and further active ingredients in separate pharmaceutical preparations suitable for simultaneous, sequential or separate administration to a patient in need thereof.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention.

When a compound of formula (I) or a pharmaceutically acceptable salt thereof is used in combination with a second therapeutic agent active, the dose of each compound may differ from that when the compound is used alone. Appropriate doses will be readily appreciated by those skilled in the art.

Thus, an additional aspect of the invention provides a method of preparation of a pharmaceutical composition, involving admixing at least one compound of formula (I) as defined above, or a pharmaceutically acceptable salt thereof, with one or more pharmaceutically acceptable adjuvants, diluents or carriers and/or with one or more other therapeutically or prophylactically active agents.

In one embodiment, the present invention provides a pharmaceutical composition comprising a compound of formula (I) or a pharmaceutically acceptable salt thereof, one or more other agents for the treatment of Alzheimer's disease, such as an M1 and M3 muscarinic receptor agonist or allosteric modulator, an M2 muscarinic antagonist, an acetylcholinesterase inhibitor, a nicotinic receptor agonist or allosteric modulator, a PPAR agonist, a 5-HT4 receptor agonist or partial agonist, a histamine H3 antagonist, a $5\text{-HT}_6$ receptor antagonist, a $5\text{HT}_{1A}$ receptor ligand, a NMDA receptor antagonist or modulator, a $5\text{-HT}_{2A}$ antagonist, a $5\text{-HT}_7$ antagonist, a D1 agonist or positive allosteric modulator (PAM), a D4 agonist or PAM, a GABA-A a5 inverse agonist or negative allosteric modulator (NAM), a GABA-A a2/3 agonist or PAM, a mGluR2 modulator (PAM or NAM), a mGluR3 PAM, a mGluR5 PAM, a PDE 1 inhibitor, a PDE 2 inhibitor, a PDE 4 inhibitor, a PDE 5 inhibitor, a PDE 9 inhibitor, a PDE 10 inhibitor, a GlyT1 inhibitor, a DAAO inhibitor, a ASC1 inhibitor, a AMPA modulator, a SIRT1 activator or inhibitor, a AT4 antagonist, a GalR1 antagonist, a GalR3 ligand, an adenosine A1 antagonist, an adenosine A2a antagonist, an α2A antagonist or agonist, a selective or unselective norepinephrine reuptake inhibitor (SNRT), a gamma secretase inhibitor or modulator, an alpha secretase activator or modulator, an amyloid aggregation inhibitor, an amyloid antibody, a tau aggregation inhibitor, a tau phosphorylation inhibitor, a MK2 (mitogen activated protein kinase-activated protein kinase 2) inhibitor, a MARK (microtubule affinity regulating kinase) inhibitor, a CDKS (cyclin dependent kinase 5) inhibitor, a GSK-3 (glycogen synthase kinase-3) inhibitor, a calcium channel blocker, a HMG-CoA (3-hydroxy-3-methyl-glutaryl-CoA) reductase inhibitor (statin) and a lipid lowering agent, a NGF (nerve growth factor) mimic, an antioxidant, a GPR3 ligand, a plasmin activator, a neprilysin (NEP) activator, an IDE (insulin degrading enzyme) activator, a melatonin MT1 and/or MT2 agonist, a TLX (tailless X receptor) ligand, a GluR1 ligand, a RAGE (receptor for advanced glycation end-products) antagonist, an EGFR (epidermal growth factor receptor) inhibitor, a FPRL-1 (formyl peptide-like receptor-1) ligand, a GABA antagonist or a MICAL (molecule interacting with casL) inhibitor such as an oxoreductase inhibitor, in association with a pharmaceutically acceptable carrier. In a further embodiment the present invention provides a combination comprising a compound of formula (I) or a pharmaceutically acceptable salt thereof, together with a further therapeutic agent as described herein above for sequential or simultaneous administration in separate or combined pharmaceutical formulations.

In a further aspect, the invention provides a method of inhibiting production of amyloid-β protein and/or of treating or preventing a neurodegenerative disease, such as Alzheimer-type dementia (AD), Down's syndrome, cerebrovascular amyloid angiopathy (CAA), mild cognitive impairment (MCI), memory loss, presenile dementia, senile dementia, hereditary cerebral hemorrhage with amyloidosis, and other degenerative dementias such as dementias of mixed vascular and degenerative origin, dementia associated with supranuclear palsy, dementia associated with cortical basal degeneration, dementia associated with Parkinson's Disease (PD), and dementia associated with diffuse Lewy Body type of AD, the method involving administering to a human subject suffering from the condition a therapeutically or prophylactically effective amount of the pharmaceutical composition described above or of a compound of formula (I) as defined above, or a pharmaceutically acceptable salt thereof. "Effective amount" means an amount sufficient to cause a benefit to the subject or at least to cause a change in the subject's condition.

Alzheimer's Disease (AD) is characterized pathologically by the presence of neurofibrillary tangles (NFTs) and plaques, consisting of amyloid (Aβ) peptides of varying length, for example 42 amino acids (Aβ42) and 40 amino acids (Aβ40). In addition to these pathological markers, brain atrophy is also evident. The build up of plaques is believed to be due to the aggregation of Aβ peptides. Aβ peptides are formed in the brain by the sequential cleavage of amyloid precursor protein (APP) by β-secretase (BACE-1) and γ-secretase. Therefore potential AD drugs aimed at inhibiting amyloid formation by inhibiting BACE-1 or γ-secretase, must be able to achieve adequate exposure in the brain, in order to exert an effect on AD.

Although BACE-1 represents an attractive target to halt or slow the production of amyloid peptides, various groups have found it challenging to identify BACE-1 inhibitors that can penetrate the central nervous system (CNS) and thus inhibit the enzyme at the site of action.

The brain is protected by several barriers including the blood brain barrier (BBB) and transporters (Hitchcock and Pennington, J Med Chem 2006, 29, 7559; Ueno, Curr. Med. Chem. 2007, 14, 1199; Gloor et al., Brain Res. Rev. 2001, 36, 258). Several efflux transporters have been characterised which prevent compounds entering the brain. One of the best characterised and most prominent in preventing the CNS penetration of xenobiotics is P-glycoprotein (Pgp) (Kusuhara and Sugiyama, Drug Discovery Today, 2001, 6, 150; Mahar Doan et al., J. Pharm. Expt. Ther. 2002, 303, 1029; Lin, Drugs of Today 2004, 40, 5; Lin & Yamazaki, Clin Pharmacokinet. 2003, 42, 59; Schinkel, Adv. Drug Deliv. Rev. 1999, 36, 179). It has been shown that Pgp efflux is important for BACE-1 inhibitors (Hussain et al., J. Neurochem. 2007, 100, 802). Thus, overcoming Pgp efflux is important.

Those skilled in the art will appreciate that there are several ways to measure or predict CNS penetration in vitro or in vivo. The potential for CNS penetration can be assessed in vitro by determining whether a compound can be subjected to Pgp efflux, i.e. by conducting an in vitro Pgp assay. Those skilled in the art will appreciate that a number of cell lines can be used and that these cell lines may or may not affect the results of the assay. One such assay is described below (Cyprotex UK).

The following MDR-1 MDCK assay was used to assess Pgp efflux. The assay was conducted at Cyprotex Discovery Ltd. 15 Beech Lane, Macclesfield, Cheshire, UK, SK10 2DR MDR1-MDCK Permeability (Bi-Directional; pH 7.4/pH 7.4)
Protocol Summary MDCK cells are an epithelial cell line of canine kidney origin. These cells can be transfected to stably express active P-glycoprotein (MDR1-MDCK) and are ideal for studying drug efflux. Test compound was added to either the apical or basolateral side of a confluent monolayer of MDR1-MDCK cells and permeability was measured by monitoring the appearance of the test compound on the opposite side of the membrane using LC-MS/MS. From this an apparent permeability ($P_{app}$) coefficient and efflux ratio was measured/calculated.

Objective

To measure the permeability of test compound in the apical to basolateral (A-B) and basolateral to apical (B-A) direction across MDR1-MDCK cells. A ratio of B-A and A-B permeabilities was calculated (efflux ratio) to show whether the compound undergoes P-glycoprotein efflux.

Compounds were provided as a 200 μL solution of 10 mM test compound in DMSO.

Experimental Procedure

MDR1-MDCK cells obtained from the NIH (Rockville, Md., USA) were used. Following culture to confluency, the monolayers were prepared by rinsing both basolateral and apical surfaces twice with pH 7.4 buffer at 37° C. Cells were then incubated with pH 7.4 buffer in both apical and basolateral compartments for 40 min to stabilise physiological parameters.

Buffer at pH 7.4 was then removed from the apical compartment and replaced with test compound dosing solutions. The solutions were prepared by diluting 10 mM test compound in DMSO with buffer to give a final test compound concentration of 10 μM (final DMSO concentration adjusted to 1%). The fluorescent integrity marker Lucifer yellow was also included in the dosing solution. The apical compartment inserts were then placed into 'companion' plates containing fresh buffer at pH 7.4. Analytical standards were made from dosing solutions.

For basolateral to apical (B-A) experiments the experiment was initiated by replacing buffer in the inserts then placing them in companion plates containing dosing solutions. Incubations were carried out in an atmosphere of 5% $CO_2$ with a relative humidity of 95% at 37° C. for 60 minutes.

After the incubation period, the companion plate was removed and apical and basolateral samples diluted for analysis by LC-MS/MS. Test compound permeability was assessed in duplicate. On each plate compounds of known permeability characteristics were run as controls.

Test and control compounds were quantified by LC-MS/MS cassette analysis using a 5-point calibration with appropriate dilution of the samples. Cyprotex generic analytical conditions were used. The starting concentration ($C_0$) was determined from the dosing solution and the experimental recovery calculated from $C_0$ and both apical and basolateral compartment concentrations.

The integrity of the monolayers throughout the experiment was checked by monitoring Lucifer yellow permeation using fluorimetric analysis. Lucifer yellow permeation is low if monolayers have not been damaged. If a Lucifer yellow $P_{app}$ value was above QC limits in one individual test compound well, then an n=1 result was reported. If Lucifer yellow $P_{app}$ values were above QC limits in both replicate wells for a test compound, the compound was re-tested. If on repeat, high Lucifer yellow permeation was observed in both wells then toxicity or inherent fluorescence of the test compound was assumed. No further experiments were performed in this instance.

Data Analysis

The permeability coefficient for each compound ($P_{app}$) was calculated from the following equation:

$$P_{app}=(dQ \div dt) \div (C_0 \times A)$$

Where dQ/dt is the rate of permeation of the drug across the cells, $C_0$ is the donor compartment concentration at time zero and A is the area of the cell monolayer. $C_0$ was obtained from analysis of the dosing solution at the start of the experiment.

In addition, an efflux ratio (ER) was calculated from mean A-B and B-A data. This is derived from:

$$ER=((P_{app}(B-A)) \div ((P_{app}(A-B)))$$

Two control compounds were screened alongside the test compounds, propranolol (highly permeable) and prazosin (a substrate for P-glycoprotein).

Surprisingly, compounds from the present invention were found to display a lower Pgp efflux ratio than compounds exemplified in WO2009/091016 indicating that they have the potential to show higher CNS penetration. Data for selected examples are shown in Table 1 below.

TABLE 1

MDR-1 MDCK Pgp assay data

| Example | Pgp ER |
|---|---|
| Comparative Example 1 | 26.2 |
| Comparative Example 2 | 16.6 |
| Comparative Example 3 | 24.0 |
| Comparative Example 4 | 20.7 |
| 2 | 1.7 |
| 3 | 1.4 |
| 4 | 1.0 |
| 1 | 0.7 |
| Comparative Example 5 | 4.7 |
| Comparative Example 6 | 4.5 |
| 10 | 0.6 |
| 5 | 1.5 |
| 6 | 1.0 |
| 7 | 0.8 |
| 8 | 1.7 |
| 9 | 1.2 |
| 11 | 1.0 |
| 12 | 0.8 |
| 13 | 1.7 |
| 15 | 1.6 |
| 16 | 1.1 |
| 17 | 1.4 |
| 18 | 1.1 |

Note:
Example 14 is intentionally not included.

Comparative Examples 1 to 6 are covered by published International patent application WO2009/091016; Comparative Examples 1 to 4 are specifically described in WO2009/091016 as Examples 32, 35, 54 and 73 respectively. Comparative Examples 5 and 6 are N-(3-((4aS,5S,7aS)-2-amino-5-(fluoromethyl)-4a,5,7,7a-tetrahydro-4H-furo[3,4-d][1,3]thiazin-7a-yl)-4-fluorophenyl)-5-ethoxypicolinamide, and N-(3-((4aS,5R,7aS)-2-amino-5-methyl-4a,5,7,7a-tetrahydro-4H-furo[3,4-d][1,3]thiazin-7a-yl)-4-fluorophenyl)-5-ethoxypicolinamide respectively.

The data demonstrate that compounds of the present invention and specific examples 1-13 and 15-18 have lower Pgp efflux and therefore potentially higher CNS penetration than representative examples from WO2009/091016 using the aforementioned recognized method of assessing CNS penetration. For example, Comparative Examples 1 to 6 have higher Pgp efflux ratios than compounds of the present invention. Furthermore, Comparative Examples 5 and 6 have higher Pgp efflux ratios than a close analogue, Example 10 of the present invention, which clearly demonstrates the beneficial effect the trifluoromethyl group on the tetrahydrofuran ring exerts on Pgp efflux, i.e. the trifluoromethyl group reduces Pgp efflux.

Those skilled in the art will appreciate that the in vitro Pgp assay described above is a predictive assay of in vivo CNS penetration. It is thus also highly desirable if the decreased Pgp-mediated efflux translates to the in vivo situation. Those skilled in the art will appreciate there are many ways to assess the CNS penetration of compounds in vivo. For example, one can quantify compound concentrations in blood or plasma and brain and calculate a brain:blood (Br:Bl) or brain:plasma (Br:Pl) ratio. This method has been used historically and has been widely accepted as a method of determining CNS penetration (Summerfield et al., J Pharmacol. Expt. Ther. 2007, 322, 205). Those skilled in the art will appreciate that this type of assay could be conducted at steady state, a single time point, multiple time points or could be done by quoting Area Under the Curve (AUC) ratios. All methods are equally valid but each may have certain caveats that will be appreciated by those skilled in the art. Recent literature has been published to suggest that it is important to consider the free concentrations in vivo and that when no efflux occurs from the brain the free plasma concentration should be the same or equivalent to the free brain concentration (Kalvass and Maurer, Biopharmaceutics & Drug Disposition 2002, 23, 327; Mauer et al, Drug Metab. Disposition 2005, 33, 175; Trainor Expert Opin. Drug Discov. 2007, 2, 51). Thus, a compound that can freely penetrate the CNS and is not subjected to active efflux, for example by Pgp or another transporter, should demonstrate a free brain:free plasma ($Br_{fr}:Pl_{fr}$) or an unbound brain:unbound plasma ($Br_u:Pl_u$) of approximately 1:1. Those skilled in the art will appreciate that the free or unbound concentrations can be calculated by multiplying the total brain or total plasma concentration by the fraction unbound in brain tissue or plasma, which can be measured by the assay described below. Those skilled in the art will appreciate that the fraction unbound may change with experimental factors, for example concentration, or temperature, etc. Those skilled in the art will be able to assess this and select the most appropriate set of conditions. Those skilled in the art will also appreciate that as long as the conditions are the same for each compound screened then the assay will give consistent data for the range of compounds tested thus minimising any discrepancies. It has also been proposed that drug concentrations in cerebrospinal fluid (CSF) are equivalent to free brain concentrations for compounds which are not actively effluxed from the brain (He et al., Xenobiotica 2009, 39, 687). Thus another method of determining CNS penetration would be to assess the CSF:free plasma ($CSF:Pl_{fr}$) or CSF:unbound plasma ($CSF:Pl_u$). If the free drug in plasma is able to permeate into the CNS and is not actively influxed or effluxed then the $CSF:Pl_{fr}$ or $CSF:Pl_u$ should be approximately 1:1. Those skilled in the art will appreciate the issues associated with determining CSF drug concentrations and extracting CSF, for example CSF can be contaminated by blood depending on the method of withdrawal, also the CSF concentrations may be of lower accuracy, depending on the dose used.

Thus it has been shown that a BACE inhibitor from GlaxoSmithKline (GSK188909), BACE-1 $IC_{50}$ 5 nM, which has low CNS exposure was ineffective at lowering Aβ40 production in the brains of TASTPM mice (which overexpress both human APPswe$^{K59N/M596I}$ and PS-1$^{M146V}$) upon acute administration (Hussain et al., J. Neurochem. 2007, 100, 802-809). Following an oral dose of 250 mg/kg the brain concentration of GSK188909 in TASTPM mice was 0.62 uM. When a Pgp inhibitor (GF120918) was dosed 5 hours before the oral administration of GSK188909, the brain concentration of GSK188909 was found to be 5.43 uM following an oral dose of 250 mg/kg, i.e. the co-administration of a Pgp inhibitor caused an almost 9-fold increase in CNS penetration, showing Pgp efflux is an important mechanism in preventing BACE inhibitors from penetrating the CNS. Furthermore, in the absence of a Pgp inhibitor, a 250 mg/kg oral dose of GSK188909 did not have any effect on brain Aβ40 levels in TASTPM mice, whereas when a Pgp inhibitor was co-administered (5 hours prior to the administration of GSK188909) a 68% reduction in brain Aβ40 levels relative to vehicle treated mice was observed.

Another paper has reported a similar effect with three BACE-1 inhibitors from Bristol-Myers Squibb (Meredith et al., J. Pharm. Expt. Ther. 2008, 326, 502-513). The three reported compounds were found to be Pgp substrates in vitro. When dosed to mice, the three compounds showed low CNS penetration and did not lower amyloid levels in the brain but were able to lower plasma amyloid levels. When the same three compounds were administered to Pgp knockout (KO) mice, the level of CNS penetration increased and the compounds were able to lower amyloid levels in the brain.

Researchers at Schering-Plough have also published papers (Iserloh et al., Bioorg. Med. Chem. Lett. 2008, 18, 418) to show that BACE-1 inhibitors from their series (e.g. example 11 from the aforementioned reference), are subject to Pgp efflux, as a result of which the compound was found to display a low Br:Pl (<0.1) in the rat.

The literature cited above emphasises the difficulties in identifying BACE-1 inhibitors which are not subjected to Pgp efflux. Such inhibitors would be highly desirable and many research groups have attempted to discover such compounds without success. Thus BACE-1 inhibitors which are not Pgp substrates and can therefore readily penetrate the CNS and lower amyloid in the brain would be desirable.

More recently, researchers at Wyeth have reported extensive work to overcome Pgp efflux in a series of cyclic acylguanidine BACE-1 inhibitors (Malamas et al, Bioorg. Med. Chem. Lett. 2010, 20, 6597). Compounds were discovered that were weak Pgp substrates and with Br:Pl approaching 1:1. However, two lead examples with reduced Pgp efflux (84 and 89 from the aforementioned reference), did not lower Aβ40 in the brain of Tg2576 mice 8 hours after a 30 mg/kg oral dose. The lack of efficacy was attributed to the fact the compounds showed high brain tissue binding. Thus, it is important to discover BACE-1 inhibitors that are not Pgp substrates but still have a reasonable unbound fraction in brain tissue and are able to lower amyloid in the brain.

It has also been shown that BACE inhibitors that are not Pgp substrates in vitro can penetrate the CNS (e.g. TC-1 from Merck), and can lower Aβ40 levels in the brain of APP-YAC mice and monkeys (Sankaranarayanan et al., J. Pharmacol. Expt. Ther. 2009, 328, 131-140). Thus, in vitro Pgp assays showed TC-1 not to be a Pgp substrate and when TC-1 was dosed to APP-YAC mice (100 mg/kg i.p.) it was able to modestly penetrate the CNS as shown by the brain concentrations and the brain:plasma ratio and this ability resulted in moderate lowering of brain amyloid.

| Time | Plasma conc. (µM) | Brain conc. (µM) | Br:Pl | Reduction in brain Aβ40 (%) |
|---|---|---|---|---|
| 2 h | 25 | 1.6 | 0.06 | 26 |
| 4 h | 13 | 1.8 | 0.14 | 29 |

Brain and plasma concentration of TC-1 following 100 mg/kg i.p. dose and corresponding effects on brain Ab40 levels, in APP-YAC mice.

In separate experiments it was shown that TC-1 could penetrate the CSF of monkeys when co-administered with a CYP3A4 inhibitor (ritonavir). In these experiments the average plasma concentration of TC-1 was found to be 2.7 uM, whilst the CSF concentration was found to be 0.025 uM. However, as TC-1 is ~99% bound to plasma proteins the free plasma concentration was calculated to be ~0.027 nM. It was found that CSF Aβ40 levels showed a 42% decrease relative to a vehicle treated control group. Thus, a BACE inhibitor that can freely penetrate the CNS would be expected to be able to lower amyloid levels in the CNS. It would be beneficial not to have to be co-dosed with a CYP3A4 inhibitor.

The compounds of the present invention have been shown to lower Aβ production in cellular assays which correlates with their ability to lower Aβ production in animals. Thus, the compounds of the present invention will have utility in lowering Aβ production in humans and thus will be useful in the treatment of neurodegenerative diseases such as Alzheimer's disease.

Rat In Vivo CNS Penetration

Male Sprague Dawley rats were acquired from Charles River UK Ltd. (Margate, UK) and housed according to UK Home Office guidelines. Drugs were made up to the appropriate concentrations in 0.5% methyl cellulose. Animals were dosed orally (2 mL/kg) by gavage at the doses outlined in Tables 2 to 4 below.

At the time points post-dosing, specified in Tables 2 to 4 below the animals were administered an i.p. injection of sodium pentobarbitone (approximately 330 mg/kg for terminal anaesthesia).

Using a guillotine, the animals were decapitated and trunk blood collected into 15 ml Falcon tubes containing 100 IU heparin. Blood was vortexed followed by centrifugation at 6000 rpm, 4° C. for 5 minutes. Plasma was collected for DMPK and ELISA assays and stored at −80° C. until use. Brains were dissected out and divided along the midline, weighed and stored at −80° C. until further use.

Method for Analysis of Plasma, Brain and CSF Samples
Preparation of Acetonitrile Working Solutions Test compound was prepared as a 1 mg free base/mL solution in DMSO, vortexed and sonicated for 5 min. The 1 mg/mL DMSO solution was diluted to 10 and 30 µg/mL acetonitrile stocks, by adding 10 µL to 990 µL acetonitrile and 30 µL to 970 µL acetonitrile, respectively. The 10 and 30 µg/mL acetonitrile stocks were then serially diluted 1:9 (v/v) (100 µL stock into 900 µL acetonitrile) to give the following solutions: 0.003, 0.01, 0.03, 0.1, 0.3, 1, 3, 10 and 30 µg/mL acetonitrile.

Preparation of Plasma Standards, Blanks and Samples

Control male Sprague Dawley rat plasma and the study plasma samples were stored at −80° C. until the day of analysis when they were thawed at room temperature. Control plasma was centrifuged (2,000 g for 10 min) and aliquoted (90 µL) into eppendorf tubes for preparation of standards and blank samples. Study samples were previously aliquoted (100 µL) into eppendorf tubes immediately following collection of the plasma.

An aliquot (10 µL) of the appropriate acetonitrile stock was added to the control plasma (to give a final volume of 100 µL) to give the required calibration standards covering the range 1-3000 ng/mL. Double blank and blank samples were prepared by adding 10 µL of acetonitrile to 90 µL of blank plasma.

Preparation of Brain Standards, Blanks and Samples

Control male Sprague Dawley rat brain and the study brain samples were weighed after collection and stored at −80° C. until the day of analysis when they were thawed at room temperature. Once thawed brains were diluted with water (4 mL per gram of tissue) and homogenised using a mechanical homogeniser. An aliquot (100 µL) of each study sample was taken into Micronics tubes ready for analysis and sufficient aliquots (90 µL) of control brain homogenate prepared for preparation of standards and blanks.

An aliquot (10 µL) of the appropriate acetonitrile stocks was added to the control brain homogenate (to give a final volume of 100 µL) to give the required calibration standards covering the range 1.5-5000 ng/g. Double blank and blank samples were prepared by adding 10 µL of acetonitrile to 90 µL of blank brain homogenate.

Extraction of Plasma and Brain Samples, Standards and Blanks

Each plasma and brain homogenate sample, standard and blank (100 µL) was extracted with an aliquot (300 µL) of acetonitrile (containing 0.1% formic acid and 100 ng/mL of an appropriate internal standard). Double blanks were extracted with an aliquot (300 μL) of acetonitrile containing 0.1% formic acid). All samples, standards and blanks were then vortex mixed and centrifuged (2000 g for 15 min). An aliquot (50 μL) of the resulting supernatant was then taken into a 2 mL 96-deep well plate and diluted with acetonitrile: water (50:50 v/v) (150 μL) ready for analysis by a specific LC-MS/MS method.

Preparation of CSF Samples, Standards and Blanks

Control male Sprague Dawley rat CSF and the study CSF samples were stored at −80° C. until the day of analysis when they were thawed at room temperature. An aliquot (50 μL) of each study sample was taken into Micronics tubes ready for analysis and sufficient aliquots (45 μL) of control CSF prepared for preparation of standards and blanks.

An aliquot (5 μL) of the appropriate acetonitrile stocks was added to the control CSF (to give a final volume of 50 μL) to give the required calibration standards covering the range 1-1000 ng/mL. Double blank and blank samples were prepared by adding 5 μL of acetonitrile to 45 μL of blank CSF.

Extraction of CSF Samples, Standards and Blanks

Each CSF sample, standard and blank (50 μL) was extracted with an aliquot (150 μL) of acetonitrile (containing 0.1% formic acid and 100 ng/mL of an appropriate internal standard). Double blanks were extracted with an aliquot (150 μL) of acetonitrile containing 0.1% formic acid. All samples were then vortex mixed and an aliquot (50 μL) of each was then further diluted in 150 μL of acetonitrile:water (50/50 v/v) in a 2 mL 96-deep well block ready for LC-MS/MS analysis. All samples were then analysed using a Waters Acquity UPLC coupled to a Waters Xevo TQ mass spectrometer.

LC Conditions:

Column. Acquity UPLC BEH C18, 1.7 um, 2.1×50 mm, maintained at 40° C.

Mobile Phase: A=95% Water:5% MeOH containing 0.01M Ammonium acetate

B=5% Water:95% MeOH containing 0.01M Ammonium acetate

Gradient:

| Time (min) | B (%) |
|---|---|
| 0 | 5 |
| 1.2 | 95 |
| 1.5 | 95 |
| 1.7 | 5 |
| 2.0 | 5 |

Flow rate 0.6 mL/min; injection volume 5 μL; autosampler temperature 6° C.

LC flow was diverted to waste for the first 0.3 min of each injection

MS/MS transitions were optimised automatically by Waters QuanOptimise software.

Amyloid Detection

DEA/NaCl Extraction of Aβ Peptides from Rat Brain:

100 ml of chilled 0.2% diethyl amine (DEA) in 50 mM NaCl (pH 10) was freshly prepared and 1 ml/25 mg brain tissue was added to each hemisphere (i.e. 40× brain volume). The brains were immediately homogenized using a Polytron PT 1200 for 1.5 minutes and samples left to incubate on ice for one hour after homogenisation. 3 ml of the homogenate was transferred to a polyallomer tube (Beckman #362333) and spun at 133000×g (55,000 rpm) for 45 min at 4° C. The supernatant was then neutralised to pH 8-8.3 by adding 1/10 volume 0.5M Tris/HCl, pH 6.8. The samples can be used fresh or snap frozen on dry-ice and stored at −80° C. until required for analysis Human/Rat βAmyloid (40) ELISA (Wako Kit)

The Wako Aβ40 ELISA kit (Code No. 294-62501) uses the monoclonal antibody BNT77, raised against epitope Aβ(11-28) and the monoclonal antibody BA27, which specifically detects the C-terminal portion of Aβ40. This kit is used for the quantitative determination of human or rat Aβ(1-40) and also N-terminally truncated Aβ40 species (Aβ(x-40)) in biological matrices such as tissue culture medium, tissue homogenate, CSF and plasma.

For analysis, plasma and brain samples are diluted 1:1 with the standard diluent contained in the kit and CSF samples are diluted 1:8 with the standard diluent contained in the kit. The assay is carried out according to manufacturers instructions and samples are analysed in duplicate. Data is analysed using Microsoft Excel 2003 and statistical analysis is carried out using Genstat $9^{th}$ Edition.

Thus, when Comparative Example 4 was administered at a dose of 10 mg/kg p.o. and plasma, brain and CSF samples were collected 2, 4, 6 and 8 hours post-dose the following concentrations were measured (Table 2):

TABLE 2

Data for Comparative Example 4

| Time (h) | [Pl] (nM) | $^1$[Pl$_u$] (nM) | [Br] (nM) | $^2$[Br$_u$] (nM) | [CSF] (nM) | Br$_{tot}$:Pl$_{tot}$ | Br$_u$:Pl$_u$ | CSF:Pl$_u$ |
|---|---|---|---|---|---|---|---|---|
| 2 | 1257 | 440 | 971 | 65 | 104 | 0.8 | 0.15 | 0.24 |
| 4 | 1162 | 407 | 874 | 59 | 88 | 0.7 | 0.14 | 0.22 |
| 6 | 834 | 292 | 570 | 38 | 63 | 0.7 | 0.13 | 0.22 |
| 8 | 484 | 169 | 368 | 25 | 26 | 0.8 | 0.15 | 0.15 |

$^1$Calculated by multiplying the [Pl] by Pl Fu.
$^2$Calculated by multiplying the [Br] by Br Fu.

From the above study, Comparative Example 4 showed a 59% and 64% reduction of Aβ40 in the brain at 4 and 6 hours respectively; and a 76% and 70% reduction of Aβ40 in the CSF at 4 and 6 hours respectively.

Certain compounds of the present invention have been assessed in vivo in the rat to corroborate the levels of CNS penetration; these data are presented in the tables below.

Surprisingly, it has been found that compounds of the present invention show increased CNS penetration in the rat relative to compounds from WO2009/091016 by any of the aforementioned recognized methods of determining CNS penetration. Thus, the compounds of the present invention may show improved profiles in that they more readily target the site of action, the brain, and therefore may show improved efficacy or efficacy at lower concentrations or doses or decreased peripherally mediated side effects, by way of preferential CNS partitioning, or a combination of any or all of these aspects.

Thus, when Example 8 of the present invention was administered at a dose of 10 mg/kg p.o. and plasma, brain and CSF samples were collected 2, 4, 6 and 8 hours post-dose the following concentrations were measured (Table 3):

TABLE 3

Data for Example 8

| Time (h) | [Pl] (nM) | [1][Pl$_u$] (nM) | [Br] (nM) | [2][Br$_u$] (nM) | [CSF] (nM) | Br$_{tot}$:Pl$_{tot}$ | Br$_u$:Pl$_u$ | CSF:Pl$_u$ |
|---|---|---|---|---|---|---|---|---|
| 2 | 1189 | 124 | 3961 | 87 | 65 | 3.3 | 0.7 | 0.5 |
| 4 | 657 | 68 | 2582 | 57 | 39 | 3.9 | 0.8 | 0.6 |
| 6 | 229 | 24 | 845 | 19 | 12 | 3.7 | 0.8 | 0.5 |
| 8 | 186 | 19 | 709 | 16 | [3]n.q. | 3.8 | 0.8 | [4]n.d. |

[1]Calculated by multiplying the [Pl] by Pl Fu.
[2]Calculated by multiplying the [Br] by Br Fu.
[3]Not quantifiable. Concentrations close to or below the lower limit of quantification and could not be accurately quantified.
[4]Not determined.

From the above study, Example 8 showed a 68% and 72% reduction of Aβ40 in the brain at 4 and 6 hours respectively; and an 82% and 74% reduction of Aβ40 in the CSF at 4 and 6 hours respectively. Thus compounds of the present invention show decreased Pgp efflux relative to previous disclosures whilst demonstrating efficacy in the CNS. The efficacy is thus achieved with lower circulating plasma concentrations.

When Example 1 of the present invention was administered at a dose of 10 mg/kg p.o. and plasma, brain and CSF samples were collected 2, 4, 6 and 8 hours post-dose, the following concentrations were measured (Table 4):

TABLE 4

Data for Example 1

| Time (h) | [Pl] (nM) | [1][Pl$_u$] (nM) | [Br] (nM) | [2][Br$_u$] (nM) | [CSF] (nM) | Br$_{tot}$:Pl$_{tot}$ | Br$_u$:Pl$_u$ | CSF:Pl$_u$ |
|---|---|---|---|---|---|---|---|---|
| 2 | 462 | 23 | 2338 | 30 | 23 | 5.1 | 1.3 | 1.0 |
| 4 | 298 | 15 | 1550 | 20 | 18 | 5.2 | 1.3 | 1.2 |
| 6 | 401 | 20 | 1492 | 19 | 10 | 3.7 | 1.0 | 0.5 |
| 8 | 228 | 11 | 1194 | 16 | 18 | 5.2 | 1.5 | 1.6 |

[1]Calculated by multiplying the [Pl] by Pl Fu.
[2]Calculated by multiplying the [Br] by Br Fu.

From the above study, Example 1 showed a 64% and 70% reduction of Aβ40 in the brain at 4 and 6 hours respectively; and a 80% and 85% reduction of Aβ40 in the CSF at 4 and 6 hours respectively. Thus compounds of the present invention show decreased Pgp efflux relative to previous inventions whilst demonstrating efficacy in the CNS. The efficacy is thus achieved with lower circulating plasma concentrations.

Method For Determination of Plasma Protein Binding (PPB) and Brain Tissue Binding (BTB)

Compound Preparation

Compounds were dissolved in DMSO to give a 1 mg free base/mL solution, before further dilution to 100 μg/mL in acetonitrile (100 μL of 1 mg/mL into 900 μL acetonitrile).

Matrix Preparation

On the morning of dialysis, control male Sprague Dawley rat plasma and brain, previously stored at −80° C. were thawed at room temperature. Plasma was checked for pH and if necessary adjusted to 7.4 with 1M HCl. Plasma was then centrifuged (2000 g for 10 min) and the brains diluted with 2 mL of Phosphate Buffered Saline (pH 7.4) per gram of tissue and homogenised using a mechanical homogeniser. An aliquot (10 μL) of the 100 μg/mL acetonitrile compound solution was then added to 1 mL of plasma and brain homogenate and vortex mixed to give a final compound concentration of 1 μg/mL in matrix.

RED Plate Preparation

The Rapid Equilibrium Dialysis (RED) plate (Thermo Scientific) was prepared in accordance with the manufacturers guidelines i.e. the base plate was soaked in 20% (v/v) ethanol for 10 min and then rinsed twice with deionised water before being allowed to dry. The base plate was then filled with the appropriate number of disposable inserts (n=3 per compound) (Thermo Scientific) and matrix containing 1 μg/mL compound added into the matrix chamber of the inserts (200 μL) and an aliquot (350 μL) of PBS added to the buffer chamber. The plate was then covered with an adhesive and incubated in air at 37° C. for 6 h with 130 rpm agitation.

Sampling

Following the 6 h incubation, the seal was removed and an aliquot (50 μL) taken from the PBS chambers and dispensed into Micronics tubes. Also, an aliquot (50 μL) was removed from the matrix chambers and placed into separate Micronics tubes. Plasma and brain was then matrix matched with 50 μL of drug-free PBS and the PBS samples with 50 μL of the corresponding drug-free matrix, to give equal final compositions and volumes (100 μL).

Sample Analysis

Samples were vortex mixed and an aliquot (300 μL) of acetonitrile containing 0.1% formic acid and 100 ng/mL of an appropriate internal standard added. Samples were then mixed and centrifuged (2000 g for 15 min) and an aliquot of the supernatant (100 μL) removed into a 96-deep well plate and diluted with an equal volume of water ready for analysis by LC-MS/MS. The following data was obtained for the following compounds in the above assay (Table 5).

TABLE 5

| Compound | Rat PPB (%) | Rat Plasma fu | Rat BTB (%) | Rat Brain fu |
|---|---|---|---|---|
| Comparative Example 4 | 65.0 | 0.350 | 93.3 | 0.067 |
| Example 1 | 95.1 | 0.049 | 98.7 | 0.013 |
| Example 8 | 89.6 | 0.104 | 97.8 | 0.022 |

Data represents the Mean of n = 3 replicates
fu = fraction unbound

From the data presented herein above it will be apparent to those skilled in the art that the compounds of Examples 1 and 8 achieve a similar reduction of brain Aβ40 to that of Comparative Example 4, but with a lower plasma concentration and free plasma concentration. This is advantageous and indicates that the compounds of the invention will have similar or better efficacy at lower concentrations than the compounds of WO2009/091016, and consequently will be less likely to cause unwanted peripherally mediated side effects, such as cardiovascular effects, phospholipidosis, liver toxicity, renal toxicity and gastrointestinal toxicity.

Assessment of Effects on QTc Interval in Guinea Pigs

Male Dunkin-Hartley guinea pigs were weighed and anaesthetised using 4% isoflurane in carbogen. Anaesthesia was maintained at 1.5% isoflurane and the animals were kept under anaesthesia for the duration of the study. Xylazine at 2 mg/kg i.m. was administered into the hind limb as a bradycardic agent to enable detection of QTc prolongation by the software.

The carotid artery and jugular vein were cannulated with lines containing heparinised saline and a 3-lead ECG connected and monitored using LabChart Pro software. Animals were allowed to stabilise for 30 minutes after the completion of the surgical procedure, before the initiation of an i.v. vehicle (5% DMSO/90% MilliQ/5% 0.1N HCl) infusion from time zero (infusion rate=0.2 ml/kg/min). At 10 mins, an arterial blood sample was collected for PK analysis (150u1; all collection syringes were heparinised). At 12 mins, drug infusion was started @ 2.0 mg/kg/10 min i.v. The dose was increased to 6.0 mg/kg/10 min, then 20 mg/kg/10 min i.v., with a 10 minutes infusion period and two minutes blood sampling at each dose. After the final dose, a blood sample was taken and a second vehicle infusion initiated. Eight minutes later a terminal blood sample was collected for plasma PK analysis and the animal killed by a Schedule 1 method.

QTc (Bazett's) changes were analysed using LabChart Pro software. QTc was unchanged up to the highest dose/concentration tested, which corresponded to an unbound plasma concentration of 9503 nM for Example 8 and 296 nM for Example 1.

Assessment of Effects on QTc Interval in Beagle Dogs

Male beagle dogs were weighed and injected with sodium thiopental for induction of anesthesia. Anaesthesia was maintained with mixture of 1-1.5% isoflurane and oxygen and the animals were kept under artificial respiration and anesthesia using isoflurane for the duration of the study.

The carotid artery and saphenous vein were cannulated with lines containing heparinised saline and a LII ECG connected and monitored using polygraph system. Animals were allowed to stabilise for 30 minutes before the infusion of compound solution and the infusion via cannula was started from time zero with 1 mg/kg/10 min. The dose was increased to 3 mg/kg/10 min, then 10 mg/kg/10 min. An arterial blood sample was collected after every dosing for PK analysis.

QTc was unchanged up to the highest dose/concentration tested, which corresponded to an unbound plasma concentration of 4128 nM for Example 8 and 1329 nM for Example 1.

Next, methods for preparing the compound of the formula (I) or a pharmaceutically acceptable salt thereof according to the present invention will be described.

A. General Preparation Method A:

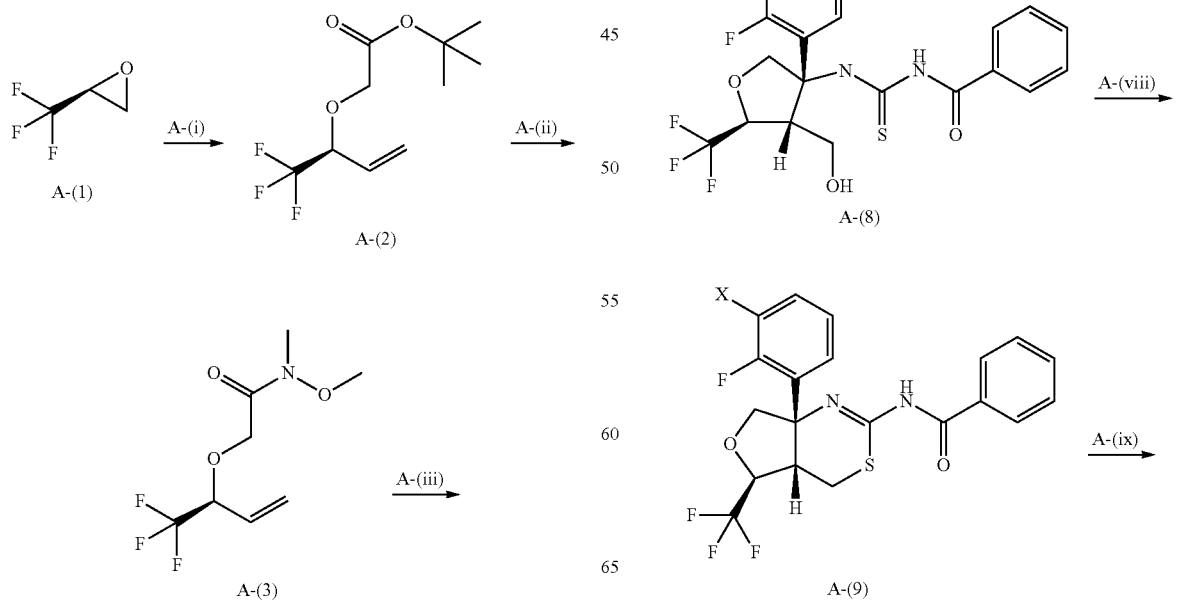

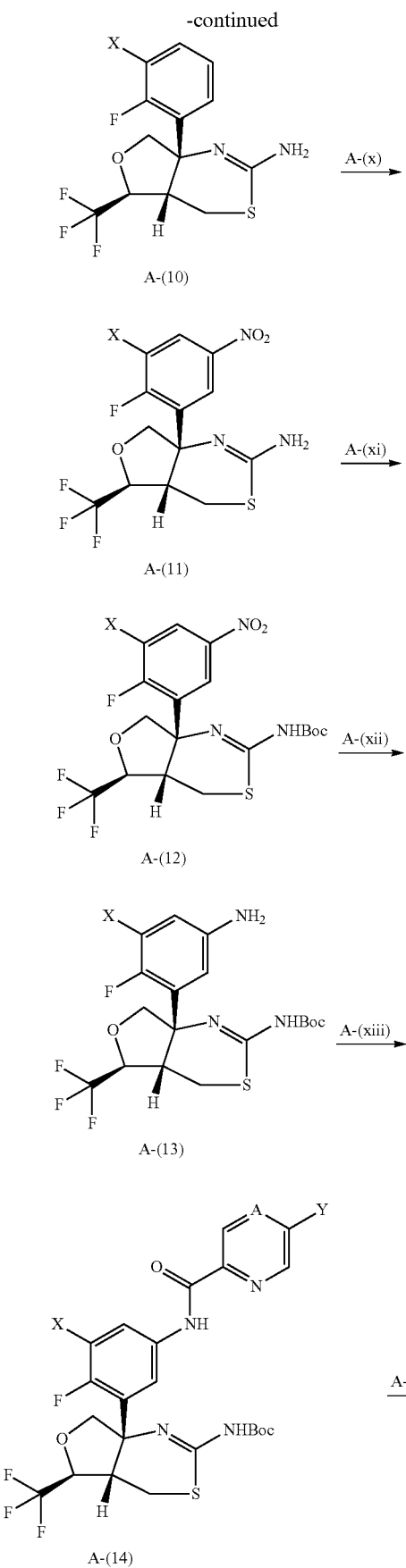

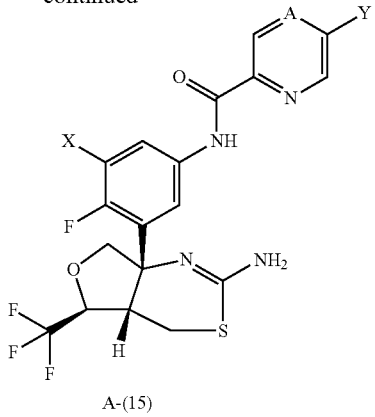

A-(15)

In the formula, X, Y and A are as defined above.

General Preparation Method A is a method for preparing a compound A-(15) which corresponds to compound (I) according to the present invention from a compound A-(1) as a raw material through multiple steps of Step A-(i) to Step A-(xiv).

The compound A-(1) is commercially available. Step A-(i): This step is a step of obtaining a compound A-(2) by opening the epoxide A-(1) with a sulfonium ylide to generate an intermediate allylic alkoxide which is then alkylated to give the compound A-(2). Those skilled in the art will appreciate that this transformation can be conducted in one pot or as two individual reactions. Those skilled in the art will appreciate the benefits and drawbacks of a one pot reaction compared to conducting two separate reactions and choose the best method for their requirements accordingly.

Specifically, the epoxide A-(1) can be opened by the anion of trimethylsulfonium iodide and resultant loss of dimethylsulfide to give the corresponding allylic alkoxide. Trimethylsulfonium iodide can be deprotonated with a suitable base, for example butyl lithium. The solvent used in the reaction is not particularly limited insofar as it does not interfere with the reaction. Examples of suitable solvents include THF. Those skilled in the art will appreciate that the word solvent in this instance is used to denote the liquid in which the reaction is effected and that the reagents may not be dissolved. Preferably the reaction should be conducted below room temperature, preferably −30-20° C. Upon addition the reaction may be warmed to room temperature to facilitate reaction. The reaction time is not particularly limited and is usually 5 minutes to 24 hours, preferably 1-6 hours.

Those skilled in the art will appreciate that the alkoxide generated from this reaction can be reacted with an alkylating agent directly, such as tert-butyl bromoacetate, and that this reaction may proceed with or without additional solvents. If additional solvents are required to facilitate reaction, then solvents such as DMF or NMP are suitable. The reaction temperature is not particularly limited. Suitable reaction temperatures include room temperature to 80° C., preferably room temperature. The reaction time is not particularly limited and is usually 5 minutes to 1 week, preferably 1-48 hours.

Those skilled in the art will appreciate that the intermediate alkoxide could be quenched, isolated and purified then subjected to independent alkylation conditions. This reaction can be performed under the same conditions as those usually used in O-alkylation reaction of an alcohol compound (such as the conditions described in Tetrahedron Lett. 46 (2005) 45, 7751-7755). In this reaction, the compound A-(2) can be obtained by adding a base such as sodium hydride to a solution of the intermediate alcohol in THF to prepare an alkoxide, and then reacting the alkoxide with the tert-butyl bromoacetate, for example. The solvent used in the reaction is not particularly limited insofar as it does not inhibit the reaction and allows the starting material to be dissolved therein to a certain extent. Examples of the solvent include solvents such as THF, DMF and dimethyl sulfoxide. The reaction can be performed by causing 1 to 3 equivalents of an appropriate base to act in the presence of such a solvent. Examples of the base used include sodium hydride, potassium hydride and t-butoxypotassium. The reaction time is not particularly limited and is usually 0.5 to 72 hours, and preferably 0.5 to 12 hours. The reaction temperature is usually −20° C. to 50° C.

A more preferable result such as an improved yield may be achieved by adding a salt such as tetrabutylammonium iodide in this reaction.

Step A-(ii):

This step is a two step sequential reaction to obtain compound A-(3) from compound A-(2) by deprotecting the ester group then forming a Weinreb amide.

Specifically, the tert-butyl ester of compound A-(2) can be deprotected under the same conditions as those generally used in deprotection of a tert-butyl ester compound (such as the conditions described in a document such as T. W. Greene and P. G. M. Wuts, "Protective Groups in Organic Chemistry, Third Edition", John Wiley & Sons (1999), p. 404-408). In this reaction, the compound A-(2) can be reacted with an appropriate acid in a suitable solvent, such as formic acid, as solvent and acid, for example. The solvent used in the reaction is not particularly limited insofar as it does not inhibit the reaction and allows the starting material to be dissolved therein to a certain extent. The reaction time is not particularly limited and is usually 0.5 to 72 hours, and preferably 0.5 to 24 hours. The reaction temperature is usually ice-cold temperature to 60° C.

The intermediate acid can then be transformed to the Weinreb amide (Tetrahedron Lett. 1981, 22, 3815) by reaction of N,O-dimethylhydroxylamine hydrochloride under standard amide formation conditions, ie by condensing the intermediate acid with N,O-dimethylhydroxylamine hydrochloride using a condensing agent. Alternatively, this step is a step of obtaining a compound A-(3) by condensing the intermediate acid with N,O-dimethylhydroxylamine hydrochloride by acylation reaction.

The condensation reaction of the intermediate acid with N,O-dimethylhydroxylamine hydrochloride using a condensing agent can be performed under the same conditions as those usually used and described in the following documents. Examples of the known method include those in Rosowsky et al.; J. Med. Chem., 34 (1), 227-234 (1991), Brzostwska et al.; Heterocycles, 32 (10), 1968-1972 (1991), and Romero et al.; J. Med. Chem., 37 (7), 998-1014 (1994).

The N,O-dimethylhydroxylamine hydrochloride may be a free form or a salt.

The solvent in this reaction is not particularly limited insofar as it does not inhibit the reaction. Examples of the solvent include tetrahydrofuran, 1,4-dioxane, ethyl acetate, methyl acetate, dichloromethane, chloroform, N,N-dimethylformamide, toluene, acetonitrile and xylene. Examples of the condensing agent include CDI (N,N'-carbonyldiimidazole), Bop (1H-1,2,3-benzotriazol-1-yloxy(tri(dimethylamino))phosphonium hexafluorophosphate), WSC (1-ethyl-3-(3-dimethylaminopropyl)carbodiimide hydrochloride), DCC (N,N-dicyclohexylcarbodiimide), diethylphosphoryl cyanide, PyBOP (benzotriazol-1-yloxytris(pyrrolidino)phosphonium hexafluorophosphate) and EDC.HCl (1-ethyl-3-(3-dimethylaminopropyl)carbodiimide hydrochloride). Suitable conditions include an agent to activate the acid, such as N,N'-carbonyl diimidazole. One equivalent to a large excess of N,O-dimethylhydroxylamine hydrochloride is used with respect to the intermediate acid. One equivalent to a large excess of an organic base such as triethylamine may be added where necessary.

The reaction time is not particularly limited and is usually 0.5 to 72 hours, and preferably 0.5 to 24 hours. The reaction temperature varies according to the raw material used, the solvent and the like and is not particularly limited. Ice-cold temperature to solvent reflux temperature is acceptable, ice cold to room temperature is preferable.

Step A-(iii):

This step is a step of obtaining a compound A-(4) by reaction of an organometallic (aryllithium reagent or a Grignard reagent) reagent with compound A-(3) as described in Tetrahedron Lett. 1981, 22, 3815.

The reaction in this step can be performed under the same conditions as those described in Tetrahedron Lett. 1981, 22, 3815, for example.

The aryllithium reagent (including heterocyclic) or the Grignard reagent (including heterocyclic) can be prepared by a method known to a person skilled in the art. Specifically, the corresponding phenyl lithium reagent or phenyl magnesium (Grignard) reagent can be prepared by halogen-metal exchange between an aryl halide compound and a commercially available organometallic reagent such as an alkyllithium reagent such as n-, sec- or tert-butyllithium or a Grignard reagent such as isopropylmagnesium bromide, or metallic magnesium, for example.

The solvent used in this step varies according to the starting material and the reagent used, and is not particularly limited insofar as it does not inhibit the reaction, allows the starting material to be dissolved therein to a certain extent, and is always inert during the reaction. Preferable examples of the solvent include organic solvents such as diethyl ether, tetrahydrofuran, 1,4-dioxane, 1,2-dimethoxyethane, benzene and toluene, and mixed solvents thereof. The reaction time is not particularly limited and is usually 0.1 to 48 hours, and preferably 0.1 to 12 hours. The reaction temperature varies according to the starting material, the reagent used and the like, and is preferably maintained to be low, for example, at −78--60° C.

Step A-(iv):

This step is a step of obtaining a compound A-(5) by oximation of the compound A-(4).

The reaction in this step can be performed under the same conditions as those usually used in oximation reaction of a carbonyl compound such as the conditions described in Org. Lett. 9 (2007) 5, 753-756, Tetrahedron: Asymmetry 5 (1994) 6, 1018-1028 and Tetrahedron 54 (1998) 22, 5868-5882.

Specifically, the compound A-(5) can be obtained by reacting the compound A-(4) with hydroxylamine or a hydroxylamine salt (such as hydroxylamine hydrochloride or hydroxylamine sulfate) in the presence of a base or in the absence of a base, for example.

The solvent used in this reaction is not particularly limited insofar as it does not inhibit the reaction. Preferable examples of the solvent include organic solvents such as ethanol, methanol, tetrahydrofuran, 1,4-dioxane, 1,2-dimethoxyethane and dichloromethane, and mixtures of these solvents and water. Examples of the base used include sodium acetate, pyridine, sodium hydroxide, cesium hydroxide, barium hydroxide and 2,6-lutidine. The reaction time is not particularly limited and is usually 5 minutes to 24 hours, and preferably 5 minutes to 12 hours. The reaction temperature is usually −20° C. to solvent reflux temperature, and more preferably 0° C. to solvent reflux temperature.

Step A-(v):

This step is a step of obtaining a compound A-(6) by a thermal intramolecular cycloaddition of the alkenyl oxime A-(5).

The reaction is conducted in the presence of an additive, for example hydroquinone.

The solvent used in this reaction is not particularly limited insofar as it does not inhibit the reaction. Suitable reaction solvents include high boiling solvents such as xylenes. The reaction temperature is not particularly limited and is usually 80-200° C. or solvent reflux temperature. The reaction time is not particularly limited and is usually 0.5 to 48 hours, and preferably 0.5 to 24 hours.

Step A-(vi):

This step is a step of obtaining a compound A-(7) by subjecting the compound A-(6) to reductive cleavage reaction of the N—O bond.

The reductive cleavage reaction of the N—O bond can be performed under the conditions using zinc-acetic acid, a metal catalyst such as hydrogen-platinum oxide, or lithium aluminum hydride, for example.

The reaction using zinc such as zinc-acetic acid can be performed under the same conditions as those described in J. Org. Chem. 2003, 68, 1207-1215 and Org. Lett. 7 (2005) 25, 5741-5742, for example. Examples of the acid used include acetic acid, formic acid and hydrochloric acid. The solvent used in the reaction is not particularly limited insofar as it does not inhibit the reaction and allows the starting material to be dissolved therein to a certain extent. Examples of the solvent include methanol, ethanol, 1,4-dioxane, THF and water. The above acid may also be used as a solvent. The reaction temperature is usually −20° C. to solvent reflux temperature, and preferably ice-cold temperature to solvent reflux temperature. The reaction time is not particularly limited and is usually 5 minutes to 48 hours, and preferably 5 minutes to 24 hours.

The reaction using a metal catalyst such as hydrogen-platinum oxide can be performed under the same conditions as those described in Tetrahedron: Asymmetry 5 (1994) 6, 1018-1028 and Tetrahedron, Vol. 53, No. 16, pp 5752-5746, 1997, for example. The compound A-(7) can be obtained by hydrogenating the compound A-(6) using platinum oxide as a catalyst in a solvent such as methanol, for example.

The reaction using lithium aluminum hydride can be performed under the same conditions as those described in Bull. Chem. Soc. Jpn., 66, 2730-2737 (1993), for example. The compound A-(7) can be obtained by reducing the compound A-(6) using lithium aluminum hydride in a solvent such as ether, for example.

Step A-(vii):

This step is a step of obtaining a compound A-(8) from the compound A-(7). The thiourea derivative A-(8) can be obtained from the compound A-(7) by a method known to a person skilled in the art.

The compound A-(8) can be obtained in this step by reacting the compound A-(7) with benzoyl isothiocyanate in a solvent such as dichloromethane or toluene. This reaction can be performed under the same conditions as those described in J. Med. Chem. 1990, 33, 2393-2407, for example. The solvent used in the reaction is not particularly limited insofar as it does not inhibit the reaction and allows the starting material to be dissolved therein to a certain extent. Examples of the solvent include dichloromethane, chloroform, toluene, 1,4-dioxane and THF. The reaction temperature is usually −20° C. to solvent reflux temperature, and preferably ice-cold temperature to solvent reflux temperature. The reaction time is not particularly limited and is usually 5 minutes to 48 hours, and preferably 5 minutes to 24 hours.

Step A-(viii):

This step is a method of obtaining a compound A-(9) by cyclizing the compound A-(8).

In this reaction, the compound A-(8) can be cyclized under various conditions to obtain the compound A-(9) by activating the alcohol of compound A-(8).

For example, the compound A-(9) can be obtained in this reaction by heating the compound A-(8) in a solvent such as methanol in the presence of an acid such as concentrated hydrochloric acid, for example. The solvent used in the reaction is not particularly limited insofar as it does not inhibit the reaction and allows the starting material to be dissolved therein to a certain extent. Examples of the solvent include solvents such as methanol, ethanol, 1-propanol and water, mixed solvents thereof, and acids used as a solvent. The reaction can be performed by using one equivalent to a large excess of an appropriate acid to act in the presence or absence of such a solvent. Examples of the acid used include concentrated hydrochloric acid, hydrobromic acid, sulfuric acid, trifluoroacetic acid, methanesulfonic acid, trifluoromethanesulfonic acid and mixtures thereof. The reaction time is not particularly limited and is usually 0.5 to 72 hours, and preferably 0.5 to 24 hours. The reaction temperature is usually ice-cold temperature to solvent reflux temperature.

Alternatively, the compound A-(9) can be obtained by reacting the compound A-(8) with trifluoromethanesulfonic anhydride in a solvent such as dichloromethane in the presence of a base such as pyridine. The solvent used in the reaction is not particularly limited insofar as it does not inhibit the reaction and allows the starting material to be dissolved therein to a certain extent. Those skilled in the art will appreciate that a solvent is not always required and the reaction may also be conducted in the absence of a solvent, for example when the base is pyridine. Examples of the solvent include solvents such as dichloromethane, chloroform, 1,2-dichloroethane, THF, 1,2-dimethoxyethane and toluene, and mixed solvents thereof. The reaction can be performed using 1 to 20 equivalents of an appropriate base in such a solvent. Examples of the base used include pyridine, 2,6-lutidine, sodium carbonate, potassium carbonate and mixtures thereof. The reaction time is not particularly limited and is usually 0.5 to 24 hours, and preferably 0.5 to 12 hours. The reaction temperature is usually −78° C. to room temperature.

Step A-(ix):

This step is a method of obtaining the compound A-(10) by deprotecting the protecting group of the compound A-(9). The compound A-(10) can be obtained under deprotection conditions known to a person skilled in the art.

When the protecting group is a benzoyl group, the compound A-(10) can be obtained in this reaction by heating the compound A-(9) in a solvent such as methanol in the presence of a base such as DBU, for example. This reaction can be performed under the same conditions as those described in Synth. Commun. 32 (2), 265-272 (2002), for example. The solvent used in the reaction is not particularly limited insofar as it does not inhibit the reaction and allows the starting material to be dissolved therein to a certain extent. Examples of the solvent include solvents such as methanol, ethanol and 1-propanol. The reaction can be performed using 1 to 20 equivalents of an appropriate base in such a solvent. Examples of the base used include DBU. The reaction time is not particularly limited and is usually 0.5 to 24 hours, and preferably 0.5 to 12 hours. The reaction temperature is usually room temperature to solvent reflux temperature.

Alternatively, compound A-(10) can be obtained in this reaction by heating compound A-(9) with an inorganic base such as potassium carbonate, for example. The solvent used in the reaction is not particularly limited insofar as it does not inhibit the reaction and allows the starting material to be dissolved therein to a certain extent. Examples of the solvent include solvents such as methanol, ethanol and 1-propanol. The reaction can be performed using 1 to 20 equivalents of an appropriate base in such a solvent, and preferably a slight excess is used. Examples of the base used include potassium carbonate. The reaction time is not particularly limited and is usually 0.5 to 24 hours, and preferably 0.5 to 12 hours. The reaction temperature is usually room temperature to solvent reflux temperature, and preferably 50-100° C. Those skilled in the art will appreciate that the selected solvent will limit the reaction temperature by its reflux temperature. Examples of suitable solvents include refluxing methanol.

Step A-(x):

This step is a step of obtaining the compound A-(11) by nitration reaction of the compound A-(10). In this nitration reaction, the compound A-(11) can be obtained from the compound A-(10) by a method known to a person skilled in the art. Examples of the nitrating agent used in the reaction include potassium nitrate/concentrated sulfuric acid, fuming nitric acid/concentrated sulfuric acid and fuming nitric acid/acetic anhydride. Suitable solvents for the reaction include trifluoroacetic acid. The reaction temperature is not particularly limited and is usually −20° C. to room temperature, and preferable reaction temperatures include 0-10° C.

Step A-(xi):

This step is a step of obtaining a compound A-(12) by t-butoxycarbonylation of the amino group of the compound A-(11).

The reaction can be performed under the same conditions as those generally used in t-butoxycarbonylation of an amino compound such as the conditions described in a document such as T. W. Greene and P. G. M. Wuts, "Protective Groups in Organic Chemistry, Third Edition", John Wiley & Sons (1999), P. 518-525. The compound A-(12) can be obtained by reacting the compound A-(11) with di-tert-butyl dicarbonate using in a solvent such as tetrahydrofuran, for example. Alternative solvents include acetonitrile and DMF. Those skilled in the art will appreciate that a base may also be added to the reaction mixture, although is not essential. Suitable examples of a base include, but are not limited to triethylamine and diisopropylethylamine. The reaction temperature is not particularly limited and is usually to room temperature to reflux, and preferably room temperature to 60° C.

Step A-(xii):

This step is a step of obtaining a compound A-(13) from the compound A-(12).

The compound A-(13) is synthesized by reducing the nitro compound A-(12) by a synthesis method known to a person skilled in the art. Examples of the method include reduction by catalytic hydrogenation using a noble metal catalyst such as Raney nickel, palladium, ruthenium, rhodium or platinum. Other reducing reagents include tin chloride, for example. Examples of the solvent include alcoholic solvents such as methanol, ethanol and 1-propanol, preferably ethanol. The reaction time is not particularly limited and is usually 0.5 to 24 hours, and preferably 0.5 to 18 hours. The reaction temperature is usually room temperature. Alternative reduction reaction conditions include reaction with iron with an additive such as ammonium chloride or hydrochloric acid, in an alcoholic solvent such as ethanol, at an appropriate reaction temperature, for example 65° C.

Step A-(xiii):

This is a step of obtaining a compound A-(14) from the compound A-(13) by condensing compound A-(13) with a carboxylic acid and a condensing agent. The condensation reaction can be performed under the same conditions as those usually used and described in the following documents. Examples of the known method include those in Rosowsky et al.; J. Med. Chem., 34 (1), 227-234 (1991), Brzostwska et al.; Heterocycles, 32 (10), 1968-1972 (1991), and Romero et al.; J. Med. Chem., 37 (7), 998-1014 (1994).

The compound A-(13) may be a free form or a salt.

The solvent in this reaction is not particularly limited insofar as it does not inhibit the reaction. Examples of the solvent include tetrahydrofuran, 1,4-dioxane, ethyl acetate, methyl acetate, dichloromethane, chloroform, N,N-dimethylformamide, toluene, acetonitrile and xylene. Examples of the condensing agent include CDI (N,N'-carbonyldiimidazole), Bop (1H-1,2,3-benzotriazol-1-yloxy(tri(dimethylamino))phosphonium hexafluorophosphate), WSC (1-ethyl-3-(3-dimethylaminopropyl)carbodiimide hydrochloride), DCC(N,N-dicyclohexylcarbodiimide), diethylphosphoryl cyanide, PyBOP (benzotriazol-1-yloxytri(pyrrolidino)phosphonium hexafluorophosphate) and EDC.HCl (1-ethyl-3-(3-dimethylaminopropyl)carbodiimide hydrochloride). Suitable conditions include an agent to activate the acid, such as N,N'-carbonyl diimidazole. One equivalent to a large excess of the acid may be used with respect to the compound A-(13). One equivalent to a large excess of an organic base such as triethylamine or N,N-diisopropylethylamine may be added where necessary.

The reaction time is not particularly limited and is usually 0.5 to 72 hours, and preferably 0.5 to 24 hours. The reaction temperature varies according to the raw material used, the solvent and the like and is not particularly limited. Ice-cold temperature to solvent reflux temperature is acceptable, ice cold to room temperature is preferable.

Alternatively, the compound A-(14) can be obtained by converting the desired carboxylic acid to the corresponding acid chloride and then reacting the acid chloride with the compound A-(13). The acid chloride can be synthesized by a means known to a person skilled in the art. For example the desired carboxylic acid may converted to the corresponding acid chloride by reaction with thionyl chloride in the presence or absence of a solvent, for example dichloromethane, N,N'-dimethylimidazoline-2-one, NMP or DMF. One to two equivalents or a large excess of thionyl chloride may be used with respect to the desired carboxylic acid. The reaction temperature is −30° C. to reflux, and preferably −10° C. to room temperature. The acid chloride may also be formed by treating the acid with oxalyl chloride in a solvent such as dichloromethane in the presence of DMF. The reaction temperature is −30° C. to room temperature, and preferably −10° C. to room temperature Alternatively, the compound A-(14) can be obtained by converting the desired carboxylic acid to a mixed acid anhydride and then reacting the mixed acid anhydride with the compound A-(13). The mixed acid anhydride can be synthesized by a means known to a person skilled in the art. The synthesis is performed by reacting the desired carboxylic acid with a chloroformate such as ethyl chloroformate in the presence of a base such as triethylamine, for example. One to two equivalents of the chloroformate and the base are used with respect to the desired carboxylic acid. The reaction temperature is −30° C. to room temperature, and preferably −20° C. to room temperature.

The step of condensing the mixed acid anhydride with the compound 1-(13) is performed by reacting the mixed acid anhydride with the compound 1-(13) in a solvent such as dichloromethane, tetrahydrofuran or N,N-dimethylformamide, for example. One equivalent to a large excess of the desired carboxylic acid is used with respect to the compound A-(13).

The reaction time is not particularly limited and is usually 0.5 to 48 hours, and preferably 0.5 to 12 hours. The reaction temperature is −20° C. to 50° C., and preferably −20° C. to room temperature.

Alternatively, the compound A-(14) can be obtained by converting the desired carboxylic acid to an active ester and then reacting the active ester with the compound A-(13). The step of obtaining the active ester is performed by reacting the desired carboxylic acid with an active ester synthesis reagent in a solvent such as 1,4-dioxane, tetrahydrofuran or N,N-dimethylformamide in the presence of a condensing agent such as DCC, for example. Examples of the active ester synthesis reagent include N-hydroxysuccinimide. One to 1.5 equivalents of the active ester synthesis reagent and the condensing agent are used with respect to the compound A-(13). The reaction time is not particularly limited and is usually 0.5 to 48 hours, and preferably 0.5 to 24 hours.

The reaction temperature is −20° C. to 50° C., and preferably −20° C. to room temperature.

The step of condensing the active ester with the compound A-(13) is performed by reacting the active ester with the compound A-(13) in a solvent such as dichloromethane, tetrahydrofuran or N,N-dimethylformamide, for example. One equivalent to a large excess of the active ester is used with respect to the compound A-(13). The reaction time is not particularly limited and is usually 0.5 to 48 hours, and preferably 0.5 to 24 hours. The reaction temperature is −20° C. to 50° C., and preferably −20° C. to room temperature.

Step A-(xiv):

This step is a step of obtaining the compound A-(15) by deprotection of the t-butoxycarbonyl group of the compound A-(14).

The reaction can be performed under the same conditions as those generally used in deprotection reaction of a t-butoxycarbonyl group such as the conditions described in a document such as T. W. Greene and P. G. M. Wuts, "Protective Groups in Organic Chemistry, Third Edition", John Wiley & Sons (1999), P. 518-525. The compound A-(15) can be obtained by reacting the compound I-(14) with a strong acid, for example trifluoroacetic acid in the presence or absence of a solvent. Suitable solvents include dichloromethane. Alternative acids include hydrochloric acid in suitable solvents, such as dichloromethane or dioxane, for example.

The reaction temperature is normally ice cold to 80° C., preferably room temperature. The reaction time is not particularly limited and is usually 5 minutes to 48 hours, and preferably 5 minutes to 12 hours.

B. General Preparation Method B:

In the formula, X, Y and A are as defined above.

General Preparation Method B is an alternative method for preparing a compound A-(15) which corresponds to compound (I) according to the present invention from a compound A-(11) as a raw material through multiple steps of Step B-(i) to Step B-(ii).

The compound A-(11) may be prepared as described in General Preparation Method A or the examples.

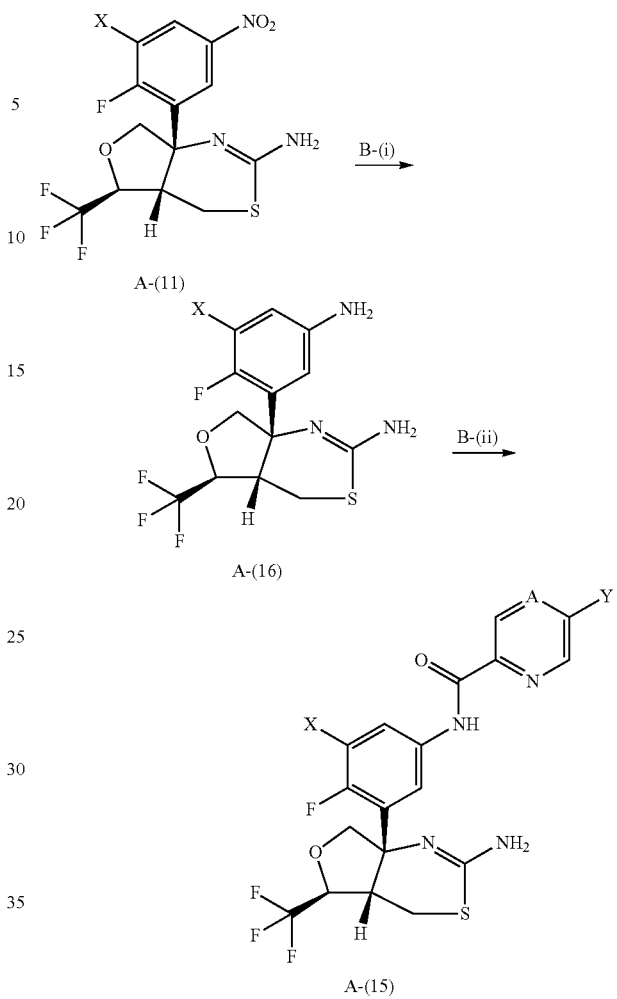

Step B-(i):

This step is a step of obtaining a compound A-(16) from the compound A-(11).

The compound A-(16) is synthesized by reducing the nitro compound A-(11) by a synthesis method known to a person skilled in the art. Examples of the method include reduction by catalytic hydrogenation using a noble metal catalyst such as Raney nickel, palladium, ruthenium, rhodium or platinum. Other reducing reagents include tin chloride, for example. Examples of the solvent include alcoholic solvents such as methanol, ethanol and 1-propanol, preferably ethanol. The reaction time is not particularly limited and is usually 0.5 to 24 hours, and preferably 0.5 to 18 hours. The reaction temperature is usually room temperature. Alternative reduction reaction conditions include reaction with iron with an additive such as ammonium chloride or hydrochloric acid, in an alcoholic solvent such as ethanol, at an appropriate reaction temperature, for example 65° C.

Step B-(ii):

This is a step of obtaining a compound A-(15) from the compound A-(16) by condensing compound A-(13) with a carboxylic acid and a condensing agent. The condensation reaction can be performed under the same conditions as those usually used and described in the following documents. Examples of the known method include those in Rosowsky et al.; J. Med. Chem., 34 (1), 227-234 (1991), Brzostwska et al.;

Heterocycles, 32 (10), 1968-1972 (1991), and Romero et al.; J. Med. Chem., 37 (7), 998-1014 (1994).

The compound A-(15) can be obtained by converting the desired carboxylic acid to the corresponding acid chloride and then reacting the acid chloride with the compound A-(16). The acid chloride can be synthesized by a means known to a person skilled in the art. For example the desired carboxylic acid may converted to the corresponding acid chloride by reaction with thionyl chloride in the presence or absence of a solvent, for example dichloromethane, N,N'-dimethylimidazoline-2-one, NMP or DMF. One to two equivalents or a large excess of thionyl chloride may be used with respect to the desired carboxylic acid. Those skilled in the art will appreciate that the choice of reaction conditions employed may affect the outcome of the reaction, for example the conditions may affect whether the acid chloride reacts with the aniline or the isothiourea moieties. Those skilled in the art will appreciate that the reaction of thionyl chloride with a carboxylic acid results in the concomitant formation of 1 equivalent of hydrochloric acid in addition to the formation of the desired acid chloride. Those skilled in the art will appreciate that the current conditions do not employ a method of removing the thus formed hydrochloric acid. The hydrochloric acid formed in this reaction may or may not affect the selectivity of the reaction which may or may not result in a beneficial outcome. The reaction time is not particularly limited and is usually 0.5 to 48 hours, and preferably 0.5 to 12 hours. The reaction temperature is −30° C. to reflux, and preferably −10° C. to room temperature. The acid chloride may also be formed by treating the acid with oxalyl chloride in a solvent such as dichloromethane in the presence of DMF. The reaction temperature is −30° C. to room temperature, and preferably −10° C. to room temperature.

C. General Preparation Method C:

General Preparation Method C is an alternative method for preparing a compound A-(2) which is a synthetic intermediate of the compound (I) according to the present invention from a compound A-(17) as a raw material through Step C-(i).

The compound A-(17) is commercially available.

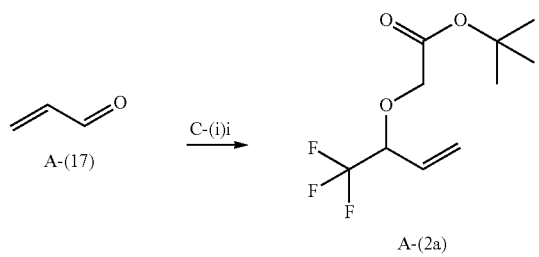

Step i:

This step is a step of obtaining a compound A-(2a) from A-(17) by adding a trifluoromethyl anion to the compound A-(17) to generate an intermediate allylic alkoxide or intermediate trimethylsilyl ether which is then alkylated to give the compound A-(2a). Those skilled in the art will appreciate that this transformation can be conducted in one pot or as two individual reactions. Those skilled in the art will appreciate the benefits and drawbacks of a one pot reaction compared to conducting two separate reactions and choose the best method for their requirements accordingly.

Specifically, acrolein A-(17) can react with a trifluoromethyl anion which can be generated by the action of fluoride on reagents such as (trifluoromethyl)trimethylsilane to generate the corresponding allylic alkoxide or allylic timethylsilyl ether. The solvent used in the reaction is not particularly limited insofar as it does not interfere with the reaction. Examples of suitable solvents include THF. Acceptable temperature ranges for the reaction include −10° C. to solvent reflux, preferably below room temperature. Those skilled in the art will appreciate that certain chemical reactions can be exothermic and that control measures should be put in place to control these exotherms. Those skilled in the art will also appreciate that the reaction exotherm may be controlled by allowing the solvent to reflux. Suitable precursors to generate trifluoromethyl anion include, but are not limited to, (trifluoromethyl)trimethylsilane (Rupert's reagent, Chem Rev 1997, 97, 757) and suitable fluoride sources include, but are not limited to, tetrabutylammonium fluoride (TBAF), tetrabutylammonium difluorotriphenylsilicate (TBAT) and caesium fluoride. Although the initial reaction temperature may be below room temperature it is acceptable to allow the reaction temperature to reach solvent reflux during the course of the reaction to facilitate reaction. The reaction time is not particularly limited and is usually 5 minutes to 24 hours, preferably 1-6 hours.

Those skilled in the art will appreciate that the alkoxide generated from this reaction can be reacted with an alkylating agent directly, such as tert-butyl bromoacetate, and that this reaction may proceed with or without additional solvents. If additional solvents are required to facilitate reaction, then solvents such as DMF or NMP are suitable. The reaction temperature is not particularly limited. Suitable reaction temperatures include room temperature to 80° C., preferably room temperature. The reaction time is not particularly limited and is usually 5 minutes to 1 week, preferably 1-48 hours. Alternatively, the alkylation reaction can be conducted under phase transfer conditions, for example by adding an aqueous base, for example aqueous sodium hydroxide. Those skilled in the art will appreciate that when these conditions are applied the use of a phase transfer catalyst is required. Suitable phase transfer catalysts include, but are not limited to, tetrabutylammonium hydrogen sulfate.

Those skilled in the art will appreciate that the intermediate alkoxide could be quenched, isolated and purified then subjected to independent alkylation conditions. This reaction can be performed under the same conditions as those usually used in O-alkylation reaction of an alcohol compound (such as the conditions described in Tetrahedron Lett. 46 (2005) 45, 7751-7755). In this reaction, the compound A-(2a) can be obtained by adding a base such as sodium hydride to a solution of the intermediate alcohol in THF to prepare an alkoxide, and then reacting the alkoxide with the tert-butyl bromoacetate, for example. The solvent used in the reaction is not particularly limited insofar as it does not inhibit the reaction and allows the starting material to be dissolved therein to a certain extent. Examples of the solvent include solvents such as THF, DMF and dimethyl sulfoxide. The reaction can be performed by causing 1 to 3 equivalents of an appropriate base to act in the presence of such a solvent. Examples of the base used include sodium hydride, potassium hydride and t-butoxypotassium. The reaction time is not particularly limited and is usually 0.5 to 72 hours, and preferably 0.5 to 12 hours. The reaction temperature is usually −20° C. to 50° C.

A more preferable result such as an improved yield may be achieved by adding a salt such as tetrabutylammonium iodide in this reaction.

Those skilled in the art will appreciate that this reaction generates a new chiral centre in the compound A-(2a) and that compound A-(2a) is the same as compound A-(2) except that compound A-(2) is enantiomerically pure whereas compound A-(2a) is racemic. It will be appreciated by those skilled in the art the enantiomerically pure compound A-(2) and the racemic compound A-(2a) are indistinguishable by analytical techniques such as NMR and liquid chromatography, however they are distinguishable by chiral HPLC. Those skilled in the art will appreciate that the most appropriate methods to obtain the desired enantiomer from the compound A-(2a) or a more advanced synthetic intermediate or final compound. Appropriate methods and appropriate stages of enantiomeric purification include those as detailed in the examples.

In a further aspect, the present invention provides a process of preparing a compound of formula (I), which comprises reacting a compound of formula A-(16), wherein X is defined in formula (I), with a compound of formula (II) wherein A and Y are as defined in formula (I), or a $C_{1-6}$ alkyl ester, acid anhydride or acid halide thereof, to yield a compound of formula (I), and optionally converting the compound to a further compound of formula (I) or forming a pharmaceutically acceptable salt thereof

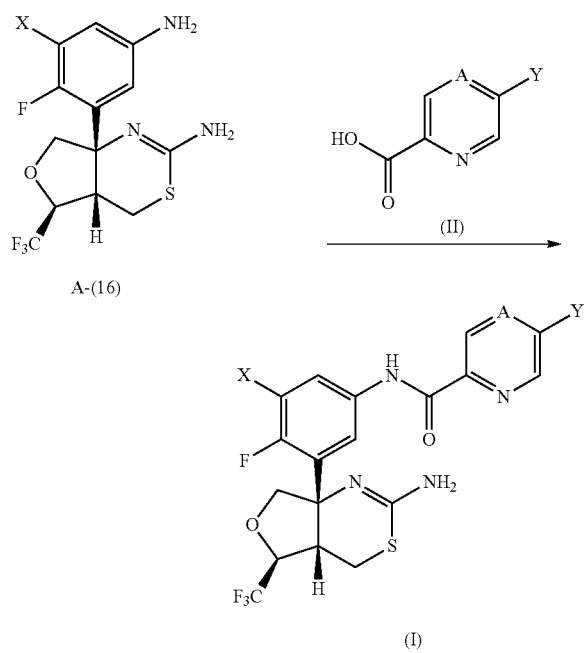

The reaction of A-(16) and (II) may conveniently be conducted in a solvent (such as tetrahydrofuran, 1,4-dioxane, ethyl acetate, methyl acetate, dichloromethane, chloroform, N,N-dimethylformamide, toluene, acetonitrile or xylene) at a temperature in the range of −30° C. to 100° C. In one embodiment of the invention, compound (II) may conveniently take the form of an acid halide (e.g. chloride) as may be prepared by reacting the acid with a suitable reagent (e.g. thionyl chloride)

It will be appreciated by those skilled in the art that in the process of the present invention certain functional groups such as hydroxyl, carboxyl or amino groups in the starting reagents may need to be protected by protecting groups. Thus the preparation of the compounds of formula (I) may additionally involve incorporation and removal of one or more protecting groups. The protection and deprotection of functional groups is for example described in T. W. Greene and P. G. M. Wuts, "Protective Groups in Organic Chemistry, Third Edition", John Wiley & Sons (1999).

The present invention will be described more specifically below with reference to Examples, Preparation Examples and Test Example. However, the present invention is not limited thereto. The abbreviations used in Examples are conventional abbreviations known to a person skilled in the art. Some abbreviations are shown below:

LCMS, LC/MS & LC-MS (liquid chromatography/mass spectrometry); MS (mass spectrometry); MDAP (mass directed auto purification); NMR (nuclear magnetic resonance); s, d, t, dd, m, br (singlet, doublet, triplet, doublet of doublets, multiplet, broad); Ph, Me, Et, Pr, Bu, Bn (phenyl, methyl, ethyl, propyl, butyl, benzyl); THF (tetrahydrofuran); DCM (dichloromethane); DMF (N,N-dimethylformamide); h, hr, hrs (hours); EDC & EDAC (N-3-(dimethylaminopropyl)-N'ethylcarbodiimide hydrochloride); DMAP (4-N,N-dimethylaminopyridine); DMSO (dimethylsulfoxide); UV (ultraviolet); RT & rt (room temperature); Rt (retention time); min & mins (minutes); EtOAc (ethyl acetate); $Et_2O$ (diethyl ether); MeCN (acetonitrile); EtOH (ethanol); MeOH (methanol); $PhCH_3$ & PhMe (toluene); tlc (thin layer chromatography); TFA (trifluoroactic acid); NaOH (sodium hydroxide); HCl (hydrochloric acid); NMP (N-methylpyrrolidinone or 1-methyl-2-pyrrolidinone); HPLC (high performance liquid chromatography); TBAF (tetrabutylammonium fluoride); BuLi (n-butyl lithium); PyBOP: benzotriazol-1-yloxytris (pyrrolidino)phosphonium hexafluorophosphate; $Pd_2$ $dba_3$: tris(dibenzylideneacetone)dipalladium; $Pd(t-Bu_3P)_2$: bis(tri-t-butylphosphine)palladium; TFA: trifluoroacetic acid; pTLC: preparative thin-layer chromatography; HRMS (high resolution mass spectrometry); Tr or Trt (trityl or triphenylmethyl).

$^1$H NMR spectra were recorded on a Bruker AM series spectrometer operating at a (reported) frequency of 400 MHz. Chemical shifts in proton nuclear magnetic resonance spectra are recorded in δ units (ppm) relative to tetramethylsilane and coupling constants (J) are recorded in Hertz (Hz). Patterns are designated as s: singlet, d: doublet, t; triplet, br; broad.

The "room temperature" in the following Examples and Preparation Examples typically refers to about 10° C. to about 35° C. "%" indicates wt % unless otherwise specified.

Chemical names were generated from chemical structures using ChemBioDraw Ultra 11.0 and 12.0.

DESCRIPTION OF FIGURES

FIG. 1 is a Typical Chromatogram from a Chiral HPLC Isolation of Compound 1-(20).

Preparation Example 1

Synthesis of tert-butyl ((4aS,5S,7aS)-7a-(5-amino-2-fluorophenyl)-5-(trifluoromethyl)-4a,5,7,7a-tetrahydro-4H-furo[3,4-d][1,3]thiazin-2-yl)carbamate 1-(13)

1-(2) Synthesis of tert-butyl {[(2S)-1,1,1-trifluorobut-3-en-2-yl]oxy}acetate

To a suspension of trimethylsulfonium iodide (110 g) in THF (500 mL) at −30° C. was added lithium hexamethyldisilazide (530 mL, 1N in THF) portionwise over 45 mins. After stirring at −20° C. for 20 mins, (S)-2-trifluoromethyloxirane (37.97 g) was added at the same temperature over 15 mins, and the mixture was allowed to warm to RT and stirred for 3 h. The slurry was then added portionwise to an ice-cold solution of ten-butyl bromoacetate (105.68 g) in NMP (200 mL). The resulting mixture was allowed to warm to RT and stir for 2 days, before dilution with EtOAc (1 L). The organic layer was washed with sodium bicarbonate (sat., aq., 4×400 mL), dried over MgSO₄ and evaporated. The residue was purified by silica gel column chromatography (5% EtOAc in hexanes) to obtain the title compound (70.1 g) which was used in the subsequent step without purification. $^{1}$H-NMR (400 MHz, CDCl$_3$) δ (ppm): 1.30 (s, 9 H) 3.83-3.96 (m, 2H) 4.14-4.21 (m, 1H) 5.34-5.48 (m, 2H) 5.56-5.71 (m, 1H)
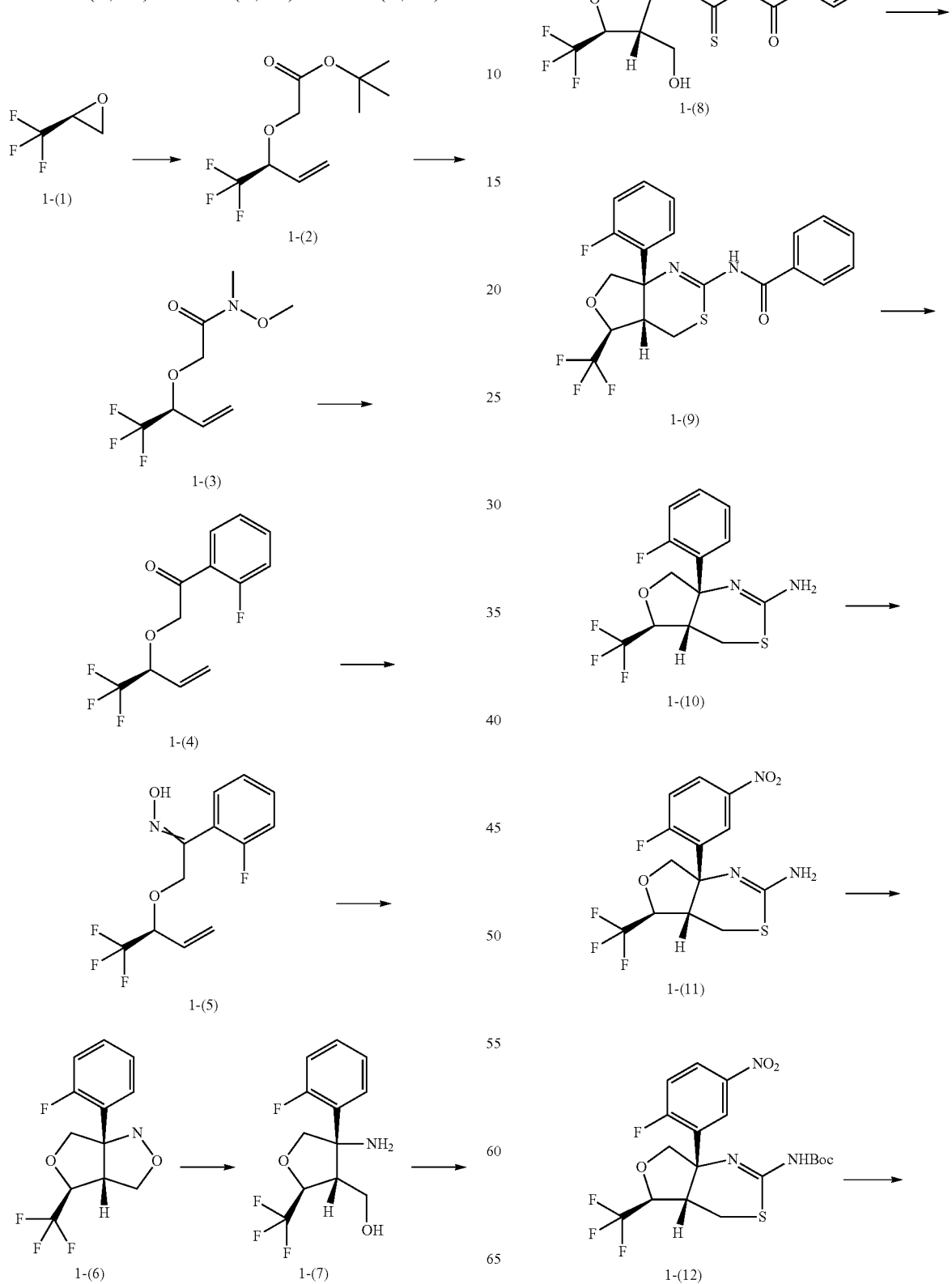

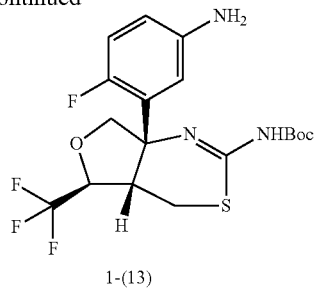

1-(13)

1-(3) Synthesis of (S)—N-methoxy-N-methyl-2-((1,1,1-trifluorobut-3-en-2-yl)oxy)acetamide tert-Butyl {[(2S)-1,1,1-trifluorobut-3-en-2-yl]oxy}acetate (70.1 g, crude) was dissolved in ice-cold formic acid (200 mL). The mixture was allowed to warm to RT and stir overnight. The reaction mixture was then concentrated under reduced pressure, toluene (200 mL) was added, the mixture concentrated, before a second addition of toluene (200 mL) and concentration to an oil. The residue was dissolved in DCM (600 mL), cooled in an ice-bath, and N,N'-carbonyl diimidazole (35 g) was added portionwise over 20 mins. After stirring for 45 mins, N,O-dimethyl hydroxylamine hydrochloride (22 g) was added, and the reaction mixture was allowed to warm to RT and stir overnight. Saturated NaHCO₃ (500 mL) and brine (250 mL) were then added, and the mixture extracted with EtOAc (3×750 mL). The combined organic portions were dried over MgSO₄ and evaporated. The residue was purified by silica gel column chromatography (1% to 30% EtOAc in hexanes) to obtain the title compound (25.17 g). $^1$H-NMR (400 MHz, CDCl₃) δ (ppm) 3.21 (s, 3H), 3.71 (m, 3H), 4.36-4.51 (m, 3H), 5.54-5.69 (m, 2H), 5.84 (ddd, J=17.7, 10.4, 7.3 Hz, 1H)

1-(4) Synthesis of (S)-1-(2-fluorophenyl)-2-((1,1,1-trifluorobut-3-en-2-yl)oxy)ethanone A solution of n-butyllithium in hexane (2.50 M; 90 mL) was added dropwise over 25 mins to a solution of 2-bromofluorobenzene (40.35 g) in THF (250 mL) under a N₂ atmosphere at −78° C. The reaction solution was allowed to warm to −60° C. and stir for 60 min. (S)—N-Methoxy-N-methyl-2-((1,1,1-trifluorobut-3-en-2-yl)oxy)acetamide (40 g) in THF (25 mL) was added dropwise to the reaction solution, and after stirring at −60° C. for 2 h, aqueous NH₄Cl (100 mL) was added to the reaction solution, followed by warming to RT. Brine (200 mL) was added to the reaction solution, and the mixture was extracted with EtOAc (3×400 mL). The combined organic portions were dried over MgSO₄, evaporated, and the residue was purified by silica gel column chromatography (1% to 10% EtOAc in hexanes) to obtain the title compound (33.59 g). $^1$H-NMR (400 MHz, CDCl₃) δ (ppm): 4.40 (pentet, J=6.3 Hz, 1H) 4.81-4.87 (m, 2H), 5.54-5.69 (m, 2H), 5.86 (ddd, J 17.4, 10.4, 7.3 Hz, 1H) 7.12-7.22 (m, 1H) 7.24-7.34 (m, 1H) 7.54-7.63 (m, 1H) 7.94-8.02 (m, 1H).

1-(5) Synthesis of (S)-1-(2-fluorophenyl)-2-((1,1,1-trifluorobut-3-en-2-yl)oxy)ethanone oxime (S)-1-(2-Fluorophenyl)-2-((1,1,1-trifluorobut-3-en-2-yl)oxy)ethanone (41.22 g) was dissolved in anhydrous methanol (400 mL) and hydroxylamine hydrochloride (14.0 g) and sodium acetate (19.0 g) were added. The reaction mixture was heated to 50° C. for 90 min, then cooled to RT, concentrated in vacuo and the residue purified by silica gel chromatography (2% to 15% EtOAc in hexanes) to afford the title compound as a mixture of geometric isomers (40.54 g). $^1$H-NMR (400 MHz, CDCl₃) δ (ppm): 4.04-4.15 (m, 0.8H), 4.18-4.26 (m, 0.2H), 4.44-4.57 (m, 0.4H) 4.79-4.90 (m, 1.6H) 5.37-5.56 (m, 2H) 5.64-5.78 (m, 1H) 7.03-7.26 (m, 2H) 7.33-7.54 (m, 2H), 7.90 (br s, 0.2H), 8.51 (br s, 0.8H).

1-(6) Synthesis of (3aR,4S,6aS)-6a-(2-fluorophenyl)-4-(trifluoromethyl)hexahydrofuro[3,4-c]isoxazole (S)-1-(2-fluorophenyl)-2-((1,1,1-trifluorobut-3-en-2-yl)oxy)ethanone oxime (40.54 g) was dissolved in xylenes (400 mL) and hydroquinone (4.0 g) was added. The reaction mixture was heated to reflux (heating block temperature 140° C.) for 22 h, then cooled and evaporated. The residue was purified by silica gel column chromatography (1% to 30% EtOAc in hexanes) to obtain the title compound (28.76 g). $^1$H-NMR (400 MHz, CDCl₃) δ (ppm): 3.71-3.81 (m, 1H), 4.04-4.35 (m, 4H), 4.51-4.62 (m, 1H), 5.38-5.54 (m, 1H), 7.07-7.26 (m, 2H), 7.32-7.42 (m, 1H), 7.54-7.67 (m, 1H).

1-(7) ((2S,3R,4S)-4-amino-4-(2-fluorophenyl)-2-(trifluoromethyl)tetrahydrofuran-3-yl)methanol (3aR,4S,6aS)-6a-(2-fluorophenyl)-4-(trifluoromethyl)hexahydrofuro[3,4-c]isoxazole (28.76 g) was dissolved in acetic acid (200 mL) and the solution was cooled to 0° C. Zinc (50 g) was added, and the reaction mixture was allowed to warm and stir at RT for 16 h. The reaction mixture was then diluted with EtOAc (500 mL) and filtered through celite, washing with a further 500 mL of EtOAc. The combined organic portions were evaporated, dissolved in chloroform (200 mL), and ammonia (28% aq., 250 mL) was added slowly. The layers were separated, and the aqueous portion was further extracted with chloroform (2×250 mL). The combined organic extracts were dried over anhydrous MgSO₄ and evaporated to afford the title compound (31.12 g) which was used in the subsequent step without further purification. $^1$H-NMR (400 MHz, CDCl₃) δ (ppm): 2.93 (ddd, J=7.7, 4.9, 2.5 Hz, 1H), 3.84 (dd, J=12.4, 4.8 Hz, 1H), 4.05 (dd, J=9.2, 3.2 Hz, 1H), 4.17 (dd, J=12.4, 2.3 Hz, 1H), 4.31 (d, J=9.3 Hz, 1H), 4.72 (quin, J=7.3 Hz, 1H), 7.13 (ddd, J=13.1, 8.8, 1.3 Hz, 1H), 7.22 (td, J=7.6, 1.3 Hz, 1H), 7.31-7.40 (m, 1H), 7.51 (td, J=8.0, 1.6 Hz, 1H)

1-(8) Synthesis of N-(((3S,4R,5S)-3-(2-fluorophenyl)-4-(hydroxymethyl)-5-(trifluoromethyl)tetrahydrofuran-3-yl)carbamothioyl)benzamide Benzoyl isothiocyanate (19.0 mL) was added to a solution containing ((2S,3R,45)-4-amino-4-(2-fluorophenyl)-2-(trifluoromethyl)tetrahydrofuran-3-yl)methanol (28.72 g) in DCM (150 mL), and the mixture was stirred at RT for 18 h. Sodium bicarbonate (sat., aq., 200 mL) was then added, the mixture extracted with EtOAc (3×300 mL), dried over MgSO₄ and concentrated under reduced pressure. The residue was purified by silica gel column chromatography (5% to 30% EtOAc in hexanes) to obtain the title compound (37.07 g). $^1$H-NMR (400 MHz, CDCl₃) δ (ppm): 3.22 (dd, J=8.1, 4.5 Hz, 1H), 3.31 (td, J=8.0, 3.0 Hz, 1H), 3.94-4.07 (m, 1H), 4.31-4.46 (m, 1H), 4.53 (d, J=9.9 Hz, 1H), 4.83 (d, J=9.9 Hz, 1H), 6.97-7.14 (m, 1H), 7.22 (td, J=7.7, 1.3 Hz, 1H), 7.31-7.45 (m, 1H), 7.49-7.61 (m, 2H), 7.61-7.70 (m, 1H), 7.75 (td, J=8.1, 1.5 Hz, 1H), 7.79-7.93 (m, 2H), 8.90 (s, 1H), 11.85 (s, 1H)

1-(9) Synthesis of N-((4aS,5S,7aS)-7a-(2-fluorophenyl)-5-(trifluoromethyl)-4a,5,7,7a-tetrahydro-4H-furo[3,4-d][1,3]thiazin-2-yl)benzamide N-(((3S,4R,5S)-3-(2-Fluorophenyl)-4-(hydroxymethyl)-5-(trifluoromethyl)tetrahydrofuran-3-yl)carbamothioyl)benzamide (31.1 g) was dissolved in pyridine (150 mL), and the mixture cooled to −20° C. Trifluoromethanesulfonic anhydride (14.0 mL) was added dropwise over 30 min and the reaction was allowed to warm to 0° C. After stirring for 2 h, the reaction was quenched by the addition of ammonium chloride (sat., aq., 400 mL) and extracted with EtOAc (3×500 mL). The combined organic extracts were dried over MgSO$_4$, concentrated in vacuo and purified by silica gel column chromatography (2% to 30% EtOAc/hex) to obtain the title compound (18.50 g). $^1$H NMR (400 MHz, CDCl$_3$) δ ppm 2.86 (dd, J=13.9, 3.5 Hz, 1H), 3.25 (d, J=13.6 Hz, 1H), 3.61 (br. s., 1H), 4.00-4.10 (m, 1H), 4.66 (d, J=8.8 Hz, 1H), 4.78-4.87 (m, 1H), 7.12-7.60 (m, 6H), 7.68-7.73 (m, 1H), 7.99-8.16 (br. s., 2H), 8.62-8.66 (m, 1H)

1-(10) Synthesis of N-((4aS,5S,7a5)-7a-(2-fluorophenyl)-5-(trifluoromethyl)-4a,5,7,7a-tetrahydro-4H-furo[3,4-d][1,3]-thiazin-2-yl)benzamide N-((4aS,5S,7aS)-7a-(2-Fluorophenyl)-5-(trifluoromethyl)-4a,5,7,7a-tetrahydro-4H-furo[3,4-d][1,3]thiazin-2-yl)benzamide (21.5 g) was dissolved in methanol (160 mL), 1,8-diazabicyclo[5.4.0]undec-7-ene (16.29 g) was added, and the solution was heated to reflux (heating block temperature 80° C.). After 16 h, the reaction mixture was concentrated under reduced pressure, and the residue purified by silica gel column chromatography (10% to 60% EtOAc in hexanes) to afford the title compound (13.82 g). $^1$H NMR (400 MHz, CDCl$_3$) δ ppm 2.85 (dd, J=13.6, 3.8 Hz, 1H), 3.14 (dd, J=13.5, 3.2 Hz, 1H), 3.33-3.45 (m, 1H), 3.92 (dd, J=8.1, 2.0 Hz, 1H), 4.49 (br. s., 2H), 4.63-4.76 (m, 2H), 7.08 (ddd, J=12.6, 8.1, 1.0 Hz, 1H), 7.13-7.22 (m, 1H), 7.25-7.36 (m, 1H), 7.44 (td, J=8.0, 1.9 Hz, 1H)

1-(11) Synthesis of (4aS,5S,7aS)-7a-(2-fluoro-5-nitrophenyl)-5-(trifluoromethyl)-4a,5,7,7a-tetrahydro-4H-furo[3,4-d][1,3]thiazin-2-amine N-((4aS,5S,7aS)-7a-(2-Fluorophenyl)-5-(trifluoromethyl)-4a,5,7,7a-tetrahydro-4H-furo[3,4-d][1,3]thiazin-2-yl)benzamide (5.15 g) was dissolved in TFA (75 mL), and the solution was cooled to 0° C. Sulfuric acid (conc., 20 mL) was added, followed by fuming nitric acid (2 mL) dropwise over 20 mins. After stirring at 0° C. for 90 mins, the reaction mixture was poured onto ice (200 g) and basified to pH 12 with 6N NaOH (aq.). After allowing the ice to melt, the mixture was extracted with EtOAc (3×500 mL), and the combined organic portions dried over MgSO$_4$ and evaporated to afford the title compound (22.1 g, purity approx. 71%) which was used in the subsequent step without purification. $^1$H NMR (400 MHz, CDCl$_3$) δ ppm 2.89 (d, J=3.8 Hz, 1H), 3.09 (br. s., 1 H), 3.28-3.54 (m, 1H), 3.80-4.03 (m, 1H), 4.50-4.70 (m, 3H), 4.71-4.86 (m, 1H), 7.21-7.30 (m, 1H), 8.18-8.28 (m, 1H), 8.45 (dd, J=6.8, 2.8 Hz, 1H)

1-(12) Synthesis of tert-butyl ((4aS,5S,7a5)-7a-(2-fluoro-5-nitrophenyl)-5-(trifluoromethyl)-4a,5,7,7a-tetrahydro-4H-furo[3,4-d][1,3]thiazin-2-yl)carbamate (4aS,5S,7aS)-7a-(2-Fluoro-5-nitrophenyl)-5-(trifluoromethyl)-4a,5,7,7a-tetrahydro-4H-furo[3,4-d][1,3]thiazin-2-amine (20.6 g, crude) was dissolved in THF (300 mL), di-tert-butyl dicarbonate (12 g) was added portionwise over 20 mins and the reaction mixture was heated to 60° C. Further portions of di-tert-butyl dicarbonate (10 g) were added until starting material was consumed by TLC. The reaction mixture was cooled and sodium bicarbonate (sat., aq., 200 mL) and brine (200 mL) were added. The mixture was then extracted with EtOAc (3×500 mL) and the combined organic portions were dried over MgSO$_4$ and evaporated. The residue was purified by silica gel column chromatography (10% to 25% EtOAc in hexanes) to afford the title compound (16.62 g). $^1$H NMR (400 MHz, CDCl$_3$) δ ppm 1.55 (s, 9H), 2.73-2.84 (m, 1H), 2.92-3.05 (m, 1H), 3.43-3.55 (m, 1H), 3.81-3.94 (m, 1H), 4.57 (d, J=8.3 Hz, 1H), 4.73-4.83 (m, 1H), 7.19-7.39 (m, 2H), 8.20-8.29 (m, 1H), 8.32 (d, J=6.8 Hz, 1H)

1-(13) Synthesis of tert-butyl ((4aS,5S,7aS)-7a-(5-amino-2-fluorophenyl)-5-(trifluoromethyl)-4a,5,7,7a-tetrahydro-4H-furo[3,4-d][1,3]thiazin-2-yl)carbamate tert-Butyl ((4aS,5S,7aS)-7a-(2-fluoro-5-nitrophenyl)-5-(trifluoromethyl)-4a,5,7,7a-tetrahydro-4H-furo[3,4-d][1,3]thiazin-2-yl)carbamate (16.61 g) was dissolved in ethanol (250 mL) and tin chloride dihydrate (25.0 g) was added. After stirring at RT for 18 h, the solution was poured onto NaOH (2N aq., 300 mL) and Celite® (~50 g) was added. The resulting mixture was filtered through more Celite® and extracted with EtOAc (2×500 mL). The combined organic portions were dried over MgSO$_4$ and evaporated to afford the title compound (15.52 g). This material could be used crude but a portion was purified by silica gel column chromatography (20% to 50% EtOAc in hexanes) to afford pure material (recovery 79%). $^1$H NMR (400 MHz, CDCl$_3$) δ ppm 1.53 (s, 9H), 2.77 (d, J=14.4 Hz, 1H), 3.09 (br. s., 1H), 3.46 (br. s., 1H), 3.62 (br. s., 2H), 3.87 (br. s., 1H), 4.61 (d, J=8.6 Hz, 1H), 4.71 (br. s., 1H), 6.61 (br. s., 2H), 6.85-6.95 (m, 1H)

Preparation Example 2

Synthesis of tert-butyl ((4aS,5S,7aS)-7a-(5-amino-2-fluorophenyl)-5-(trifluoromethyl)-4a,5,7,7a-tetrahydro-4H-furo[3,4-d][1,3]thiazin-2-yl)carbamate
2-(10)

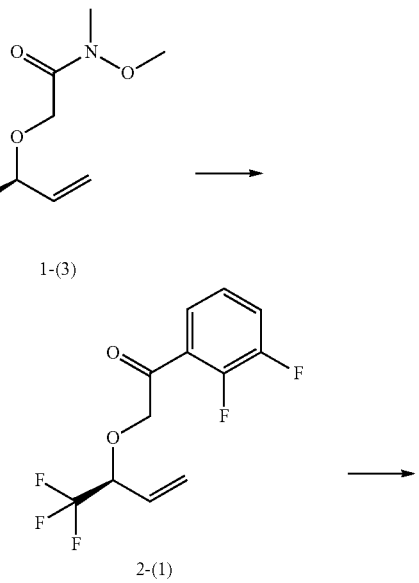

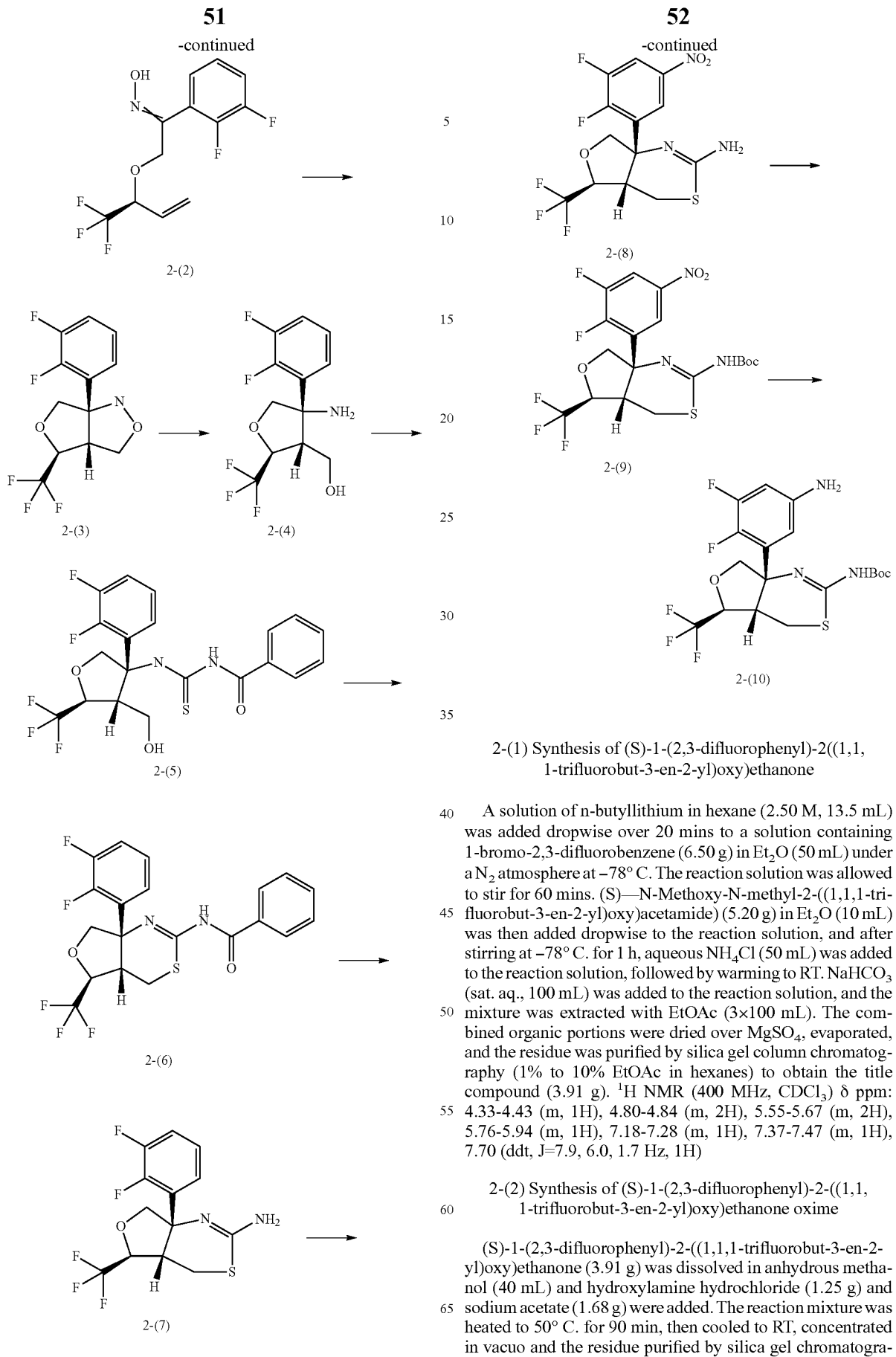

2-(1) Synthesis of (S)-1-(2,3-difluorophenyl)-2((1,1,1-trifluorobut-3-en-2-yl)oxy)ethanone A solution of n-butyllithium in hexane (2.50 M, 13.5 mL) was added dropwise over 20 mins to a solution containing 1-bromo-2,3-difluorobenzene (6.50 g) in Et₂O (50 mL) under a N₂ atmosphere at −78° C. The reaction solution was allowed to stir for 60 mins. (S)—N-Methoxy-N-methyl-2-((1,1,1-trifluorobut-3-en-2-yl)oxy)acetamide) (5.20 g) in Et₂O (10 mL) was then added dropwise to the reaction solution, and after stirring at −78° C. for 1 h, aqueous NH₄Cl (50 mL) was added to the reaction solution, followed by warming to RT. NaHCO₃ (sat. aq., 100 mL) was added to the reaction solution, and the mixture was extracted with EtOAc (3×100 mL). The combined organic portions were dried over MgSO₄, evaporated, and the residue was purified by silica gel column chromatography (1% to 10% EtOAc in hexanes) to obtain the title compound (3.91 g). $^1$H NMR (400 MHz, CDCl₃) δ ppm: 4.33-4.43 (m, 1H), 4.80-4.84 (m, 2H), 5.55-5.67 (m, 2H), 5.76-5.94 (m, 1H), 7.18-7.28 (m, 1H), 7.37-7.47 (m, 1H), 7.70 (ddt, J=7.9, 6.0, 1.7 Hz, 1H)

2-(2) Synthesis of (S)-1-(2,3-difluorophenyl)-2-((1,1,1-trifluorobut-3-en-2-yl)oxy)ethanone oxime (S)-1-(2,3-difluorophenyl)-2-((1,1,1-trifluorobut-3-en-2-yl)oxy)ethanone (3.91 g) was dissolved in anhydrous methanol (40 mL) and hydroxylamine hydrochloride (1.25 g) and sodium acetate (1.68 g) were added. The reaction mixture was heated to 50° C. for 90 min, then cooled to RT, concentrated in vacuo and the residue purified by silica gel chromatography (2% to 20% EtOAc in hexanes) to afford the title compound as a mixture of geometric isomers (4.10 g). $^1$H-NMR (400 MHz, CDCl$_3$) δ (ppm): 4.04-4.26 (m 1H), 4.43-4.55 (m, 0.4H) 4.80-4.89 (m, 1.6H) 5.39-5.55 (m, 2H) 5.64-5.80 (m, 1H) 7.05-7.30 (m, 3H), 7.76 (br s, 0.2H), 8.30 (br s, 0.8H).

2-(3) Synthesis of (4S)-6a-(2,3-difluorophenyl)-4-(trifluoromethyl)hexahydrofurol-3,4-c]isoxazole (S)-1-(2,3-difluorophenyl)-2-((1,1,1-trifluorobut-3-en-2-yl)oxy)ethanone oxime (4.10 g) was dissolved in xylenes (40 mL) and hydroquinone (380 mg) was added. The reaction mixture was heated to reflux (heating block temperature 140° C.) for 20 h, then cooled and evaporated. The residue was purified by silica gel column chromatography (1% to 25% EtOAc in hexanes) to obtain the title compound (3.16 g). $^1$H NMR (400 MHz, CDCl$_3$) δ ppm 3.77 (br. s., 1H), 3.99-4.16 (m, 1H), 4.16-4.22 (m, 1H), 4.22-4.44 (m, 2H), 4.51 (d, J=9.9 Hz, 1H), 5.44 (s, 1H), 7.07-7.24 (m, 2H), 7.38 (br. s., 1H)

2-(4) Synthesis of ((2S,3R,4S)-4-amino-4-(2,3-difluorophenyl)-2-(trifluoromethyl)tetrahydrofuran-3-yl)methanol (4S)-6a-(2,3-difluorophenyl)-4-(trifluoromethyl)hexahydrofuro[3,4-c]isoxazole (3.16 g) was dissolved in acetic acid (20 mL) and the reaction mixture cooled to 0° C. Zinc (5.0 g) was added, and the reaction was allowed to warm and stir at RT for 20 h. The reaction mixture was then diluted with EtOAc (50 mL) and filtered through Celite®, washing with a further 100 mL of EtOAc. The combined organic portions were evaporated, dissolved in CHCl$_3$ (20 mL), and ammonia (28% aq., 25 mL) was added slowly. The layers were separated, and the aqueous portion was further extracted with CHCl$_3$ (2×25 mL). The combined organic extracts were dried over anhydrous MgSO$_4$ and evaporated to afford the title compound (3.12 g) which was used in the subsequent step without further purification. $^1$H NMR (400 MHz, CDCl$_3$) δ ppm 2.93 (ddd, J=7.8, 5.1, 2.8 Hz, 1H), 3.85 (dd, J=12.4, 5.1 Hz, 1H), 4.03 (dd, J=9.1, 2.8 Hz, 1H), 4.14 (dd, J=12.3, 2.7 Hz, 1H), 4.35 (d, J=9.1 Hz, 1H), 4.68 (quin, J=7.3 Hz, 1H), 7.09-7.25 (m, 2H), 7.25-7.34 (m, 1H)

2-(5) Synthesis of N-(((3S,4R,5S)-3-(2,3-difluorophenyl)-4-(hydroxymethyl)-5-(trifluoromethyl)tetrahydrofuran-3-yl)carbamothioyl)benzamide Benzoyl isothiocyanate (2.0 mL) was added to a solution containing ((2S,3R,4S)-4-amino-4-(2,3-difluorophenyl)-2-(trifluoromethyl)tetrahydrofuran-3-yl)methanol (3.12 g) in DCM (20 mL), and the mixture was stirred at RT for 18 h. Sodium bicarbonate (sat., aq., 50 mL) was then added, the mixture extracted with EtOAc (3×75 mL), dried over MgSO$_4$ and concentrated under reduced pressure. The residue was purified by silica gel column chromatography (5% to 40% EtOAc in hexanes) to obtain the title compound (4.18 g). $^1$H NMR (400 MHz, CDCl$_3$) δ ppm 3.12 (dd, J=7.6, 4.3 Hz, 1H), 3.18-3.29 (m, 1H), 4.03 (ddd, J=12.3, 7.2, 4.5 Hz, 1H), 4.35-4.49 (m, 1H), 4.59 (d, J=9.9 Hz, 1H), 4.81 (d, J=9.6 Hz, 1H), 7.07-7.23 (m, 2H), 7.49 (t, J=7.2 Hz, 1H), 7.56 (t, J=7.7 Hz, 2H), 7.67 (t, J=7.5 Hz, 1H), 7.88 (d, J=7.1 Hz, 2H), 8.92 (s, 1H), 11.89 (s, 1H)

2-(6) Synthesis of N-((4aS,5S,7aS)-7a-(2,3-difluorophenyl)-5-(trifluoromethyl)-4a,5,7,7a-tetrahydro-4H-furo[3,4-d][1,3]thiazin-2-yl)benzamide N-(((3S,4R,5S)-3-(2,3-Difluorophenyl)-4-(hydroxymethyl)-5-(trifluoromethyl)tetrahydrofuran-3-yl)carbamothioyl)benzamide (2.99 g) was dissolved in pyridine (14 mL), and the mixture cooled to −20° C. Trifluoromethanesulfonic anhydride (1.55 mL) was added dropwise over 10 min and the reaction mixture was allowed to warm to −10° C. After stirring for 2 h, a further portion of trifluoromethanesulfonic anhydride (1.0 mL) was added dropwise over 10 min, the reaction was stirred for a further 2 h, and was then quenched by the addition of ammonium chloride (sat., aq., 50 mL) and extracted with EtOAc (3×100 mL). The combined organic extracts were dried over MgSO$_4$, concentrated in vacuo and purified by silica gel column chromatography (5% to 20% EtOAc/hex) to obtain the title compound (1.20 g). $^1$H NMR (400 MHz, CDCl$_3$) δ ppm 2.86 (d, J=10.6 Hz, 1H), 3.20 (br. s., 1H), 3.55 (br. s., 1H), 4.04 (br. s., 1H), 4.65 (d, J=8.8 Hz, 1H), 4.81 (br. s., 1H), 7.06-7.24 (m, 3H), 7.40-7.64 (m, 3H), 7.82-8.21 (m, 2H)

2-(7) Synthesis of (4aS,5S,7aS)-7a-(2,3-difluorophenyl)-5-(trifluoromethyl)-4a,5,7,7a-tetrahydro-4H-furo[3,4-d][1,3]thiazin-2-amine N-((4aS,5S,7aS)-7a-(2,3-Difluorophenyl)-5-(trifluoromethyl)-4a,5,7,7a-tetrahydro-4H-furo[3,4-d][1,3]thiazin-2-yl)benzamide (2.00 g) was dissolved in methanol (250 mL), 1,8-diazabicyclo[5.4.0]undec-7-ene (1.53 g) was added, and the solution was heated to reflux (heating block temperature 80° C.). After 3 h, the reaction mixture was concentrated under reduced pressure, diluted with water (100 mL) and extracted with EtOAc (3×100 mL). The combined organic portions were dried over MgSO$_4$, evaporated, and the residue purified by silica gel column chromatography (0% to 50% EtOAc in hexanes) to afford the title compound (1.42 g). $^1$H NMR (400 MHz, CDCl$_3$) δ ppm 2.86 (dd, J=13.6, 3.8 Hz, 1H), 3.15 (dd, J=13.8, 3.2 Hz, 1H), 3.27-3.42 (m, 1 H), 3.93 (dd, J=8.2, 1.9 Hz, 1H), 4.39-4.78 (m, 4H), 6.96-7.25 (m, 3H)

2-(8) Synthesis of (4aS,5S,7aS)-7a-(2,3-difluoro-5-nitrophenyl)-5-(trifluoromethyl)-4a,5,7,7a-tetrahydro-4H-furo[3,4-d][1,3]thiazin-2-amine (4aS,5S,7aS)-7a-(2,3-Difluorophenyl)-5-(trifluoromethyl)-4a,5,7,7a-tetrahydro-4H-furo[3,4-d][1,3]thiazin-2-amine (1.42 g) was dissolved in TFA (6 mL), and the solution was cooled to 0° C. Sulfuric acid (conc., 1 mL) was added, followed by fuming nitric acid (0.30 mL) dropwise over 20 mins. After stirring at 0° C. for 1 h, the reaction mixture was poured onto ice (50 g) and basified to pH 12 with 2 N NaOH (aq.). After allowing the ice to melt, the mixture was extracted with EtOAc (3×75 mL), and the combined organic portions dried over MgSO$_4$ and evaporated to afford the title compound (1.91 g, purity approx. 80%) which was used in the subsequent step without purification. $^1$H NMR (400 MHz, CDCl$_3$) δ ppm 2.88 (dd, J=13.8, 3.9 Hz, 1H), 3.11 (dd, J=13.6, 2.8 Hz, 1H), 3.37 (dt, J=7.4, 3.5 Hz, 1H), 3.93 (d, J=7.8 Hz, 1H), 4.53-4.83 (m, 4H), 8.09 (ddd, J=9.0, 6.3, 2.9 Hz, 1H), 8.27 (dt, J=5.2, 2.6 Hz, 1H)

2-(9) Synthesis of tert-butyl ((4aS,5S,7aS)-7a-(2,3-difluoro-5-nitrophenyl)-5-(trifluoromethyl)-4a,5,7,7a-tetrahydro-4H-furo[3,4-d][1,3]thiazin-2-yl)carbamate (4aS,5S,7aS)-7a-(2,3-Difluoro-5-nitrophenyl)-5-(trifluoromethyl)-4a,5,7,7a-tetrahydro-4H-furo[3,4-d][1,3]thiazin-2-amine (1.91 g, crude) was dissolved in THF (10 mL), di-tert-butyl dicarbonate (1.3 g) was added portionwise over 20 mins and the reaction mixture was heated to 65° C. After 3 h, the reaction mixture was cooled and sodium bicarbonate (sat., aq., 50 mL) was added. The mixture was then extracted with EtOAc (3×750 mL) and the combined organic portions were dried over MgSO$_4$ and evaporated. The residue was purified by silica gel column chromatography (0% to 20% EtOAc in hexanes) to afford the title compound (1.43 g crude, in a mixture with the bis-boc version).

2-(10) Synthesis of tert-butyl ((4aS,5S,7a5)-7a-(5-amino-2,3-difluorophenyl)-5-(trifluoromethyl)-4a,5,7,7a-tetrahydro-4H-furo[3,4-d][1,3]thiazin-2-yl)carbamate The crude mixture obtained in preparation example 2-(9) containing tert-Butyl ((4aS,5S,7aS)-7a-(2,3-difluoro-5-nitrophenyl)-5-(trifluoromethyl)-4a,5,7,7a-tetrahydro-4H-furo[3,4-d][1,3]thiazin-2-yl)carbamate) (1.43 g) was dissolved in ethanol (25 mL) and tin chloride dihydrate (2.50 g) was added. After stirring for 18 h, the solution was poured onto NaOH (2N aq., 100 mL) and extracted with EtOAc (3×100 mL). The combined organic portions were dried over MgSO$_4$, evaporated and purified by silica gel column chromatography (0% to 30% EtOAc in hexanes) to afford firstly the bis-boc product (730 mg), and secondly the title compound (300 mg). $^1$H NMR (400 MHz, CDCl$_3$) δ ppm 1.53 (s, 9H), 2.76 (dd, J=13.9, 3.8 Hz, 1H), 3.08 (d, J=13.6 Hz, 1H), 3.36-3.45 (m, 1H), 3.71 (br. s., 2H), 3.90 (d, J=8.3 Hz, 1H), 4.57 (d, J=8.6 Hz, 1H), 4.68-4.79 (m, 1H), 6.30-6.37 (m, 1H), 6.42-6.49 (m, 1H)

Preparation Example 3

Synthesis of 5-ethoxypyrazine-2-carboxylic acid (3-(2))

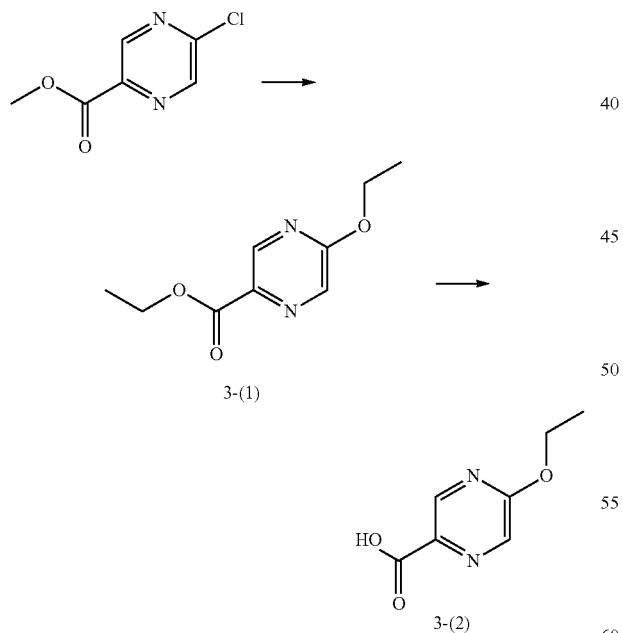

Synthesis of ethyl 5-ethoxypyrazine-2-carboxylate 3-(1)

A stirred solution of methyl 5-chloropyrazine-2-carboxylate (0.50 g) in ethanol (10 mL) was cooled to 0° C., and sodium ethoxide (21% w/w solution in ethanol, 1 mL) was added over 10 mins. After allowing to warm to RT and stir for 2 h, water (100 mL) was added and the mixture extracted with EtOAc (2×150 mL). The combined organic portions were dried over MgSO$_4$ and evaporated to afford the title compound. (0.65 g, purity approx. 85%). $^1$H NMR (400 MHz, CDCl$_3$) δ ppm 1.45 (t, J=7.1 Hz, 3 H), 1.46 (t, J=7.1 Hz, 3H), 4.48 (q, J=7.1 Hz, 2H), 4.49 (q, J=7.1 Hz, 2H), 8.28 (d, J=1.3 Hz, 1H), 8.88 (d, J=1.3 Hz, 1H)

Synthesis of 5-ethoxypyrazine-2-carboxylic acid 3-(2)

Ethyl 5-ethoxypyrazine-2-carboxylate (0.65 g, approx. purity 85%) was dissolved in dioxan (3 mL) and water (3 mL) was added, followed by lithium hydroxide monohydrate (255 mg, portionwise over 10 mins). After stirring at RT for 24 h, Et$_2$O (25 mL) and NaHCO$_3$ (sat., aq., 25 mL) were added. The layers were separated and the organic layer was extracted with NaOH (1 N, aq., 25 mL). The combined aqueous portions were acidified with 6N HCl to pH 2, and the mixture extracted with EtOAc (3×40 mL). The combined EtOAc extracts were dried over MgSO$_4$ and evaporated to afford the title compound as an off-white powder. $^1$H NMR (400 MHz, CDCl$_3$) δ ppm 1.47 (t, J=7.1 Hz, 3H), 4.53 (q, J=7.1 Hz, 2H), 8.16 (d, J=1.2 Hz, 1H), 8.98 (d, J=1.2 Hz, 1H)

Preparation Example 4

Synthesis of 5-ethoxypyrazine-2-carboxylic acid (4-(3))

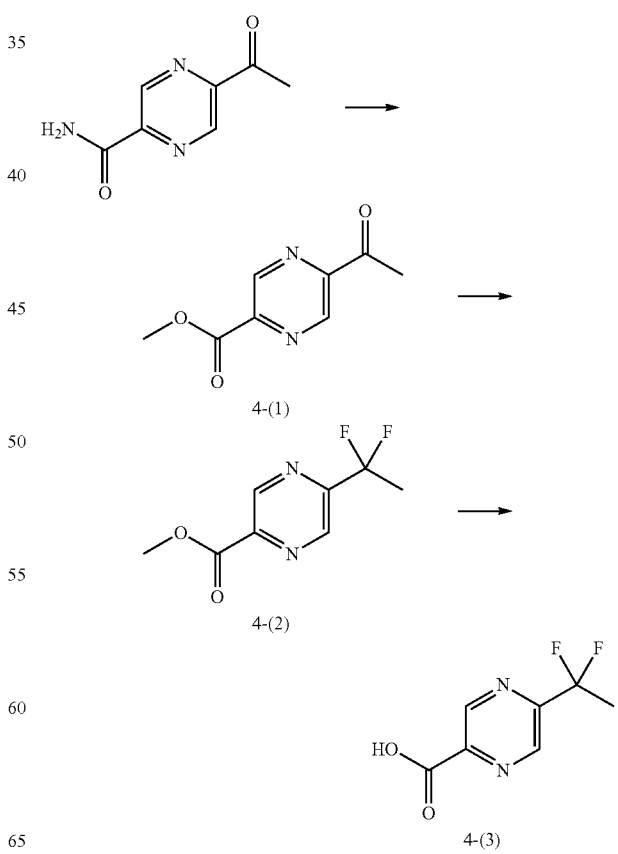

Methyl 5-acetylpyrazine-2-carboxylate 4-(1)

5-Acetylpyrazine-2-carboxamide (3.275 g) was dissolved in methanolic HCl (1.25 N, 150 mL) and the reaction mixture was heated to reflux and stirred overnight. After cooling, sodium bicarbonate was added and the mixture was extracted with EtOAc.

The EtOAc layer was dried over MgSO$_4$ and evaporated to afford the title compound (3.79 g, approx purity 90%). $^1$H NMR (400 MHz, CDCl$_3$) δ ppm 2.78 (s, 3H), 4.10 (s, 3H), 9.33 (d, J=1.5 Hz, 1H), 9.36 (d, J=1.5 Hz, 1H)

Methyl 5-(1,1-difluoroethyl)pyrazine-2-carboxylate 4-(2)

Methyl 5-acetylpyrazine-2-carboxylate (300 mg, approx purity 90%) was dissolved in DCM (15 mL) and cooled to 0° C. under nitrogen. Bis(2-methoxyethyl)aminosulfur trifluoride (0.61 mL) was added dropwise and the reaction mixture allowed to warm to RT and stir overnight. Sodium bicarbonate (sat., aq.) was added cautiously and the mixture extracted with DCM. The organic portions were dried over MgSO$_4$, evaporated and purified by silica gel chromatography (35% EtOAc in hexane) to afford the title compound (155 mg) as a white solid. $^1$H NMR (400 MHz, CDCl$_3$) δ ppm 2.00 (t, J=18.8 Hz, 3H), 4.01 (s, 3H), 8.98 (d, J=1.5 Hz, 1H), 9.24 (d, J=1.5 Hz, 1H)

5-(1,1-Difluoroethyl)pyrazine-2-carboxylic acid 4-(3)

Methyl 5-(1,1-difluoroethyl)pyrazine-2-carboxylate (0.65 g, approx. purity 85%) was dissolved in dioxan (2 mL) and water (2 mL) was added, followed by lithium hydroxide monohydrate (54 mg, portionwise). After stirring at RT for 90 mins, the mixture was concentrated to 2 mL and Et$_2$O (20 mL) added. The mixture was then extracted with NaOH (1 N, aq., 20 mL), and the aqueous portions acidified with 6N HCl to pH 2. The aqueous portion was then extracted with EtOAc, dried over MgSO$_4$ and evaporated to afford the title compound as a white solid (119 mg). $^1$H NMR (400 MHz, CDCl$_3$) δ ppm 2.11 (t, J=18.8 Hz, 3H), 9.01 (d, J=1.3 Hz, 1H), 9.47 (d, J=1.3 Hz, 1H)

Preparation Example 5

Synthesis of 5-(fluoromethyl)pyrazine-2-carboxylic acid (5-(3))

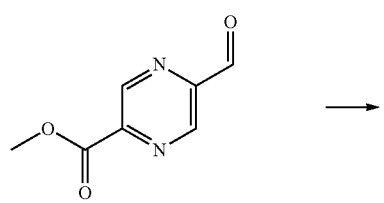

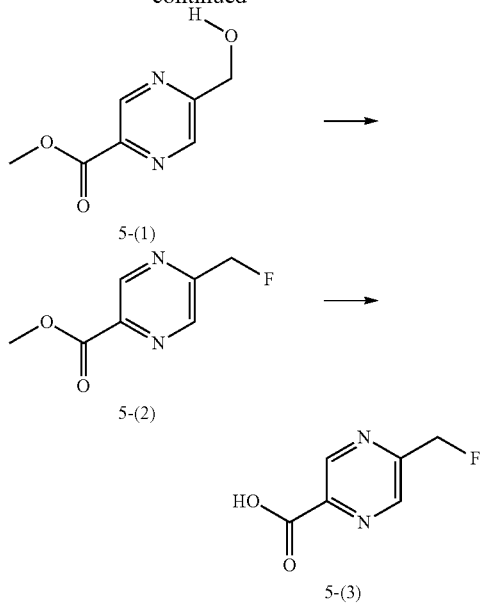

Methyl 5-(hydroxymethyl)pyrazine-2-carboxylate 5-(1)

To a solution of methyl 5-formylpyrazine-2-carboxylate (2.47 g) in THF (20 mL) was added sodium borohydride (170 mg) portionwise over 10 mins. After stirring for 1 h, methanol (10 mL) was added. The reaction mixture was stirred for a further 20 mins, and then HCl (1 N, aq., 20 mL) and brine (20 mL) were added. The mixture was extracted with EtOAc (3×40 mL) and the combined organic portions dried over MgSO$_4$ and evaporated to afford the title compound (1.31 g). $^1$H NMR (400 MHz, CDCl$_3$) δ ppm 4.07 (s, 3H), 4.98 (br. s., 2H), 8.80 (s, 1H), 9.27 (s, 1H)

Methyl 5-(fluoromethyl)pyrazine-2-carboxylate 5-(2)

To a solution of methyl 5-(hydroxymethyl)pyrazine-2-carboxylate (0.64 g) in THF (20 mL) was added triethylamine (2.30 g) and the solution was cooled to 0° C. Triethylamine trihydrofluoride (1.22 g) was then added followed by nonafluorobutanesulfonyl fluoride (2.28 g) dropwise over 5 mins. After warming to RT and stirring for 2 h, NaHCO$_3$ (sat., aq., 100 mL) was added, and the mixture was extracted with EtOAc (2×50 mL). The combined organic portions were dried over MgSO$_4$, evaporated, and purified by silica gel chromatography (5% to 50% EtOAc in hexane) to afford the title compound (94 mg). $^1$H NMR (400 MHz, CDCl$_3$) δ ppm 4.07 (s, 3H), 5.67 (d, J=46.5 Hz, 2H), 8.89 (s, 1H), 9.28 (s, 1H)

5-(Fluoromethyl)pyrazine-2-carboxylic acid 5-(3)

Methyl 5-(fluoromethyl)pyrazine-2-carboxylate (94 mg) was dissolved in dioxan (1 mL) and water (1 mL) was added, followed by lithium hydroxide monohydrate (60 mg). After stirring at RT for 18 h, Et$_2$O (20 mL) was added and the mixture was then extracted with NaOH (1 N, aq., 2×20 mL). The aqueous portions were acidified with 6N HCl to pH 1, extracted with EtOAc (2×40 mL), the combined organic portions dried over MgSO$_4$ and evaporated to afford the title compound as a white solid (71 mg). $^1$H NMR (400 MHz, CDCl$_3$) δ ppm 5.70 (d, J=46.2 Hz, 2H), 8.85 (s, 1H), 9.40 (s, 1H)

Preparation Example 6

Synthesis of 5-difluoromethylpyrazine-2-carboxylic acid (6-(5)

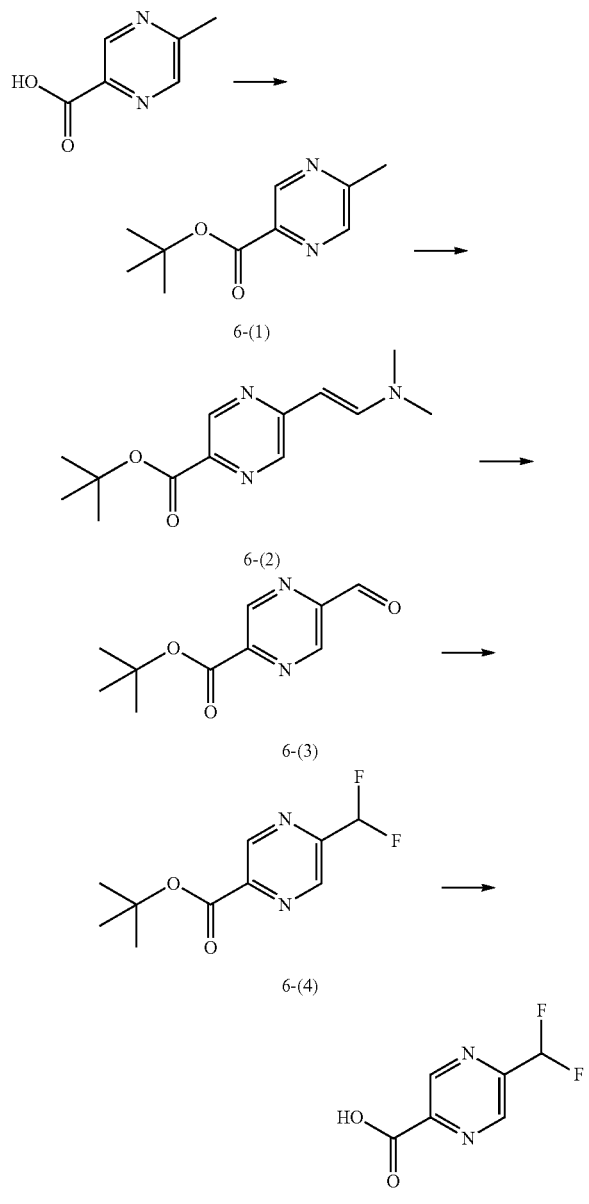

Synthesis of t-butyl 5-methylpyrazine-2-carboxylate 6-(1)

A boron trifluoride-diethyl ether complex (91.7 μL) was added dropwise to a suspension of 2-methylpyrazine-5-carboxylic acid (1 g) and tert-butyl 2,2,2-trichloroacetimidate (4.75 g) in THF (20 mL) under ice-cooling. The reaction solution was warmed to RT, followed by stirring for 2 h. A saturated NaCl solution and EtOAc were added to the reaction solution, and the organic layer was separated. The organic layer was dried over anhydrous MgSO$_4$, and the insoluble matter was separated by filtration. The filtrate was concentrated and purified by silica gel column chromatography to obtain the title compound (1.4 g). $^1$H-NMR (CDCl$_3$) δ (ppm): 1.65 (s, 9H), 2.65 (s, 3H), 8.57 (d, J=1.2 Hz, 1H), 9.10 (d, J=1.6 Hz, 1H).

Synthesis of t-butyl 5-((E)-2-dimethylamino-vinyl)-pyrazine-2-carboxylate 6-(2)

A mixture of t-butyl 5-methylpyrazine-2-carboxylate (1.35 g), DMF (25 mL) and N,N-dimethylformamide dimethylacetal (25 mL) was stirred at 130° C. for 5 h. The reaction solution was cooled to RT and diluted with EtOAc. The mixture was washed with a saturated NaCl solution three times. The organic layer was dried over anhydrous MgSO$_4$, and the insoluble matter was separated by filtration. The filtrate was concentrated and the residue was purified by silica gel column chromatography to obtain the title compound (648 mg). $^1$H-NMR (CDCl$_3$) δ (ppm): 1.63 (s, 9H), 3.00 (s, 6H), 5.16 (d, J=12.8 Hz, 1H), 7.72 (d, J=12.8 Hz, 1H), 8.16 (d, J=1.2 Hz, 1H), 8.81 (d, J=1.6 Hz, 1H).

Synthesis of t-butyl 5-formylpyrazine-2-carboxylate 6-(3)

Sodium periodate (1.67 g) was added to a solution of t-butyl 5-((E)-2-dimethylamino-vinyl)-pyrazine-2-carboxylate (645 mg) in 50% THF-water (26 mL), and the mixture was stirred at RT for 4 h. A saturated NaHCO$_3$ solution and EtOAc were added to the reaction solution, and the organic layer was separated. The organic layer was washed with a saturated NaCl solution and dried over anhydrous MgSO$_4$. The insoluble matter was separated by filtration and the filtrate was concentrated. The residue was purified by silica gel column chromatography to obtain the title compound (249 mg). $^1$H-NMR (CDCl$_3$) δ (ppm): 1.68 (s, 9H), 9.25 (d, J=1.2 Hz, 1H), 9.36 (d, J=1.6 Hz, 1H), 10.2 (s, 1H).

Synthesis of t-butyl 5-difluoromethylpyrazine-2-carboxylate 6-(4)

[Bis(2-methoxyethyl)amino]sulfur trifluoride (662 μL) was added dropwise to a solution of t-butyl 5-formylpyrazine-2-carboxylate (249 mg) in CH$_2$Cl$_2$ (12 mL) under a N$_2$ atmosphere under ice-cooling. The reaction solution was stirred for 2 h while gradually returning to RT. A saturated NaHCO$_3$ solution and EtOAc were added to the reaction solution, and the organic layer was separated. The organic layer was washed with a saturated NaCl solution and dried over anhydrous MgSO$_4$. The insoluble matter was separated by filtration and the filtrate was concentrated. The residue was purified by silica gel column chromatography to obtain the title compound (175 mg). $^1$H-NMR (CDCl$_3$) δ (ppm): 1.67 (s, 9H), 6.75 (t, J=54.4 Hz, 1H), 9.02 (d, J=0.8 Hz, 1H), 9.25 (d, J=0.8 Hz, 1H).

Synthesis of 5-difluoromethylpyrazine-2-carboxylic acid 6-(5)

Trifluoroacetic acid (1 mL) was added to a solution of t-butyl 5-difluoromethylpyrazine-2-carboxylate (175 mg) in dichloromethane (1 mL), and the mixture was stirred at RT for 5 h. Ether and 5 N NaOH were added to the reaction solution. The aqueous layer was separated and made acidic with 5 N hydrochloric acid. EtOAc was added to the aqueous layer, and the organic layer was separated. The organic layer was dried over anhydrous MgSO$_4$, and the insoluble matter was separated by filtration. The filtrate was concentrated to obtain the title compound (100 mg). $^1$H-NMR (CDCl$_3$) δ (ppm): 6.80 (t, J=54.4 Hz, 1H), 9.02 (s, 1H), 9.47 (s, 1H).

Preparation Example 7

Synthesis of 5-cyanopyridine-2-carboxylic acid
(7-(2))

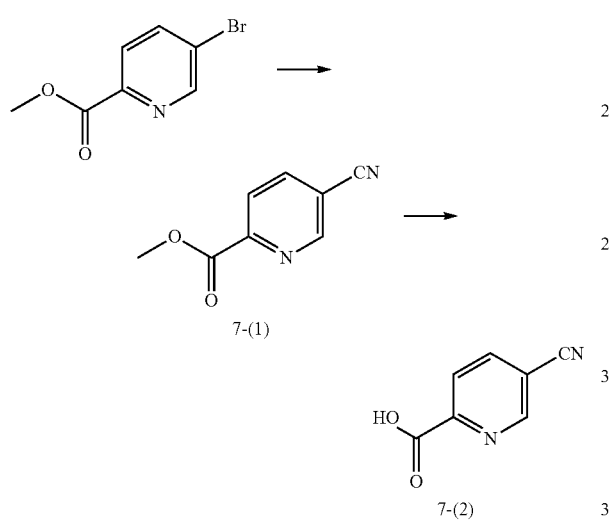

Synthesis of methyl 5-cyanopyridine-2-carboxylate 7 (1)

A mixture of methyl 5-bromopyridine-2-carboxylate (2.8 g) and copper cyanide (3.6 g) in NMP (30 mL) was heated with stirring at 170° C. for 1.5 h. Water was added to the reaction solution at RT, and the insoluble matter was removed by filtration. The filtrate was extracted with EtOAc. The extract was washed with a saturated NaCl solution and then dried over anhydrous MgSO$_4$. The drying agent was removed by filtration and the filtrate was concentrated under reduced pressure. The resulting crude product was purified by silica gel column chromatography (EtOAc-heptane system) to obtain the title compound (920 mg). $^1$H-NMR (400 MHz, CDCl$_3$) δ (ppm): 4.06 (s, 3H), 8.16 (dd, J=2.0, 8.0 Hz, 1H), 8.27 (d, J=8.0 Hz, 1H), 9.01 (d, J=2.0 Hz, 1H).

Synthesis of 5-cyanopyridine-2-carboxylic acid 7-(2)

A solution of the compound of Preparation Example 13-(1) (920 mg) and a 5 N NaOH solution (2.26 mL) in ethanol (30 mL) was stirred at RT for 10 min. 5 N hydrochloric acid (5.2 mL) was added to the reaction solution at RT, followed by extraction with EtOAc. The extract was dried over anhydrous MgSO$_4$. The drying agent was removed by filtration and the filtrate was concentrated under reduced pressure to obtain the title compound (800 mg). $^1$H-NMR (400 MHz, DMSOd$_6$) δ (ppm): 8.18 (d, J=8.0 Hz, 1H), 8.51 (dd, J=2.0, 8.0 Hz, 1H), 9.12-9.18 (m, 1H).

Preparation Example 8

Synthesis of 5-(methoxymethyl)pyrazine-2-carboxylic acid
(8-(2))

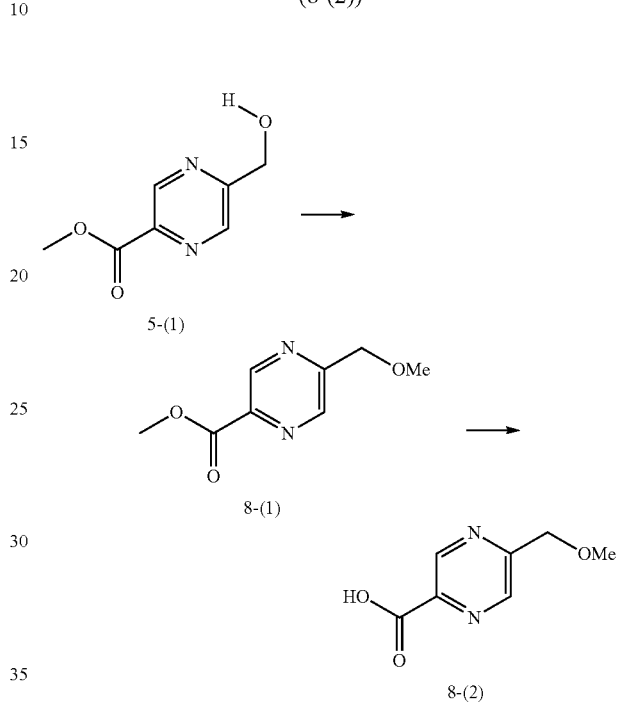

Synthesis of methyl 5-(methoxymethyl)pyrazine-2-carboxylate 8-(1)

The compound obtained in preparation example 5-(1) (279 mg) was dissolved in DMF and the solution was cooled to 0° C. Sodium hydride (60% in mineral oil, 70 mg) was added, followed by iodomethane (250 mg). After 2 days, water (25 mL) was added, and the solution extracted with EtOAc (100 mL). The aqueous layer was saturated with NaCl, and further extracted with EtOAc (2×50 mL). The combined organic portions were dried over MgSO$_4$, evaporated, and purified by silica gel chromatography (30% to 50% EtOAc in hexanes) to afford the title compound (55 mg, approx. purity 65%). $^1$H NMR (400 MHz, CDCl$_3$) δ ppm 3.55 (s, 3H), 4.05 (s, 3H), 4.72 (s, 2H), 8.84 (d, J=1.0 Hz, 1H), 9.25 (d, J=1.0 Hz, 1H)

Synthesis of 5-(methoxymethyl)pyrazine-2-carboxylic acid 8-(2)

Methyl 5-(methoxymethyl)pyrazine-2-carboxylate, 8-(1), (55 mg, crude) was dissolved in 1,4-dioxane (1 mL) and water (1 mL) was added followed by lithium hydroxide monohydrate (50 mg). After stirring at RT for 1 h, water (20 mL) was added and the mixture was extracted with ether (20 mL). The aqueous portion was acidified to pH 2 and extracted with EtOAc (2×25 mL). The combined EtOAc layers were dried over MgSO$_4$ and evaporated to afford the title compound (19 mg). ¹H NMR (400 MHz, CDCl₃) δ ppm 3.58 (s, 3H), 4.77 (s, 2H), 8.80 (br. s., 1H), 9.38 (br. s., 1H)

Preparation Example 9

5-Methoxypyrazine-2-carboxylic acid

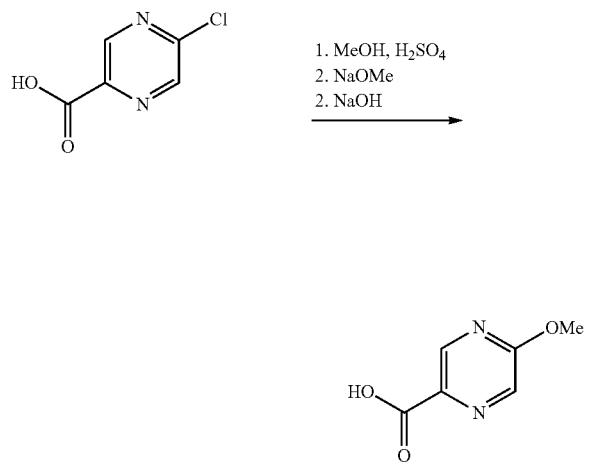

5-Chloropyrazine-2-carboxylic acid (5.0 g, 0.032 mol) was charged to a round-bottom flask equipped with a thermocouple, overhead stirrer and reflux condenser. Methanol (37.5 mL, 0.926 mol) was charged followed by conc. sulfuric acid (0.2 mL, 0.004 mol). The 3-neck flask was equipped with a heating mantle, and then the reaction mixture was heated to ca. 65.0° C. (T internal). The reaction mixture continued to stir at ca. 65.0° C. (T internal) for ca. 4 h. The reaction mixture cooled to ca. 25.8° C. (T internal). Methanol (12 mL, 0.31 mol) was charged and the slurry continued to stir at ca. 22.3° C. (T internal) for ca. 15 min then cooled to ca. 10.0° C. (T internal) under an atmosphere of nitrogen. 25% Sodium methoxide in methanol (1:3, Sodium methoxide:Methanol, 7.7 mL) was charged to flask while temperature remained below 30.0° C. (T internal). The reaction mixture was adjusted to 20.4° C. (T internal). After 30 min., sodium hydroxide (2.0 g, 0.04 mol) and water (37.5 mL, 2.08 mol) were combined to form a solution, and then the solution was charged to the reaction mixture. Water (50.0 mL, 2.78 mol) was charged and then the reaction mixture was heated to 40.0° C. (T internal) for ca. 60 mins. The heating mantle was removed, and then the reaction mixture cooled to ca. 25.4° C. (T internal). 38% aq. HCl Solution (38:62, hydrogen chloride:water, 4.0 mL) was added at a rate (ca. 5 min.) such that the temperature remained below 30.0° C. (T internal). The thick slurry was stirred for 1 h at ca. 21.4° C. (T internal), and then filtered over a sintered funnel. The solids were rinsed with water (10.0 mL, 0.555 mol) and dried under vacuum overnight to afford 5-methoxypyrazine-2-carboxylic acid (3.59 g). ¹H NMR (500 MHz, DMSO) δ 13.24 (1H, br s), 8.79 (1H, d, J=1.2 Hz), 8.37 (1H, d, J=1.2 Hz), 3.98 (s, 3H); ¹³C NMR (125 MHz, DMSO) δ 165.36, 161.88, 143.88, 136.82, 135.55, 54.69.

General procedure for the Coupling of Anilines Prepared in Preparation Examples 1-(13) and 2-(10) with aryl carboxylic Acids: Preparation of N-(3-((4aS,5S,7aS)-2-amino-5-(trifluoromethyl)-4a,5,7,7a-tetrahydro-4H-furo[3,4-d][1,3]thiazin-7a-yl)-4-fluorophenyl)-5-methoxypyrazine-2-carboxamide (Example 1)

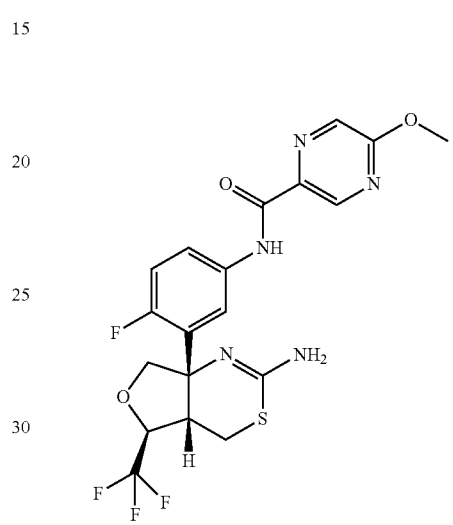

tert-Butyl ((4aS,5S,7aS)-7a-(5-amino-2-fluorophenyl)-5-(trifluoromethyl)-4a,5,7,7a-tetrahydro-4H-furo[3,4-d][1,3]thiazin-2-yl)carbamate (Preparation Example 1, 56 mg) was dissolved in DCM (2 mL) and 5-methoxypyrazine-2-carboxylic acid (40 mg), N,N-diisopropylethylamine (80 mg) and (1H-benzotriazol-1-yloxy)tripyrrolidin-1-yl)phosphonium hexafluorophosphate (135 mg) were added. The reaction mixture was stirred at RT for 18 h, and sodium bicarbonate (sat., aq., 25 mL) was added. The mixture was extracted with EtOAc (2×40 mL), the combined organic portions were dried over MgSO₄, evaporated and purified by silica gel chromatography (EtOAc/hexanes gradient) to afford the amide (40 mg) as a white solid. The amide was dissolved in DCM (2 mL) and TFA (1 mL) was added. After stirring at RT for 2 h, the reaction mixture was evaporated and sodium bicarbonate (sat., aq., 25 mL) was added. The mixture was extracted with EtOAc (2×25 mL), and the combined organic portions dried over MgSO₄ and evaporated to afford the title compound as a white solid (34 mg). ¹H NMR (400 MHz, CDCl₃) δ ppm 2.78-2.87 (m, 1H), 3.11-3.21 (m, 1H), 3.38-3.48 (m, 1H), 3.82-4.06 (m, 4H), 4.48-4.72 (m, 2H), 6.96-7.10 (m, 1H), 7.52 (d, J=4.8 Hz, 1H), 7.87 (d, J=8.8 Hz, 1H), 8.09 (s, 1H), 8.95 (s, 1H), 9.46 (br. s., 1H)

Example 2

N-(3-((4aS,5S,7aS)-2-amino-5-(trifluoromethyl)-4a,5,7,7a-tetrahydro-4H-furo[3,4-d][1,3]thiazin-7a-yl)-4-fluorophenyl)-5-cyanopicolinamide

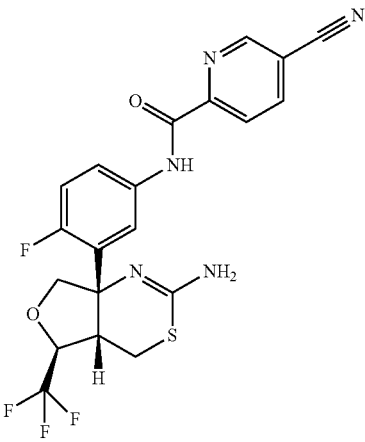 [SMILES: N#Cc1ccc(C(=O)Nc2ccc(F)c([C@]34CO[C@H](C(F)(F)F)[C@H]3CSC(N)=N4)c2)nc1]

Synthesized from tert-butyl [(4aS,5S,7aS)-7a-(5-amino-2-fluorophenyl)-5-trifluoromethyl-4a,5,7,7a-tetrahydro-4H-furo[3,4-d][1,3]thiazin-2-yl]carbamate and 5-cyanopyrazine-2-carboxylic acid according to the general procedure. ¹H NMR (400 MHz, CDCl₃) δ ppm 2.82 (dd, J=13.6, 3.5 Hz, 1H), 3.14-3.21 (m, 1H), 3.37-3.45 (m, 1H), 3.91 (d, J=9.1 Hz, 1H), 4.50-4.71 (m, 2H), 7.08 (dd, J=11.9, 8.8 Hz, 1H), 7.46-7.57 (m, 1H), 7.92 (dt, J=8.8, 3.4 Hz, 1H), 8.17 (dd, J=8.3, 2.0 Hz, 1H), 8.34 (d, J=8.1 Hz, 1H), 8.81-8.92 (m, 1H)

Example 3

N-(3-((4aS,5S,7aS)-2-amino-5-(trifluoromethyl)-4a,5,7,7a-tetrahydro-4H-furo[3,4-d][1,3]thiazin-7a-yl)-4-fluorophenyl)-5-(difluoromethyl)pyrazine-2-carboxamide

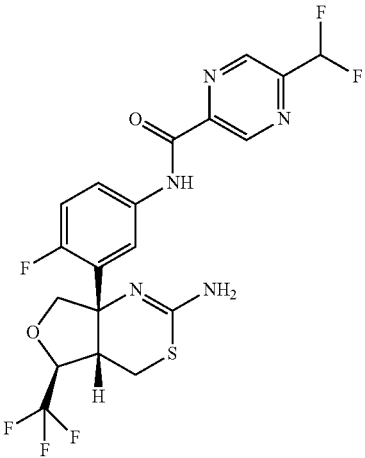 [SMILES: NC1=N[C@@]2(c3cc(NC(=O)c4cnc(C(F)F)cn4)ccc3F)CO[C@H](C(F)(F)F)[C@H]2CS1]

Synthesized from tert-butyl [(4aS,5S,7aS)-7a-(5-amino-2-fluorophenyl)-5-trifluoromethyl-4a,5,7,7a-tetrahydro-4H-furo[3,4-d][1,3]thiazin-2-yl]carbamate and 5-difluoromethyl-pyrazine-2-carboxylic acid according to the general procedure. ¹H NMR (400 MHz, CDCl₃) δ ppm 2.80 (dd, J=13.8, 3.7 Hz, 1H), 3.11 (dd, J=13.6, 2.8 Hz, 1H), 3.31-3.41 (m, 1H), 3.86 (d, J=8.3 Hz, 1H), 4.57 (d, J=8.3 Hz, 1H), 4.64 (dt, J=14.7, 7.1 Hz, 1H), 4.75 (br s, 2H), 6.69 (t, J=56.3 Hz, 1H), 7.07 (dd, J=11.6, 8.8 Hz, 1H), 7.57 (dd, J=7.1, 2.8 Hz, 1H), 7.87 (dt, J=8.5, 3.6 Hz, 1H), 8.85 (s, 1H), 9.45 (s, 1H), 9.58 (br. s., 1H)

Example 4

N-(3-((4aS,5S,7aS)-2-amino-5-(trifluoromethyl)-4a,5,7,7a-tetrahydro-4H-furo[3,4-d][1,3]thiazin-7a-yl)-4-fluorophenyl)-5-(trifluoromethyl)picolinamide

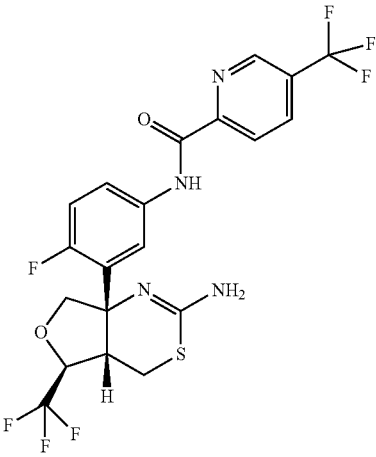 [SMILES: NC1=N[C@@]2(c3cc(NC(=O)c4ccc(C(F)(F)F)cn4)ccc3F)CO[C@H](C(F)(F)F)[C@H]2CS1]

Synthesized from tert-butyl [(4aS,5S,7aS)-7a-(5-amino-2-fluorophenyl)-5-trifluoromethyl-4a,5,7,7a-tetrahydro-4H-furo[3,4-d][1,3]thiazin-2-yl]carbamate and 5-trifluoromethyl-pyridine-2-carboxylic acid according to the general procedure. ¹H NMR (400 MHz, CDCl₃) δ ppm 2.88 (dd, J=13.6, 3.8 Hz, 1H), 3.20 (dd, J=13.6, 3.0 Hz, 1H), 3.37-3.53 (m, 1H), 3.94 (dd, J=8.3, 2.3 Hz, 1H), 4.40-4.89 (m, 4H), 7.14 (dd, J=11.9, 8.8 Hz, 1H), 7.66 (dd, J=6.8, 2.8 Hz, 1H), 7.98 (ddd, J=8.8, 4.0, 3.0 Hz, 1H), 8.20 (dd, J=8.2, 1.6 Hz, 1H), 8.45 (d, J=8.3 Hz, 1H), 8.90 (s, 1H), 9.95 (s, 1H)

Example 5

N-(3-((4aS,5S,7aS)-2-amino-5-(trifluoromethyl)-4a,5,7,7a-tetrahydro-4H-furo[3,4-d][1,3]thiazin-7a-yl)-4-fluorophenyl)-5-methylpyrazine-2-carboxamide

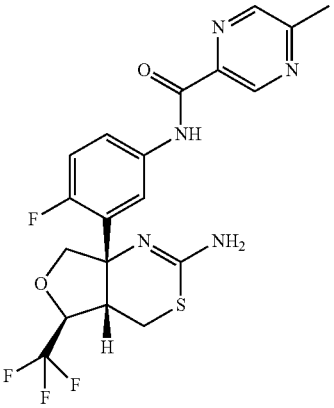

Synthesized from tert-butyl [(4aS,5S,7aS)-7a-(5-amino-2-fluorophenyl)-5-trifluoromethyl-4a,5,7,7a-tetrahydro-4H-furo[3,4-d][1,3]thiazin-2-yl]carbamate and 5-methyl-pyrazine-2-carboxylic acid according to the general procedure.

¹H NMR (400 MHz, CDCl₃) δ ppm 2.72 (s, 3H), 2.88 (dd, J=13.6, 3.8 Hz, 1H), 3.21 (dd, J=13.6, 3.0 Hz, 1H), 3.42-3.49 (m, 1H), 3.94 (d, J=8.3 Hz, 1H), 4.39-4.80 (m, 4H), 7.14 (dd, J=11.9, 8.8 Hz, 1H), 7.62 (dd, J=7.1, 2.8 Hz, 1H), 7.93-7.99 (m, 1H), 8.46 (d, J=1.0 Hz, 1H), 9.39 (d, J=1.3 Hz, 1H), 9.65 (s, 1H)

Example 6

N-(3-((4aS,5S,7a5)-2-amino-5-(trifluoromethyl)-4a,5,7,7a-tetrahydro-4H-furo[3,4-d][1,3]thiazin-7a-yl)-4-fluorophenyl)-5-methylpicolinamide

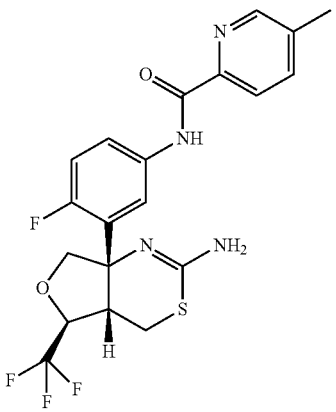 [SMILES: Cc1ccc(C(=O)Nc2ccc(F)c([C@]34CO[C@H](C(F)(F)F)[C@H]3CSC(N)=N4)c2)nc1]

Synthesized from tert-butyl [(4aS,5S,7aS)-7a-(5-amino-2-fluorophenyl)-5-trifluoromethyl-4a,5,7,7a-tetrahydro-4H-furo[3,4-d][1,3]thiazin-2-yl]carbamate and 5-methyl-pyridine-2-carboxylic acid according to the general procedure. ¹H NMR (400 MHz, CDCl₃) δ ppm 2.37 (s, 3H), 2.78 (dd, J=13.6, 3.8 Hz, 1H), 3.12 (dd, J=13.6, 2.8 Hz, 1H), 3.28-3.40 (m, 1H), 3.87 (d, J=8.1 Hz, 1H), 4.28-5.02 (m, 4H), 7.02 (dd, J=11.9, 8.8 Hz, 1H), 7.55 (dd, J=7.1, 2.8 Hz, 1H), 7.63 (dd, J=8.0, 1.4 Hz, 1H), 7.88 (ddd, J=8.8, 4.0, 2.9 Hz, 1H), 8.10 (d, J=8.1 Hz, 1H), 8.31-8.40 (m, 1H), 9.90 (s, 1H)

Example 7

N-(3-((4aS,5S,7a5)-2-amino-5-(trifluoromethyl)-4a,5,7,7a-tetrahydro-4H-furo[3,4-d][1,3]thiazin-7a-yl)-4-fluorophenyl)-5-ethylpicolinamide

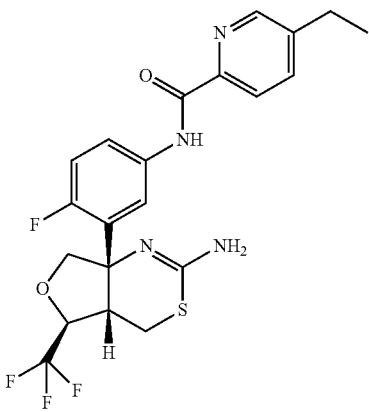 [SMILES: CCc1ccc(C(=O)Nc2ccc(F)c([C@]34CO[C@H](C(F)(F)F)[C@H]3CSC(N)=N4)c2)nc1]

Synthesized from tert-butyl [(4aS,5S,7aS)-7a-(5-amino-2-fluorophenyl)-5-trifluoromethyl-4a,5,7,7a-tetrahydro-4H-furo[3,4-d][1,3]thiazin-2-yl]carbamate and 5-ethyl-pyridine-2-carboxylic acid according to the general procedure. ¹H NMR (400 MHz, CDCl₃) δ ppm 1.33 (t, J=7.6 Hz, 3H), 2.78 (q, J=7.6 Hz, 2H), 2.88 (dd, J=13.5, 3.7 Hz, 1H), 3.22 (dd, J=13.6, 2.8 Hz, 1H), 3.42-3.48 (m, 1H), 3.96 (d, J=7.3 Hz, 1H), 4.44-4.95 (m, 4H), 7.12 (dd, J=11.6, 8.8 Hz, 1H), 7.62 (dd, J=6.9, 2.7 Hz, 1H), 7.74 (dd, J=8.1, 1.8 Hz, 1H), 7.98 (dt, J=8.7, 3.5 Hz, 1H), 8.21 (d, J=8.1 Hz, 1H), 8.44-8.48 (m, 1H), 10.00 (s, 1H)

Example 8

N-(3-((4aS,5S,7a5)-2-amino-5-(trifluoromethyl)-4a,5,7,7a-tetrahydro-4H-furo[3,4-][1,3]thiazin-7a-yl)-4-fluorophenyl)-5-(fluoromethyl)pyrazine-2-carboxamide

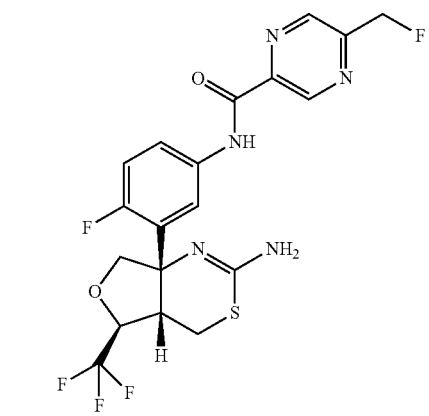 [SMILES: NC1=N[C@@]2(c3cc(NC(=O)c4cnc(CF)cn4)ccc3F)CO[C@H](C(F)(F)F)[C@H]2CS1]

Synthesized from tert-butyl [(4aS,5S,7aS)-7a-(5-amino-2-fluorophenyl)-5-trifluoromethyl-4a,5,7,7a-tetrahydro-4H-furo[3,4-d][1,3]thiazin-2-yl]carbamate and 5-fluoromethyl-pyrazine-2-carboxylic acid according to the general procedure. Details of an actual preparation are as follows:- tert-Butyl ((4aS,5S,7aS)-7a-(5-amino-2-fluorophenyl)-5-(trifluoromethyl)-4a,5,7,7a-tetrahydro-4H-furo[3,4-d][1,3]thiazin-2-yl)carbamate (500 mg) was dissolved in DCM (10 mL) and 5-fluoromethyl-pyrazine-2-carboxylic acid (223 mg), N,N-diisopropylethylamine (521 mg) and (1H-benzotriazol-1-yloxy)tripyrrolidin-1-yl)phosphonium hexafluorophophate (750 mg) were added. The reaction mixture was stirred at RT for 1 h, and sodium bicarbonate (sat., aq., 50 mL) was added. The mixture was extracted with EtOAc (2×75 mL), the combined organic portions were dried over MgSO₄, evaporated and purified by silica gel chromatography (0% to 30% EtOAc/hexanes gradient) to afford the amide (613 mg) as a white solid. The amide was dissolved in DCM (2 mL) and TFA (1 mL) was added. After stirring at RT for 2 h, the reaction mixture was evaporated and sodium bicarbonate (sat., aq., 25 mL) was added. The mixture was extracted with EtOAc (3×25 mL), and the combined organic portions dried over MgSO₄ and evaporated to afford the title compound as a white solid ¹H NMR (400 MHz, CDCl₃) δ ppm 2.89 (dd, J=13.8, 3.7 Hz, 1H), 3.21 (dd, J=13.9, 2.5 Hz, 1H), 3.40-3.51 (m, 1H), 3.96 (d, J=7.3 Hz, 1H), 4.42-4.85 (m, 4H), 5.69 (d, J=46.5 Hz, 2H), 7.15 (dd, J=11.9, 8.8 Hz, 1H), 7.64 (dd, J=7.1, 2.8 Hz, 1H), 7.94-8.00 (m, 1H), 8.77 (s, 1H), 9.47 (s, 1H), 9.68 (s, 1H)

Example 9

N-(3-((4aS,5S,7aS)-2-amino-5-(trifluoromethyl)-4a,5,7,7a-tetrahydro-4H-furo[3,4-d][1,3]thiazin-7a-yl)-4-fluorophenyl)-5-methoxypicolinamide

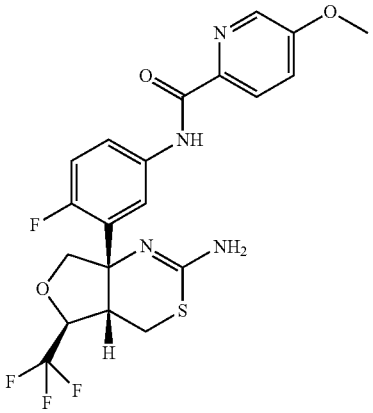 [SMILES: COc1ccc(C(=O)Nc2ccc(F)c([C@]34CO[C@H](C(F)(F)F)[C@H]3CSC(N)=N4)c2)nc1]

Synthesized from tert-butyl [(4aS,5S,7aS)-7a-(5-amino-2-fluorophenyl)-5-trifluoromethyl-4a,5,7,7a-tetrahydro-4H-furo[3,4-d][1,3]thiazin-2-yl]carbamate and 5-methoxypyridine-2-carboxylic acid according to the general procedure. $^1$H NMR (400 MHz, CDCl$_3$) δ ppm 2.88 (dd, J=13.8, 3.7 Hz, 1H), 3.23 (dd, J=13.8, 2.4 Hz, 1H), 3.46 (d, J=7.3 Hz, 1H), 3.89-4.02 (m, 4H), 4.54-5.00 (m, 4H), 7.11 (dd, J=11.9, 8.8 Hz, 1H), 7.36 (dd, J=8.8, 2.8 Hz, 1H), 7.61 (dd, J=7.1, 2.8 Hz, 1H), 7.97 (dt, J=8.5, 3.6 Hz, 1H), 8.23-8.30 (m, 2H), 9.86 (s, 1H)

Example 10

N-(3-((4aS,5S,7aS)-2-amino-5-(trifluoromethyl)-4a,5,7,7a-tetrahydro-4H-furo[3,4-d][1,3]thiazin-7a-yl)-4-fluorophenyl)-5-ethoxypyrazine-2-carboxamide

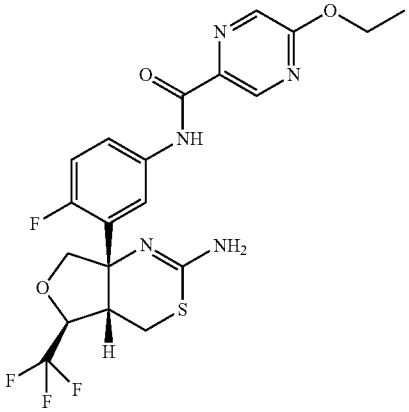 [SMILES: CCOc1cnc(C(=O)Nc2ccc(F)c([C@]34CO[C@H](C(F)(F)F)[C@H]3CSC(N)=N4)c2)cn1]

Synthesized from tert-butyl [(4aS,5S,7aS)-7a-(5-amino-2-fluorophenyl)-5-trifluoromethyl-4a,5,7,7a-tetrahydro-4H-furo[3,4-d][1,3]thiazin-2-yl]carbamate and 5-ethoxypyrimidine-2-carboxylic acid according to the general procedure. $^1$H NMR (400 MHz, CDCl$_3$) δ ppm 1.47 (t, J=7.1 Hz, 3H), 2.87 (dd, J=13.6, 3.5 Hz, 1H), 3.20 (d, J=13.6 Hz, 1H), 3.40-3.50 (m, 1H), 3.94 (d, J=7.8 Hz, 1H), 4.46-4.95 (m, 6H), 7.11 (dd, J=11.5, 9.0 Hz, 1H), 7.54-7.63 (m, 1H), 7.90-8.01 (m, 1H), 8.13 (s, 1H), 9.00 (s, 1H), 9.52 (br. s., 1H)

Example 11

N-(3-((4aS,5S,7aS)-2-amino-5-(trifluoromethyl)-4a,5,7,7a-tetrahydro-4H-furo[3,4-d][1,3]thiazin-7a-yl)-4-fluorophenyl)-5-(1,1-difluoroethyl)pyrazine-2-carboxamide

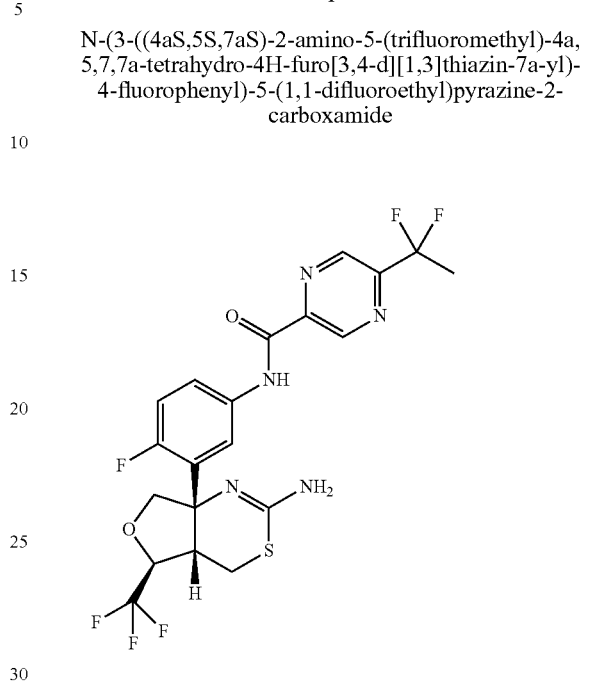

Synthesized from tert-butyl [(4aS,5S,7aS)-7a-(5-amino-2-fluorophenyl)-5-trifluoromethyl-4a,5,7,7a-tetrahydro-4H-furo[3,4-d][1,3]thiazin-2-yl]carbamate and 5-(1,1-difluoroethyl)pyrazine-2-carboxylic acid according to the general procedure. $^1$H NMR (600 MHz, CDCl$_3$) δ ppm 2.03 (t, J=18.8 Hz, 3H), 2.82 (d, J=12.0 Hz, 1H), 3.14 (d, J=12.4 Hz, 1H), 3.35-3.46 (m, 1H), 3.77-4.07 (m, 1H), 4.20-4.93 (m, 4H), 7.08 (dd, J=11.7, 9.0 Hz, 1H), 7.56 (d, J=4.5 Hz, 1H), 7.80-7.93 (m, 1H), 8.87 (s, 1H), 9.43 (s, 1H), 9.59 (br. s., 1H)

Example 12

N-(3-((4aS,5S,7aS)-2-amino-5-(trifluoromethyl)-4a,5,7,7a-tetrahydro-4H-furo[3,4-d][1,3]thiazin-7a-yl)-4-fluorophenyl)-5-(trifluoromethyl)pyrazine-2-carboxamide

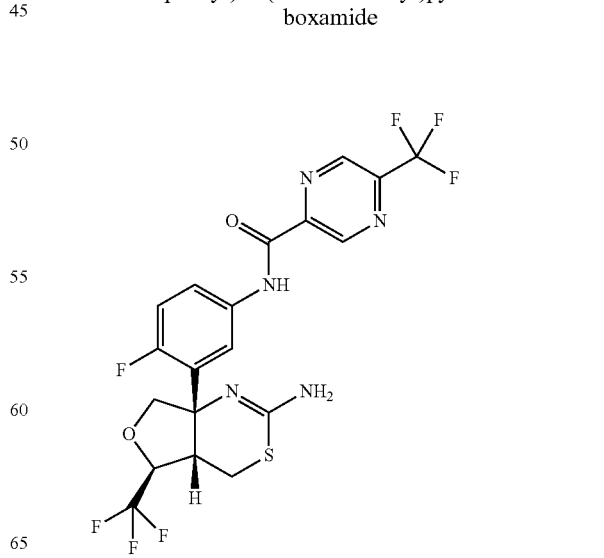

Synthesized from tert-butyl [(4aS,5S,7aS)-7a-(5-amino-2-fluorophenyl)-5-trifluoromethyl-4a,5,7,7a-tetrahydro-4H-furo[3,4-d][1,3]thiazin-2-yl]carbamate and 5-trifluoromethylpyrazine-2-carboxylic acid according to the general procedure. $^1$H NMR (400 MHz, CDCl$_3$) δ ppm 2.80 (dd, J=13.6, 3.8 Hz, 1H), 3.11 (dd, J=13.8, 2.9 Hz, 1H), 3.30-3.44 (m, 1H), 3.87 (d, J=8.3 Hz, 1H), 4.25-5.14 (m, 4H), 7.07 (dd, J=11.9, 8.8 Hz, 1H), 7.57 (dd, J=6.8, 2.8 Hz, 1H), 7.86 (dt, J=8.4, 3.6 Hz, 1H), 8.89 (s, 1H), 9.53 (s, 2H)

Example 13

N-(3-((4aS,5S,7aS)-2-amino-5-(trifluoromethyl)-4a,5,7,7a-tetrahydro-4H-furo[3,4-d][1,3]thiazin-7a-yl)-4-fluorophenyl)-5-(methoxymethyl)pyrazine-2-carboxamide

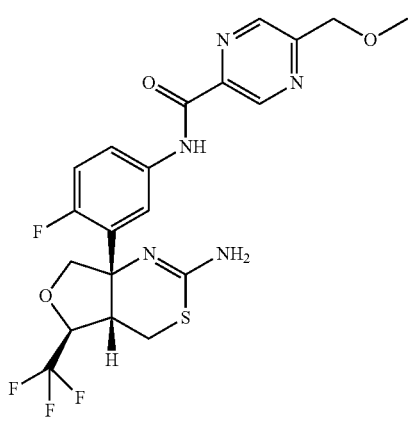 [SMILES: COCc1cnc(C(=O)Nc2ccc(F)c([C@]34CO[C@H](C(F)(F)F)[C@H]3CSC(N)=N4)c2)cn1]

Synthesized from tert-butyl [(4aS,5S,7aS)-7a-(5-amino-2-fluorophenyl)-5-trifluoromethyl-4a,5,7,7a-tetrahydro-4H-furo[3,4-d][1,3]thiazin-2-yl]carbamate and 5-(methoxymethyl)pyrimidine-2-carboxylic acid according to the general procedure. $^1$H NMR (400 MHz, CDCl$_3$) δ ppm 2.79 (dd, J=13.6, 3.8 Hz, 1H), 3.11 (dd, J=13.6, 2.8 Hz, 1H), 3.32-3.39 (m, 1H), 3.49 (s, 3H), 3.84 (d, J=8.3 Hz, 1H), 4.34-4.73 (m, 6 H), 7.05 (dd, J=11.6, 8.8 Hz, 1H), 7.55 (dd, J=6.8, 2.8 Hz, 1H), 7.88 (dt, J=8.4, 3.6 Hz, 1H), 8.63 (s, 1H), 9.34 (d, J=1.0 Hz, 1H), 9.60 (s, 1H)

Example 14

N-{3-[(4aS,5S,7aS)-2-amino-5-(trifluoromethyl)-4a,5-dihydro-4H-furo[3,4 d][1,3]thiazin-7a(7H)-yl]-4-fluorophenyl}-5-[($^2$H$_3$)methyloxy]pyrazine-2-carboxamide Synthesis of 14-(2) 5-[($^2$H$_3$)methyloxy]pyrazine-2-carboxylic acid

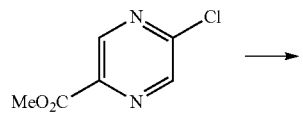

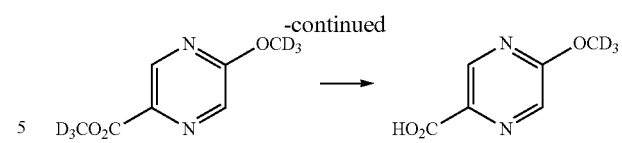

Part (I): ($^2$H$_3$)methyl 5-[($^2$H$_3$)methyloxy]pyrazine-2-carboxylate

Freshly cut sodium metal (160 mg) was added portionwise over 10 mins to ($^2$H$_3$)methan($^2$H)ol (5 mL) and the solution was stirred until the sodium had dissolved. This solution was then added to methyl 5-chloropyrazine-2-carboxylate (1.02 g) in ($^2$H$_3$)methan($^2$H)ol (5 mL) and the solution was allowed to stir at RT for 1 hr. The solution was then concentrated under reduced pressure to a volume of about 2 mL, and water (50 mL) was added. The mixture was extracted with EtOAc (2×50 mL), the combined organic portions were dried over MgSO$_4$ and evaporated to afford the title compound (745 mg). $^1$H NMR (400 MHz, CDCl$_3$) δ ppm 8.30 (d, J=1.3 Hz, 1H), 8.91 (d, J=1.3 Hz, 1H)

Part (II): 5-[($^2$H$_3$)methyloxy]pyrazine-2-carboxylic acid

To a stirred solution of ($^2$H$_3$)methyl 5-[($^2$H$_3$)methyloxy] pyrazine-2-carboxylate in 1,4-dioxane (5 mL) was added water (5 mL) followed by lithium hydroxide monohydrate (300 mg). After stirring for 1 hr, the reaction mixture was concentrated under reduced pressure to about 5 mL and extracted with diethyl ether (25 mL). The organic layer was extracted with 1N NaOH (aq., 10 mL), and the combined aqueous portions were acidified to pH 2 with 6N hydrochloric acid. After cooling in a fridge, the mixture was filtered to afford the title compound as a pale brown powder (660 mg). $^1$H NMR (400 MHz, CDCl$_3$) δ ppm 8.21 (d, J=1.3 Hz, 1H), 9.01 (d, J=1.3 Hz, 1H), 10.12 (br s., 1H)

Part (III): N-{3-[(4aS,5S,7aS)-2-amino-5-(trifluoromethyl)-4a,5-dihydro-4H-furo[3,4 d][1,3]thiazin-7a(7H)-yl]-4-fluorophenyl}-5-[($^2$H$_3$)methyloxy]pyrazine-2-carboxamide

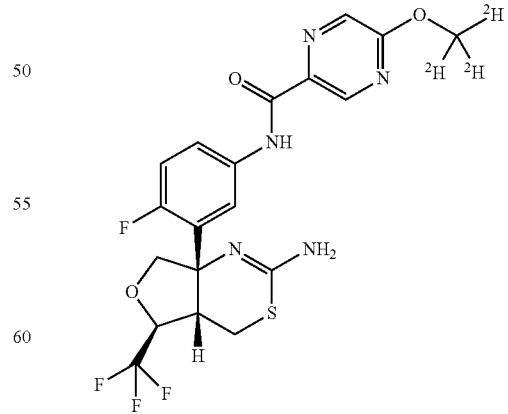

tert-Butyl ((4aS,5S,7aS)-7a-(5-amino-2-fluorophenyl)-5-(trifluoromethyl)-4a,5,7,7a-tetrahydro-4H-furo[3,4-d][1,3]thiazin-2-yl)carbamate (100 mg) was dissolved in DCM (2 mL) and 5-[(²H₃)methyloxy]pyrazine-2-carboxylic acid (55 mg), N,N-diisopropylethylamine (112 mg) and (1H-benzotriazol-1-yloxy)tripyrrolidin-1-yl)phosphonium hexafluorophosphate (180 mg) were added. The reaction mixture was stirred at RT for 18 h, and sodium bicarbonate (sat., aq., 25 mL) was added. The mixture was extracted with EtOAc (2×40 mL), the combined organic portions were dried over MgSO₄, evaporated and purified by silica gel chromatography (2% to 25% EtOAc in hexanes) to afford the amide (127 mg) as a white solid. The amide was dissolved in DCM (2 mL) and TFA (1 mL) was added. After stirring at RT for 2 h, the reaction mixture was evaporated and sodium bicarbonate (sat., aq., 25 mL) was added. The mixture was extracted with EtOAc (2×40 mL), and the combined organic portions dried over MgSO₄ and evaporated to afford the title compound as a white solid (104 mg). ¹H NMR (400 MHz, CDCl₃) δ ppm 2.87 (dd, J=13.6, 3.8 Hz, 1H), 3.21 (dd, J=13.6, 2.8 Hz, 1H), 3.39-3.53 (m, 1H), 3.95 (d, J=8.3 Hz, 1H), 4.65 (d, J=8.3 Hz, 1H), 4.72 (quin, J=7.2 Hz, 1H), 4.87 (br s, 2H), 7.12 (dd, J=11.9, 8.8 Hz, 1H), 7.60 (dd, J=6.9, 2.7 Hz, 1H), 7.95 (dt, J=8.5, 3.6 Hz, 1H), 8.16 (d, J=1.0 Hz, 1H), 9.02 (d, J=1.0 Hz, 1H), 9.52 (s, 1H)

Example 15

N-(3-((4aS,5S,7aS)-2-amino-5-(trifluoromethyl)-4a,5,7,7a-tetrahydro-4H-furo[3,4-d][1,3]thiazin-7a-yl)-4,5-difluorophenyl)-5-(difluoromethyl)pyrazine-2-carboxamide

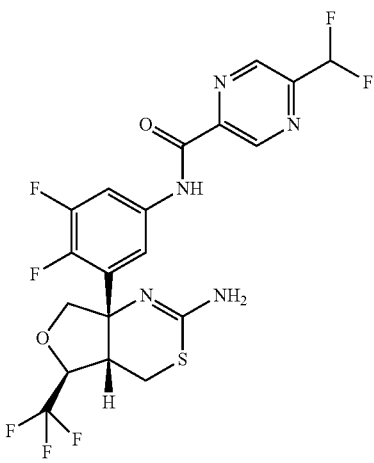 [SMILES: NC1=N[C@@]2(c3cc(NC(=O)c4cnc(C(F)F)cn4)cc(F)c3F)CO[C@H](C(F)(F)F)[C@H]2CS1]

Synthesized from tert-butyl [(4aS,5S,7aS)-7a-(5-amino-2,3-difluorophenyl)-5-trifluoromethyl-4a,5,7,7a-tetrahydro-4H-furo[3,4-d][1,3]thiazin-2-yl]carbamate and 5-difluoromethyl-pyrazine-2-carboxylic acid according to the general procedure. ¹H NMR (400 MHz, CDCl₃) δ ppm 2.90 (dd, J=13.8, 3.7 Hz, 1H), 3.19 (dd, J=13.8, 2.7 Hz, 1H), 3.31-3.49 (m, 1H), 3.95 (d, J=7.6 Hz, 1H), 4.44-5.15 (m, 4H), 6.81 (t, J=55.8 Hz, 4H), 7.22-7.35 (m, 1H), 8.08 (ddd, J=11.2, 6.8, 2.7 Hz, 1H), 8.94 (s, 1H), 9.53 (s, 1H), 9.67 (s, 1H)

Example 16

N-(3-((4aS,5S,7aS)-2-amino-5-(trifluoromethyl)-4a,5,7,7a-tetrahydro-4H-furo[3,4-d][1,3]thiazin-7a-yl)-4,5-difluorophenyl)-5-methoxypyrazine-2-carboxamide

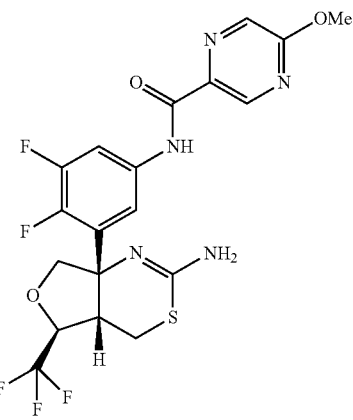

Synthesized from tert-butyl [(4aS,5S,7aS)-7a-(5-amino-2,3-difluorophenyl)-5-trifluoromethyl-4a,5,7,7a-tetrahydro-4H-furo[3,4-d][1,3]thiazin-2-yl]carbamate and 5-methoxypyrazine-2-carboxylic acid according to the general procedure. ¹H NMR (400 MHz, CDCl₃+MeOD) δ ppm 2.83 (dd, J=13.9, 3.8 Hz, 1H), 3.14 (dd, J=13.9, 3.0 Hz, 1H), 3.29-3.39 (m, 1H), 3.87 (d, J=8.3 Hz, 1H), 4.04 (s, 3H), 4.60 (d, J=8.3 Hz, 1H), 4.67 (quin, J=6.3 Hz, 1H), 7.11-7.21 (m, 1H), 8.03 (ddd, J=11.6, 6.9, 2.7 Hz, 1H), 8.15 (d, J=1.3 Hz, 1H), 8.96 (d, J=1.3 Hz, 1H)

Example 17

N-(3-((4aS,5S,7aS)-2-amino-5-(trifluoromethyl)-4a,5,7,7a-tetrahydro-4H-furo[3,4-d][1,3]thiazin-7a-yl)-4,5-difluorophenyl)-5-methylpyrazine-2-carboxamide

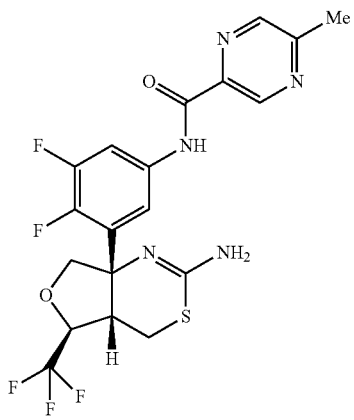 [SMILES: Cc1cnc(C(=O)Nc2cc(F)c(F)c([C@]34CO[C@H](C(F)(F)F)[C@H]3CSC(N)=N4)c2)cn1]

Synthesized from tert-butyl [(4aS,5S,7aS)-7a-(5-amino-2,3-difluorophenyl)-5-trifluoromethyl-4a,5,7,7a-tetrahydro-4H-furo[3,4-d][1,3]thiazin-2-yl]carbamate and 5-methylpyrazine-2-carboxylic acid according to the general procedure. ¹H NMR (400 MHz, CDCl₃+MeOD) δ ppm 2.68 (s, 3H), 2.84 (dd, J=13.6, 3.8 Hz, 1H), 3.15 (dd, J=13.9, 3.0 Hz, 1H), 3.30-3.42 (m, 1H), 3.88 (d, J=10.4 Hz, 1H), 4.61 (d, J=8.6 Hz, 1H), 4.68 (quin, J=7.2 Hz, 1H), 7.13-7.25 (m, 1H), 8.05 (ddd, J=11.6, 6.8, 2.8 Hz, 1H), 8.46 (s, 1H), 9.30 (d, J=1.3 Hz, 1H)

Example 18

N-(3-((4aS,5S,7aS)-2-amino-5-(trifluoromethyl)-4a,5,7,7a-tetrahydro-4H-furo[3,4-d][1,3]thiazin-7a-yl)-4,5-difluorophenyl)-5-(fluoromethyl)-pyrazine-2-carboxamide

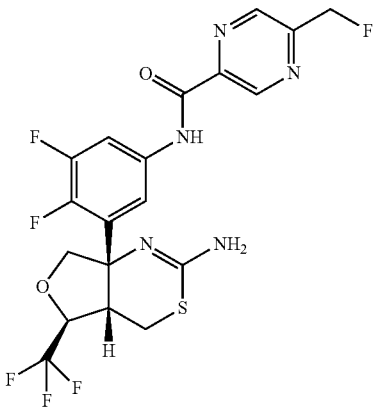 [SMILES: NC1=N[C@@]2(c3cc(NC(=O)c4cnc(CF)cn4)cc(F)c3F)CO[C@H](C(F)(F)F)[C@H]2CS1]

Synthesized from tert-butyl [(4aS,5S,7aS)-7a-(5-amino-2,3-difluorophenyl)-5-trifluoromethyl-4a,5,7,7a-tetrahydro-4H-furo[3,4-d][1,3]thiazin-2-yl]carbamate and 5-(fluoromethyl)pyrazine-2-carboxylic acid according to the general procedure. ¹H NMR (400 MHz, CDCl₃) δ ppm 2.89 (dd, J=13.6, 3.8 Hz, 1H), 3.19 (dd, J=13.6, 3.0 Hz, 1H), 3.43 (dd, J=7.5, 3.4 Hz, 1H), 3.86-3.99 (m, 1H), 4.39-4.67 (m, 3H), 4.74 (quin, J=7.1 Hz, 1H), 5.76 (d, J=45.5 Hz, 2H), 8.10 (ddd, J=11.4, 6.8, 2.8 Hz, 1H), 8.77 (s, 1H), 9.46 (s, 1H), 9.69 (s, 1H)

Alternate Preparations of the compounds of Examples 1 and 8 are described herein below. For these alternate preparations ¹H NMR and ¹³C NMR spectra were recorded on a Varian 400 MHz or 500 MHz instrument with vNMR 6.1C software.

Alternative Preparation of N-(3-((4aS,5S,7aS)-2-amino-5-(trifluoromethyl)-4a,5,7,7a-tetrahydro-4H-furo[3,4-d][1,3]thiazin-7a-yl)-4-fluorophenyl)-5-methoxypyrazine-2-carboxamide (Example 1)

1-(14) Synthesis of ten-Butyl 2-(1,1,1-trifluorobut-3-en-2-yloxy)acetate

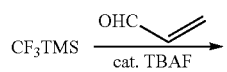

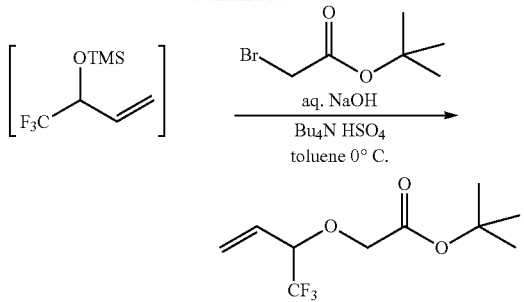

A reaction vessel was charged with toluene (3.2 L), THF (0.60 L) and acrolein (0.40 L, 5.985 mol) at rt under nitrogen. (Trifluoromethyl)trimethylsilane (1.003 kg, 7.059 mol) was added at 17° C. The reaction mixture was cooled to 2.5° C. and TBAF (0.01 M in THF, 0.400 L, 0.004 mol) was added over 2 h. During addition of TBAF, the temperature of the reaction mixture increased to 65° C. The reaction mixture was cooled to 0° C., and after 2 h, tetra-n-butylammonium hydrogen sulfate (0.171 kg, 0.503 mol) was added, followed by tert-butyl bromoacetate (0.987 kg, 5.064 mol). Sodium hydroxide (50% wt in water, 4.2 kg, 52.6 mol) was added over 2 h while maintaining the temperature under 10° C. After 2 h at 0-5° C., to the reaction mixture was added water (2.9 L) and methyl tert-butyl ether (6.0 L). The aq. phase was extracted one more time with methyl tert-butyl ether (6.0 L). The organic phases were combined and washed with 14% aq. NaCl (3×1.6 L). The organics were concentrated under vacuum to afford the title compound as an oil (1.150 kg, 94.5%) which was used in the subsequent stage without additional purification. ¹H NMR (500 MHz, CDCl₃) δ ppm 5.86-5.74 (m, 1H), 5.59 (d, J=17.5 Hz, 1H), 5.56 (d, J=10.9 Hz, 1H), 4.37-4.30 (m, 1H), 4.11 (d, J=16.5 Hz, 1H), 4.06 (d, J=16.4 Hz, 1H), 1.40 (s, 9H); ¹³C NMR (125 MHz, CDCl₃) δ ppm 168.51, 128.49 (d, J=1.7 Hz), 123.86, 123.71 (q, J=281.8 Hz), 82.22, 78.67 (q, J=31.5 Hz), 66.60, 28.02.

1-(15) Synthesis of N-Methoxy-N-methyl-2-(1,1,1-trifluorobut-3-en-2-yloxy)acetamide

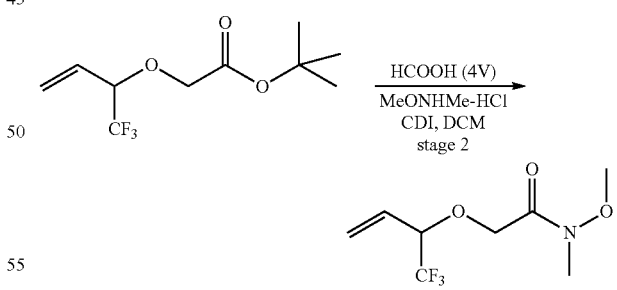

To a reactor containing tert-butyl 2-(1,1,1-trifluorobut-3-en-2-yloxy)acetate (1.150 kg, 4.788 mol) was added formic acid (6.2 kg) at rt. The reaction mixture was heated to 55-60° C. for 4-5 h. The formic acid was evaporated under vacuum (T=40-45° C.) and chased with toluene (2×3.0 L). To the residue was added CH₂Cl₂ (2.0 L) and further concentrated under vacuum. To the resulting residue was added CH₂Cl₂ (4.6 L) and the solution was cooled to 0° C., followed by N,N-carbonyldiimidazole (1.05 kg, 6.49 mol) in five portions. The mixture was stirred for 30 mins, and N,O-dimethylhydroxylamine hydrochloride (0.67 kg, 6.72 mol) was added in portions while maintaining temperature below 10° C. The reaction mixture was warmed to rt and stirred over 14 h. The reaction mixture was cooled to 3.2° C. and imidazole (100.7 g, 1.48 mol) was charged in two portions. The reaction mixture was warmed to rt and water (1.4 kg) was added, followed by methyl tert-butyl ether (14.0 L). The organic phase was washed with 2.0 N aq. HCl (1.0 L and 0.7 L), followed by sat. aq. NaHCO$_3$ (1.2 L) and sat. aq. NaCl (1.20 L). The organics were concentrated to afford the title compound as an oil (0.95 kg, 87.2%). $^1$H NMR (500 MHz, CDCl$_3$) δ ppm 5.85-5.76 (m, 1H), 5.62 (d, J=17.2 Hz, 1H), 5.56 (d, J=10.4 Hz, 1H), 4.49-4.34 (m, 3H), 3.68 (s, 3H), 3.67 (s, 1H), 3.18 (s, 3H), 3.08 (s, 1H); $^{13}$C NMR (126 MHz, cdcl$_3$) δ ppm 169.9*, 163.4*, 128.61, 123.87 (d, J=282.0 Hz), 123.82, 78.54 (q, J=31.3 Hz), 66.12, 61.52, 60.56, 36.20, 32.24. Note: this compound is a 3:1 mixture of amide bond rotamers. *Carbonyl chemical shifts estimated indirectly through $^1$H-$^{13}$C HMBC (heteronuclear multiple-bond correlation).

HRMS Calculated for C$_8$H$_{12}$F$_3$NO$_3$ [M+H]$^+$ 228.0848; found 228.0836.

1-(16) Synthesis of 1-(2-Fluorophenyl)-2-(1,1,1-trifluorobut-3-en-2-yloxy)ethanone

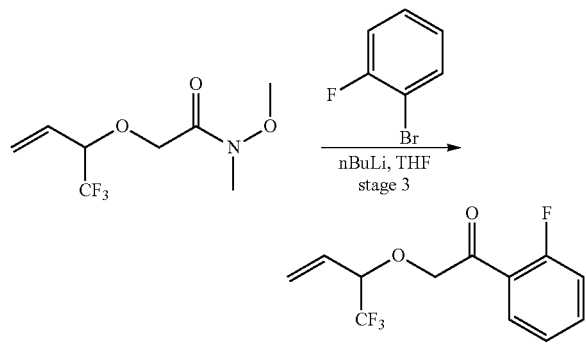

To a solution 1-bromo-2-fluorobenzene (0.967 kg, 5.527 mol) in THF (6.2 L) at −75° C., was added n-butyllithium (2.50 M in hexane, 2.09 L, 5.22 mol) while maintaining temperature below −65° C. (ca. 100 min.). After 15 mins, a solution of N-methoxy-N-methyl-2-(1,1,1-trifluorobut-3-en-2-yloxy)acetamide (0.949 kg, 4.178 mol) in THF (1.6 L) was added while maintaining temperature below −65° C. (ca. 70 min.). After 2.5 h at −78° C., the reaction was quenched by addition of sat. aq. NH$_4$Cl (3.0 L) and methyl tert-butyl ether (9.0 L). The reaction mixture was warmed to rt, the aq. phase was extracted again with methyl tert-butyl ether (2.5 L). The organic phases were combined, washed with sat. aq. NaCl (2×0.3 L) and concentrated under vacuum to afford the title compound as an oil (1.007 kg, 80.0%). $^1$H NMR (500 MHz, CDCl$_3$) δ ppm 7.96 (td, J=7.6, 1.8 Hz, 1H), 7.62-7.54 (m, 1H), 7.33-7.25 (m, 1H), 7.20-7.12 (m, 1H), 5.86 (ddd, J=17.5, 10.4, 7.3 Hz, 1H), 5.60 (dd, J=20.5, 13.8 Hz, 2H), 4.91-4.76 (m, 2H), 4.39 (dq, J=12.8, 6.4 Hz, 1H); $^{13}$C NMR (125 MHz, CDCl$_3$) δ ppm 193.55, 162.14 (d, J$_{CF}$=254.1 Hz), 135.36 (d, J$_{CF}$=9.2 Hz), 130.62 (d, J$_{CF}$=3.2 Hz), 128.49, 124.85 (d, J$_{CF}$=3.3 Hz), 123.89, 122.93, 122.72 (d, J$_{CF}$=24.5 Hz), 116.50 (d, J$_{CF}$=23.7 Hz), 78.97 (q, J$_{CF}$=31.4 Hz), 74.56 (d, J$_{CF}$=12.4 Hz).

HRMS Calculated for C$_{12}$H$_{10}$F$_4$O$_2$ [M+H]$^+$ 263.0695; found 263.0709.

1-(17) Synthesis of 1-(2-Fluorophenyl)-2-(1,1,1-trifluorobut-3-en-2-yloxy)ethanone oxime

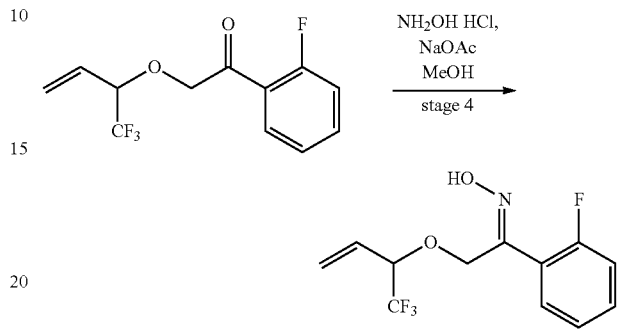

To a reactor was added hydroxylamine hydrochloride (0.34 kg, 4.95 mol), sodium acetate (0.47 kg, 5.70 mol) and MeOH (2.68 L). To this suspension was charged a solution of 1-(2-fluorophenyl)-2-(1,1,1-trifluorobut-3-en-2-yloxy)ethanone (0.998 kg, 3.806 mol) in MeOH (1.8 L) and the reaction mixture was heated to 40-50° C. Upon completion (ca. 2 h) the reaction mixture was cooled to rt, and filtered over Celite (0.5 wt) and rinsed with EtOAc (3.0 L). The filtrate was concentrated under vacuum and to the resulting residue was added methyl tert-butyl ether (6.3 L), water (0.94 L) and sat. aq. NaHCO$_3$ (2.5 L). The organic phase was washed once with water (1.6 L) and sat. aq. NaCl (0.1 L). The organic phase was concentrated under vacuum to afford the title compound as an oil (1.03 kg, 95.0%). $^1$H NMR (500 MHz, CDCl$_3$) δ ppm 7.49-7.35 (m, 2H), 7.24-7.06 (m, 2H), 5.78-5.65 (m, 1H), 5.54-5.40 (m, 2H), 4.89-4.81 (m, 1H), 4.53 (d, J=12.6 Hz, 1H), 4.47 (d, J=12.6 Hz, 0.5H), 4.27-4.18 (m, 1H), 4.13-4.05 (m, 0.5H).

HRMS Calculated for C$_{12}$H$_{11}$F$_4$NO$_2$ [M+H]$^+$ 278.0804; found 278.0780.

Note: 1-(2-Fluorophenyl)-2-(1,1,1-trifluorobut-3-en-2-yloxy)ethanone oxime exists as an equilibrium of structural isomers, which accounts for the less-than-whole-number integral values.

1-(18) Syntheis of (3aR*,4S*,6aS*)-6a-(2-fluorophenyl)-4-(trifluoromethyl)hexahydrofuro[3,4-c]isoxazole

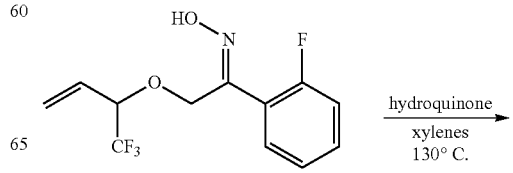

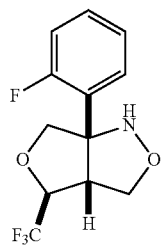

To a solution of 1-(2-fluorophenyl)-2-(1,1,1-trifluorobut-3-en-2-yloxy)ethanone oxime (1.085 kg, 3.328 mol) in xylenes (6.9 L) was added hydroquinone (86.2 g, 0.8 mol) at rt. The solution was heated to 128° C. (internal temperature) for 18 h. The solution was cooled to rt, and hexanes (7.0 L) was added, followed by 4.0 M aq. HCl (2.4 L). The reaction mixture was stirred for 1 h, and filtered. To the solid was added water (2.0 L), methyl tert-butyl ether (7.0 L) and 25% wt. aq. NaOH (0.4 L). The aq. layer was extracted once with methyl tert-butyl ether (7.0 L), the organics were combined, washed with 27% aq. NaCl (2.0 L) and concentrated under vacuum to a black oil (512.0 g, 56%). $^1$H NMR (500 MHz, CDCl$_3$) δ ppm 7.64-7.52 (m, 1H), 7.39-7.31 (m, 1H), 7.19 (td, J=7.7, 1.2 Hz, 1H), 7.11 (ddd, J=11.9, 8.2, 1.0 Hz, 1H), 4.54 (d, J=10.1 Hz, 1H), 4.34-4.23 (m, 1H), 4.26-4.17 (m, 1H), 4.16 (d, J=10.2 Hz, 1H), 4.10 (d, J=8.5 Hz, 1H), 3.71 (d, J=20.2 Hz, 1H); $^{13}$C NMR (125 MHz, CDCl$_3$) δ ppm 160.59 (d, J$_{CF}$=247.0 Hz), 130.50 (d, J$_{CF}$=8.7 Hz), 128.72, 124.69 (d, J$_{CF}$=3.3 Hz), 124.45 (q, J$_{CF}$=281.8 Hz), 124.43 (d, J$_{CF}$=11.9 Hz), 116.66 (d, J$_{CF}$=22.7 Hz), 83.70 (q, J$_{cF}$=32.1 Hz), 78.17 (d, J$_{CF}$=3.1 Hz), 77.63. 54.53.

HRMS Calculated for C$_{12}$H$_{11}$F$_4$NO$_2$ [M+H]$^+$ 278.0804; found 278.0802.

1-(19) Synthesis of) ((2S*,3R*,4S*)-4-amino-4-(2-fluorophenyl)-2-(trifluoromethyl)tetrahydrofuran-3-yl)methanol

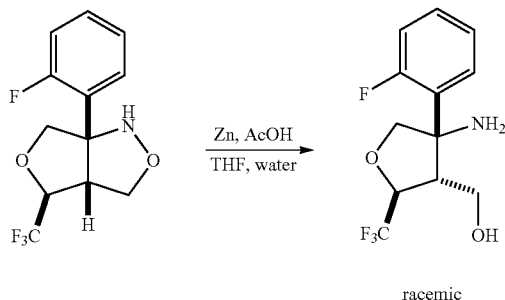

racemic

Zinc (389.2 g, 5.95 mol) was placed in a reaction vessel, and water was added (893 mL). Acetic acid (135 mL, 2.38 mol) was added while maintaining the temperature below 10° C. After 15 min, 6a-(2-fluorophenyl)-4-(trifluoromethyl) hexahydrofuro[3,4-c]isoxazole (550.0 g, 1.98 mol) was added as a solution in THF (665 mL). The reaction mixture was stirred over 16 h at rt. Methylene chloride (1.89 L) was added, followed by 28% aq. NH$_4$OH (552 mL) while the temperature was kept below 30° C. The mixture was stirred for 30 min, and then filtered over Celite (80 g) rinsing with methylene chloride (378 mL). The aq. layer was extracted with methylene chloride (1.89 L). The organics were combined, washed with sat. aq. NaCl (1.0 L) and concentrated under vacuum to afford an oil (502 g, 90.6%). The crude residue was used in the following step without additional purification.

HRMS Calculated for C$_{12}$H$_{13}$F$_4$NO$_2$ [M+H]$^+$ 280.0961; found 280.0972.

1-(20) Synthesis of ((2S,3R,4S)-4-Amino-4-(2-fluorophenyl)-2-(trifluoromethyl)tetrahydrofuran-3-yl) methanol (2S,3S)-2,3-bis(benzoyloxy)succinate

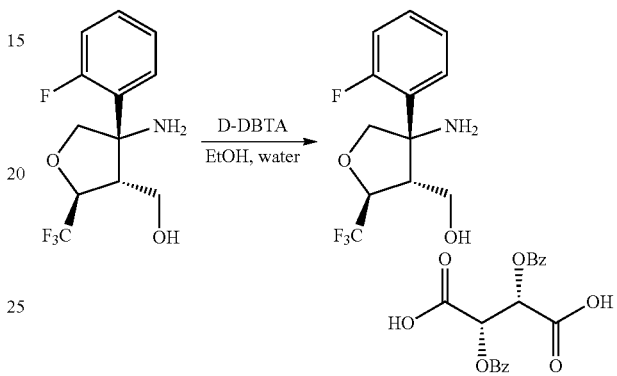

To a solution of 4-amino-4-(2-fluorophenyl)-2-(trifluoromethyl)tetrahydrofuran-3-yl)methanol (0.502 kg, 1.798 mol) in ethanol (4.865 L) was added dibenzoyl-D-tartaric acid (0.642 kg, 1.798 mol). The resulting suspension was heated to 67° C. Water (94.0 mL, 5.2 mol) was added over 15 min while maintaining temperature >66° C. The resulting solution was cooled to to 45° C. while precipitation occurred. The slurry was reheated to 60° C., and then cooled to ambient temperature at 5° C./hour. The slurry was filtered, and the solid was rinsed with premixed and cooled solution of ethanol (950 mL) and water (20 mL). The solid was dried until constant weight under vacuum (370 g, 97.6% ee). $^1$H NMR (500 MHz, CD$_3$OD) δ ppm 8.13 (d, J=7.2 Hz, 4H), 7.66-7.58 (m, 3H), 7.54-7.45 (m, 5H), 7.36-7.20 (m, 2H), 5.92 (s, 2H), 4.79-4.66 (m, 1H), 4.40-4.28 (m, 1H), 4.04 (dd, J=12.1, 3.4 Hz, 1H), 3.92 (dd, J=12.1, 5.4 Hz, 1H), 3.30-3.24 (m, 1H); $^{13}$C NMR (125 MHz, DMSO) δ ppm 169.61, 165.81, 160.23 (d, J=246.1 Hz), 133.00, 131.34 (d, J=9.1 Hz), 129.65, 129.55, 128.08, 127.97 (d, J=3.5 Hz), 124.95 (d, J=3.3 Hz), 116.56 (d, J=23.5 Hz), 77.48 (q, J$_{CF}$=31.0 Hz), 76.33, 73.20, 65.61 (d, J=3.1 Hz), 57.11.

HRMS Calculated for C$_{12}$H$_{13}$F$_4$NO$_2$ [M+H]$^+$ 280.0961; found 280.0967 (for amino alcohol).

The absolute stereochemistry of the title compound was assigned by comparison with a sample prepared starting from enantioenriched (S)-2-(trifluoromethyl)oxirane.

Chiral HPLC Parameters:
Equipment, Reagents, and Mobile Phase:

| Equipment: | |
| --- | --- |
| HPLC column: | Chiralcel OD, 4.6 × 250 mm, 10 µm, Daicel Chemical Industries, Ltd., catalog no. 14025. |
| Solvent Delivery System: | Agilent 1100 HPLC ternary pump, low pressure mixing with in-line degasser, or equivalent. |
| Autosampler: | Agilent 1100 autosampler, 0.1 to 100 µL range, or equivalent. |

-continued

| | |
|---|---|
| Detector: | Agilent 1100 variable wavelength detector or equivalent. |
| Chromatographic Software: | Agilent ChemStation software version A.09.03 or higher for HPLC, Waters Empower 2 Build 2154 or equivalent. |
| Volumetric Glassware: | Class A. |
| Volumetric pipette: | Class A. |
| Pipettor: | Calibrated Eppendorf adjustable volume, or equivalent. |
| Balance: | Analytical balance, capable of weighing ±0.1 mg. |
| Reagents: | |
| Heptane: | HPLC grade, Baker (catalog no. 9177-03) or equivalent. |
| 2-Propanol: | HPLC grade, Baker (catalog no. 9095-03) or equivalent. |
| Triethylamine: | ≥99%, Sigma-Aldrich (catalog no. T0886) or equivalent. |

Mobile Phase:

Add 70 mL 2-propanol and 930 mL heptane (measured separately with a 100 mL and 1000-mL graduated cylinders) and 1.0 mL triethylamine (measured with volumetric glass pipette) to an appropriate flask and mix. Degas in-line during use.

Diluting Solution: 2-Propanol

| HPLC Parameters: | |
|---|---|
| HPLC column: | Chiralcel OD, 4.6 × 250 mm, 10 μm, Daicel Chemical Industries, Ltd., catalog no. 14025. |
| Temperature: | 35° C. |
| Flow rate*: | 0.8 mL/min |
| Gradient: | NA |
| Injection Volume: | 5 μL |
| Detection: | 262 nm UV |
| Data acquisition time: | 30 min |
| Total run time: | 30 min |
| Column Maximum Pressure: | 35 Bar |
| Needle Wash: | 2-propanol |

*Flow rate may be adjusted ±0.2 ml/min to obtain specified retention times.

| Retention Times for Analytes and Impurities: | |
|---|---|
| Compound Peak | Retention Time (Relative Retention Time, RRT) |
| (structure) | 20.6 min ± 10% (RRT 1.00) |
| (structure, Enantiomer) | 19.2 min (RRT 0.93) |

A Typical Chromatogram from a Chiral HPLC Isolation of Compound 1-(20) is presented in FIG. 1.

1-(21) Synthesis of N-((3S,4R,5S)-3-(2-fluorophenyl)-4-(hydroxymethyl)-5-(trifluoromethyl)-tetrahydrofuran-3-ylcarbamothioyl)benzamide

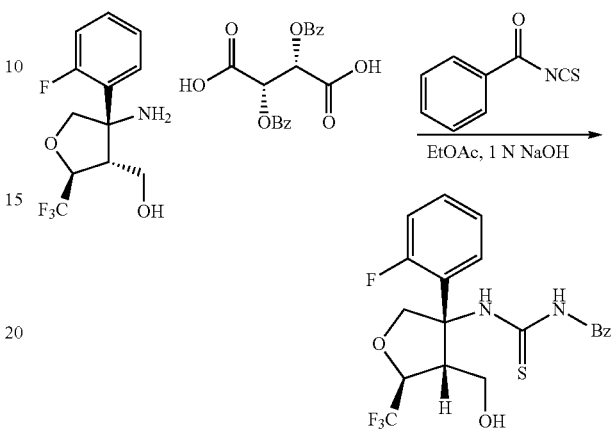

To chiral salt ((2S,3R,4S)-4-Amino-4-(2-fluorophenyl)-2-(trifluoromethyl)tetrahydrofuran-3-yl)methanol (2S,3S)-2,3-bis(benzoyloxy)succinate (0.361 kg, 0.556 mol) was added EtOAc (1.08 L) and the suspension was cooled to −3° C. 1.0 N aq. NaOH (1.30 L) was added over 20 mins while maintaining T<5° C. After 5 mins, benzoyl isothiocyanate (80.0 mL, 594 mmol) was added over 8 mins while maintaining T<5° C. After 1 h, EtOAc (722 mL) was charged. The aq. layer was removed, and the organics were washed with sat. aq. NaHCO$_3$ (361 mL) and sat. aq. NaCl (361 mL). The organics were filtered over celite (90 g) and rinsed with EtOAc (360 mL). The organics were concentrated under vacuum to afford a residue which was re-dissolved into CH$_2$Cl$_2$ (1.1 L) and concentrated to afford the title compound as yellow foam (261 g, 99% yield accounting for residual solvents) which was used in the following step. $^1$H NMR (500 MHz, DMSO) δ ppm 12.04 (s, 2H), 11.20 (s, 2H), 7.95 (d, J=7.4 Hz, 2H), 7.69-7.60 (m, 1H), 7.56-7.42 (m, 2H), 7.37-7.28 (m, 1H), 7.24-7.12 (m, 2H). 5.59 (t, J=4.5 Hz, 1H), 5.03 (d, J=9.7 Hz, 1H), 4.92 (d, J=9.7 Hz, 1H), 4.75-4.63 (m, 1H), 3.92-3.74 (m, 2H), 2.77-2.66 (m, 1H); $^{13}$C NMR (125 MHz, DMSO) δ ppm 179.98, 167.85, 159.75 (d, J$_{CF}$=245.0 Hz), 133.44, 132.58, 129.88, 129.81, 129.04, 128.85, 126.31 (d, J$_{CF}$=9.8 Hz), 124.36, 116.83 (d, J$_{CF}$=23.4 Hz), 76.11 (q, J$_{CF}$=31.0 Hz). 74.37 (d, J$_{CF}$=6.1 Hz), 68.77 (d, J$_{CF}$=3.4 Hz), 57.03, 52.23.

HRMS Calculated for C$_{20}$H$_{18}$F$_4$N$_2$O$_3$S [M+H]$^+$ 441.0896; found 441.0818.

1-(22) Synthesis of N-((4aS,5S,7aS)-7a-(2-fluorophenyl)-5-(trifluoromethyl)-4a,5,7,7a-tetrahydro-4H-furo[3,4-d][1,3]thiazin-2-yl)benzamide

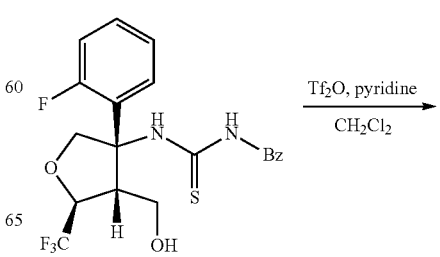

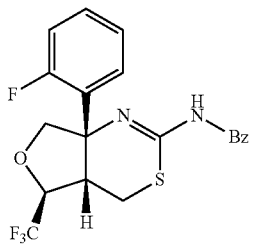

A solution of N-((3S,4R,5S)-3-(2-fluorophenyl)-4-(hydroxymethyl)-5-(trifluoromethyl)-tetrahydrofuran-3-ylcarbamothioyl)benzamide (258.3 g, 583.8 mmol) in CH₂Cl₂ (1.55 L) was cooled to −19.4° C. Pyridine (118 mL, 1.46 mol) was added while maintaining temperature at −20° C., and then the reaction mixture was cooled to −24° C. In another nitrogen purged vessel, CH₂Cl₂ (258 mL) was added followed by trifluoromethanesulfonic anhydride (108.0 mL, 642.2 mmol). The resulting solution was added to the reaction mixture over 30 min, while maintaining temperature<−19.7° C. Upon completed addition, the reaction mixture was stirred for 30 min at −20° C. to −15° C., and then warmed to −11° C. over 20 min. Saturated aq. NH₄Cl (646 mL) and water (390 mL) was added. The mixture was warmed to ambient temperature and the aq. layer was removed. The organics were washed with premixed saturated aq. NH₄Cl (646 mL) and water (390 mL). The aq. layers were combined, and extracted once with CH₂Cl₂ (520 mL). The organics were combined, and concentrated under vacuum to afford a light orange foam (250 g, 100%). The residue was used in the next stage without purification. ¹H NMR (500 MHz, CDCl₃) δ ppm 8.03 (d, J=6.7 Hz, 2H), 7.52 (t, J=7.0 Hz, 1H), 7.48-7.31 (m, 4H), 7.20 (t, J=7.4 Hz, 1H), 7.12 (dd, J=12.0, 8.4 Hz, 1H), 4.82-4.73 (m, 1H), 4.60 (d, J=8.9 Hz, 1H), 4.03 (d, J=8.3 Hz, 1H), 3.57 (d, J=2.7 Hz, 1H), 3.20 (d, J=13.6 Hz, 1H), 2.81 (dd, J=13.8, 2.5 Hz, 1H); ¹³C NMR (125 MHz, CDCl₃) δ ppm 171.50, 159.57 (d, J_CF=247.2 Hz), 134.62, 132.49, 130.65 (d, J_CF J=8.8 Hz), 129.77, 128.51, 128.45, 125.14 (q, J_CF=281.8 Hz), 124.97 (d, J_CF=3.0 Hz), 124.66 (d, J_CF=10.3 Hz), 117.05 (d, J_CF=23.5 Hz), 66.81 (d, J_CF=5.2 Hz), 38.90, 23.20.

HRMS Calculated for C₂₀H₁₆F₄N₂O₂S [M+H]⁺ 425.0947; found 425.0945.

1-(23) Synthesis of (4aS,5S,7aS)-7a-(2-fluorophenyl)-5-(trifluoromethyl)-4a,5,7,7a-tetrahydro-4H-furo[3,4-d][1,3]thiazin-2-amine

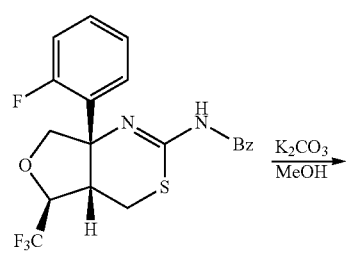

To a solution of N-((4aS,5S,7aS)-7a-(2-fluorophenyl)-5-(trifluoromethyl)-4a,5,7,7a-tetrahydro-4H-furo[3,4-d][1,3]thiazin-2-yl)benzamide (250.2 g, 589.5 mmol) in methanol (1.25 L) was added K₂CO₃ (81.5 g, 590.0 mmol). The suspension was heated to 65° C. for 6 h. Upon cooling to ambient temperature, the solvent was evaporated under vacuum. To the resulting residue, was added 1.0 N aq NaOH (1.18 L) and THF (502 mL). The heterogeneous mixture was heated to 45° C. for 1 h. The mixture was cooled to ambient temperature, and EtOAc (1.38 L) was added. The aqueous layer was extracted with EtOAc (0.75 L). The organics were combined, washed with saturated aq. NaHCO₃ (500 mL) and saturated aq. NaCl (500 mL). The organics were concentrated under vacuum to afford the title compound as a brown oil (184.1 g, 91.6% yield accounting for residual solvents). ¹H NMR (500 MHz, DMSO) δ ppm 7.49-7.42 (m, 1H), 7.40-7.33 (m, 1H), 7.26-7.15 (m, 2H), 6.26 (s, 2H), 4.77-4.54 (m, 1H), 4.40 (d, J=8.0 Hz, 1H). 3.80 (dd, J=7.9, 2.3 Hz, 1H), 3.24-3.17 (m, 1H), 3.00 (dd, J=13.9, 3.2 Hz, 1H), 2.85 (dd, J=13.9, 3.9 Hz, 1H); ¹³C NMR (125 MHz, DMSO) δ ppm 159.75 (d, J_CF=245.1 Hz), 149.51, 131.31 (d, J_CF=3.9 Hz), 130.13 (d, J_CF=8.8 Hz), 128.08 (d, J_CF=10.4 Hz), 128.28 (q, J_CF=282.1 Hz). 124.87 (d, J_CF=3.0 Hz), 116.80 (d, J=23.8 Hz). 78.77, 76.80 (q, J_CF=30.8 Hz), 66.31, 36.37, 23.27.

HRMS Calculated for C₁₃H₁₂F₄N₂OS [M+H]⁺ 321.0685; found 321.0677.

1-(24) Synthesis of (4aS,5S,7aS)-7a-(2-fluoro-5-nitrophenyl)-5-(trifluoromethyl)-4a,5,7,7a-tetrahydro-4H-furo[3,4-d][1,3]thiazin-2-amine hydrochloride

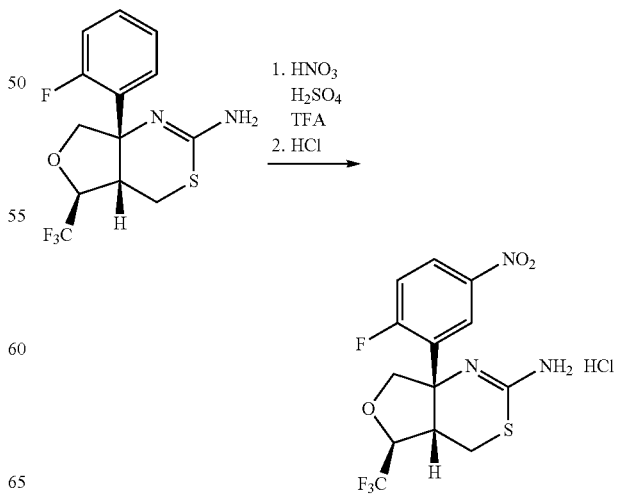

To a cooled vessel containing (4aS,5S,7aS)-7a-(2-fluorophenyl)-5-(trifluoromethyl)-4a,5,7,7a-tetrahydro-4H-furo[3,4-d][1,3]thiazin-2-amine (184.1 g, 574.8 mmol) was added trifluoroacetic acid (0.954 kg) in portions while the temperature was maintained below 20° C. The mixture was cooled to 3.5° C. and sulfuric acid (146 mL, 2.73 mol) was added over 20 min while the temperature was maintained below 5° C. Fuming nitric acid (39.8 mL, 0.948 mol) was added over 30 min, while the temperature was maintained below 10° C. After 1.5 h at 0-10° C., the reaction mixture was slowly quenched by transferring into an aq. solution of NaOH (575 g, 14.4 mol) in water (4.6 L) cooled to 5° C. The resulting suspension was stirred for 1 h at 21° C. The suspension was then filtered and the solid rinsed with cold water (920 mL). The solid was dried under vacuum until constant weight, and then dissolved into ethanol (1.05 L). The solution was heated to 35° C., and conc. HCl (55.6 mL, 0.690 mol) was added while maintaining temperature below 40° C. The suspension was then cooled to −5° C., held for 1 hr and filtered. The solid was rinsed with cold ethanol (420 mL) and dried until constant weight to obtain the title compound (185.0 g, 87.3%). $^1$H NMR (500 MHz, DMSO) δ ppm 11.80 (s, 2H), 8.45-8.36 (m, 1H), 8.31 (dd, J=6.6, 2.5 Hz, 1H), 7.66 (dd, J=11.1, 9.3Hz, 1H), 4.96-4.72 (m, 1H), 4.58 (d, J=10.0 Hz, 1H), 4.27 (d, J=9.9 Hz, 1H), 3.76-3.66 (m, 1H), 3.39 (dd, J=14.9, 3.6 Hz, 1H), 3.24 (dd, J=14.3, 4.6 Hz, 1H); $^{13}$C NMR (125 MHz, DMSO) δ ppm 168.34, 163.33 (d, $J_{CF}$=257.8 Hz), 144.58, 127.61 (d, $J_{CF}$=11.6 Hz), 125.84, 124.10, 119.28 (d, $J_{CF}$=26.5 Hz), 77.38 (q, $J_{CF}$=31.5 Hz), 75.99, 65.88 (d, $J_{CF}$=4.8 Hz), 40.36, 23.98.

HRMS Calculated for $C_{13}H_{11}F_4N_3O_3S$ [M+H]$^+$ 366.0536; found 366.0523.

1-(25) Synthesis of (4aS,5S,7aS)-7a-(5-amino-2-fluorophenyl)-5-(trifluoromethyl)-4a,5,7,7a-tetrahydro-4H-furo[3,4-d][1,3]thiazin-2-amine

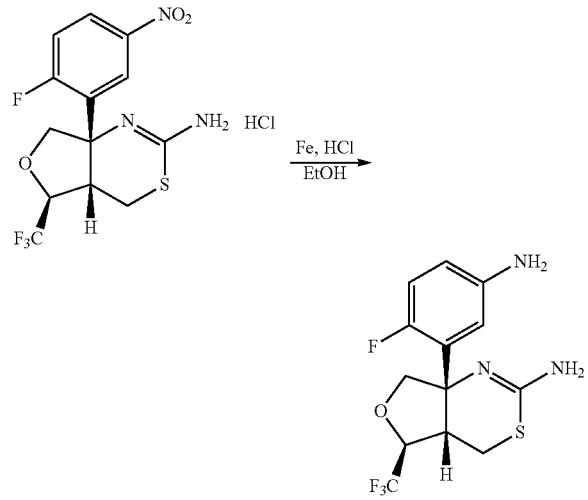 [SMILES: "EtOH" ; NC1=N[C@@]2(c3cc([N+](=O)[O-])ccc3F)CO[C@H](C(F)(F)F)[C@H]2CS1 ; Cl ; NC1=N[C@@]2(c3cc(N)ccc3F)CO[C@H](C(F)(F)F)[C@H]2CS1]

Ethanol (0.975 L) was added to iron powder (62.5 g, 1.12 mol) under nitrogen atmosphere. Concentrated HCl (9.03 mL) was added at ambient temperature and the suspension was heated to 65° C. for 1.5 h. The suspension was then cooled to 50° C., and sat. aq. NH$_4$Cl (299 g) were added. The temperature of the reaction mixture was allowed to reach 50° C., and (4aS,5S,7aS)-7a-(2-fluoro-5-nitrophenyl)-5-(trifluoromethyl)-4a,5,7,7a-tetrahydro-4H-furo[3,4-d][1,3]thiazin-2-amine hydrochloride (75.0 g, 187.0 mol) was added in portions while maintaining temperature below 68° C. After 30 min, ethanol (0.45 L) was added, and the reaction mixture was cooled to 20-25° C. over 1 h. The suspension was stirred for 2 h and filtered over Celite (75 g) rinsing with ethanol (0.972 L). The solution was concentrated under vacuum to a brown solid. Water (0.9 L) was added followed by 3.0 N NaOH (0.187 L, 560 mmol) while maintaining temperature below 35° C. The resulting suspension was stirred for 1 h at 20-25° C. The suspension was filtered, and the solid was rinsed with cold water (0.38 L). The solid was dried under vacuum at 40-45° C. over 24 h to obtain the title compound (57.7 g, 95.5%). $^1$H NMR (500 MHz, DMSO) δ ppm 6.81 (dd, J=12.5, 8.6 Hz, 1H), 6.62 (dd, J=7.0, 2.9 Hz, 1H), 6.50-6.42 (m, 1H), 6.16 (s, 2H), 4.96 (s, 2H), 4.72-4.54 (m, 1H), 4.35 (d, J=7.8 Hz, 1H), 3.74 (dd, J=7.8, 2.5 Hz, 1H), 3.18-3.08 (m, 1H), 3.01 (dd, J=13.9, 3.0 Hz, 1H). 2.84 (dd, J=13.8, 3.8 Hz, 1H); $^{13}$C NMR (125 MHz, DMSO) δ ppm 156.20 (d, $J_{CF}$=243.0 Hz), 148.73, 145.49, 127.86 (d, $J_{CF}$=11.0 Hz), 116.79 (d, $J_{CF}$=24.8 Hz), 116.10 (d, $T_{CF}$=3.3 Hz), 114.10 (d, $J_{CF}$=8.0 Hz), 78.89, 76.57 (q, $J_{CF}$=31.0 Hz), 66.35, 36.35, 23.11.

HRMS Calculated for $C_{13}H_{13}F_4N_3OS$ [M+H]$^+$ 336.0794; found 336.0789.

The title compound was subjected to an Ames test (*Salmonella typhimurium* tester strains TA98, TA100, TA1535 and TA1537 and *Escherichia coli* tester strain WP2 uv. *Mutation Research* 1975, 31, 347; *Mutation Research* 1976, 38, 3; *Proc. Nat. Acad. Sci. USA* 1976, 73, 950; *Proc. Nat. Acad. Sci. USA* 1975, 72, 5135) in the absence and presence of rat liver S9. The compound was negative up to the highest dose/concentration tested (5000 ug/plate).

1-(26) Synthesis of N-(3-((4aS,5S,7aS)-2-amino-5-(trifluoromethyl)-4a,5,7,7a-tetrahydro-4H-furo[3,4-d][1,3]thiazin-7a-yl)-4-fluorophenyl)-5-methoxypyrazine-2-carboxamide

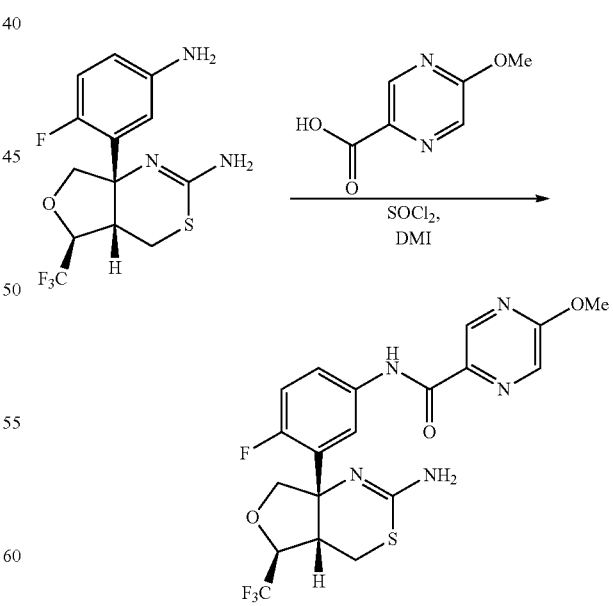

A suspension of 5-methoxypyrazine-2-carboxylic acid (26.29 g, 0.17 mol) in N,N'-dimethylimidazoline-2-one (160 mL) was stirred at ambient temperature for 15 min, then cooled to 2.2° C. Thionyl chloride (14.7 mL, 0.202 mol) was added while maintaining temperature under 5° C. The resulting suspension was stirred at 0-10° C. for 2 h while it transitioned to a clear solution. In another vessel, (4aS,5S,7aS)-7a-(5-amino-2-fluorophenyl)-5-(trifluoromethyl)-4a,5,7,7a-tetrahydro-4H-furo[3,4-d][1,3]thiazin-2-amine (52.0 g, 0.155 mol) was dissolved into N,N'-dimethylimidazoline-2-one (160 mL). The resulting solution was added to the solution of acyl chloride while maintaining temperature below 10° C. The reaction mixture was stirred for 30 min. Water (780 mL) was charged while maintaining temperature below 30° C. The resulution mixture was stirred for 30 min, and then EtOAc (780 mL) was added. To this mixture was added, 50% aq. NaOH (84.8 g) until the pH of the aqueous layer reached 11. The aq. layer was extracted with EtOAc (260 mL). The organics were combined, washed with sat. aq. NaCl (260 mL) and water (260 mL). The organics were filtered over Celite pad (26 g) and rinsed with EtOAc (260 mL). The organics were concentrated under vacuum to afford a solid. To the solid was added 1-propanol (728 mL), and the suspension was heated to 75° C. until a clear solution formed. The solution was cooled to −10° C. and held for 1 h. The solid was filtered, rinsed with cold 1-propanol (104 mL) and dried under vacuum (35° C.) until constant weight to afford the title compound (62.1 g, 84.9%). $^1$H NMR (500 MHz, DMSO) δ ppm 10.56 (s, 2H), 8.88 (d, J=1.2 Hz, 1H), 8.39 (d, J=1.2 Hz, 1H), 7.95-7.83 (m, 2H), 7.18 (dd, J=12.0, 8.8 Hz, 1H), 6.25 (s, 2H), 4.76-4.60 (m, 1H), 4.36 (d, J=8.1 Hz, 1H), 4.01 (s, 3H), 3.88 (dd, J=7.9, 2.3 Hz, 1H), 3.23-3.11 (m, 2H), 2.91 (dd, J=13.8, 3.6 Hz, 1H); $^{13}$C NMR (125 MHz, DMSO) δ ppm 162.11, 161.93, 156.13 (d, $J_{CF}$=242.9 Hz), 149.38, 142.01, 138.35, 135.09, 133.98, 128.53 (d, $J_{CF}$=11.6 Hz), 126.06 (q, $J_{CF}$=282.0 Hz), 123.32, 121.93 (d, $J_{CF}$=8.6 Hz), 116.76 (d, $J_{CF}$=25.1 Hz), 78.86 (d, $J_{CF}$=6.9 Hz), 76.94 (q, $J_{CF}$=30.5 Hz), 66.37, 54.75, 36.44, 23.53.

HRMS Calculated for $C_{19}H_{17}F_4N_5O_3S$ [M+H]$^+$ 472.1066; found 472.1052.

Specific optical rotation $[\alpha]_D$+110.5 (c 0.519, MeOH)

Specific Optical Rotation Parameters:

| Equipment: | |
|---|---|
| Polarimeter: | Perkin Elmer, model 341 or equivalent. |
| Cell: | Microglass cell, 100 mm pathlength, 1.0 mL capacity, Perkin-Elmer Cat. #B001-7047. |
| Balance: | Calibrated analytical balance capable of weighing ±0.1 mg |
| Water Bath: | NESLAB RTE 1121 Chiller or equivalent. |
| Volumetric glassware: | Class A. |
| Quartz Standard | ID number 098799, or equivalent. |
| Polarimeter: | Perkin Elmer, model 341 or equivalent. |
| Reagents: | |
| Methanol: | HPLC grade, Baker (catalog no. 9093-03) or eqivalent |
| Instrument parameters: | |
| Lamp: | Na/Hal, Perkin-Elmer Cat. #B000-8754. |
| Cell: | Microcell (100 mm), Perkin-Elmer Cat. #B004-1693. |
| Cell Path: | 100 mm (1 decimeter) |
| Mode: | OROT |
| Wavelength: | 589 nm |
| Cell Temperature: | 20° C. |
| Integration time: | 2 seconds |
| Aperture: | MICRO |
| Water bath temperature: | 20 ± 1° C. |

Alternative Preparation of N-(3-((4aS,5S,7aS)-2-amino-5-(trifluoromethyl)-4a,5,7,7a-tetrahydro-4H-furo[3,4-d][1,3]thiazin-7a-yl)-4-fluorophenyl)-5-(fluoromethyl)pyrazine-2-carboxamide (Example 8)

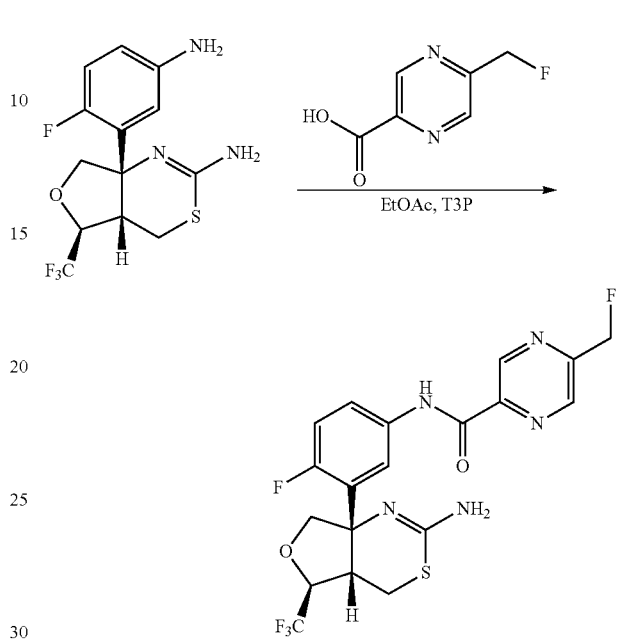

5-(Fluoromethyl)pyrazine-2-carboxylic acid (32.6 g, 1.05 equiv) and (4aS,5S,7aS)-7a-(5-amino-2-fluorophenyl)-5-(trifluoromethyl)-4a,5,7,7a-tetrahydro-4H-furo[3,4-d][1,3]thiazin-2-amine (70.0 g, 1.0 equiv)[1] were charged to a reactor and ethyl acetate (EtOAc, 630 mL) was added to the mixture to give a suspension. A solution of n-propane phosphonic acid anhydride (T3P, 146 g, 1.10 equiv, 50 wt % in EtOAc) was added at ambient temperature while controlling the internal temperature below 30° C. The reaction mixture was stirred at 40-45° C.>3 hours and monitored by HPLC. The reaction mixture was cooled to 15-20° C. and water (140 mL) was charged. After 10-15 minutes charged 28% ammonium hydroxide (175 mL) while controlling the temperature below 30° C. EtOAc (245 mL0 was added and the reaction mixture was stirred for 30 minutes at ambient temperature. The aqueous phase was separated and back-extracted with EtOAc (490 mL). The organic phases were combined and washed with 15% aq. NaCl (140 mL) and water (140 mL). The organic layer was filtered over Celite (1.0 Wt) and rinsed with EtOAc (140 mL). The solution was concentrated under vacuum to obtain a beige solid (quantitative crude yield) which was recrystallized from 1-propanol to afford N-(3-((4aS,5S,7aS)-2-amino-5-(trifluoromethyl)-4a,5,7,7a-tetrahydro-4H-furo[3,4-d][1,3]thiazin-7a-yl)-4-fluorophenyl)-5-(fluoromethyl)pyrazine-2-carboxamide as a white solid (70.0 g). $^1$H NMR (500 MHz, DMSO) δ 10.89 (s, 1H), 9.30 (s, 1H), 8.89 (s, 1H), 7.95 (dd, J=7.3, 2.7 Hz, 1H), 7.94-7.89 (m, 1H), 7.21 (dd, J=12.0, 8.8 Hz, 1H), 6.22 (s, 2H), 5.71 (d, J=46.3 Hz, 2H), 4.77-4.61 (m, 1H), 4.37 (d, J=8.1 Hz, 1H), 3.87 (dd, J=8.0, 2.7 Hz, 1H), 3.20 (dt, J=7.0, 3.5 Hz, 1H), 3.15 (dd, J=13.9, 3.1 Hz, 1H), 2.91 (dd, J=13.8, 3.8 Hz, 1H). $^{13}$C NMR (126 MHz, DMSO) δ161.32 (s), 155.82 (d, J=243.4 Hz), 153.71 (d, J=18.7 Hz), 148.77 (s), 144.71 (d, J=1.9 Hz), 143.30 (s), 141.01 (d, J=5.6 Hz), 134.36 (d, J=2.0 Hz), 128.20 (d, J=12.1 Hz), 125.57 (q, J=283.0 Hz), 123.12 (d, J=3.6 Hz), 121.64 (d, J=8.6 Hz), 116.35 (d, J=25.2 Hz), 82.55 (d, J=165.8 Hz), 78.37 (s), 76.44 (q, J=30.6 Hz), 65.89 (d, J=5.3 Hz), 35.89 (s), 23.01 (s).

HRMS Calculated for $C_{19}H_{17}F_5N_5O_2S$ [M+H]$^+$ 474.1023; found 474.1032.

Specific Optical Rotation: $[\alpha]_D^{20}$=+102.4

[1] A preparation of (4aS,5S,7aS)-7a-(5-amino-2-fluorophenyl)-5-(trifluoromethyl)-4a,5,7,7a-tetrahydro-4H-furo[3,4-d][1,3]thiazin-2-amine is described herein above in step 1-(25) in the alternative preparation of N-(3-((4aS,5S,7aS)-2-amino-5-(trifluoromethyl)-4a,5,7,7a-tetrahydro-4H-furo[3,4-d][1,3]thiazin-7a-yl)-4-fluorophenyl)-5-methoxypyrazine-2-carboxamide (Example 1).

In Vitro Cellular Assay:
Quantification of Aβ Peptide in Culture of Neurons from Rat Fetus Brain (1) Rat Primary Neuronal Culture Primary neuronal cultures were prepared from the cerebral cortex of embryonic day 18 Wistar rats (Charles River, UK). Specifically, the embryos were aseptically removed from pregnant rats under ether anesthesia. The brain was isolated from the embryo and immersed in HBSS (Sigma Aldrich #H9269) containing 10 mM HEPES (Gibco #15630-056). The cerebral cortex was collected from the isolated brain under a stereoscopic microscope. The cerebral cortex fragments collected were enzymatically treated in an enzyme solution containing 0.05% trypsin-EDTA solution (GIBCO, #25300) at 37° C. for 20 minutes to disperse the cells. The cells were then washed twice and then gently resuspended in Neurobasal medium (Gibco #21103) supplemented with 2% B27 supplement (GIBCO #17504-044), 0.5 mM L-glutamine (GIBCO #25030), 1×N2 (GIBCO #17502-048), 100 ug/ml Pen/Strep (GIBCO 15140-122) and 5% heat inactivated FCS (PAA #A15-701). The cell dispersion was filtered through a 40-μm nylon mesh (BD Falcon #352340) to remove the remaining cell mass, and thus a neuronal cell suspension was obtained. The neuronal cell suspension was diluted with the medium above and then plated in a volume of 100 μL/well at an initial cell density of 3.25×10$^5$ cells/ml in poly-D-lysine coated 96-well culture plate (Greiner #655940). The plated cells were cultured in the culture plate at 37° C. in 5% $CO_2$-95% air for 24 hrs. The total amount of the medium was replaced with 'assay Neurobasal medium' (as above excluding heat inactivated FCS), and then the cells were cultured for a further five days.

(2) Addition of Compound

The drug was added to the culture plate on Day 6 of culture as follows. 8 point compound serial dilutions were generated in DMSO at a concentration of ×1000 that of the final assay concentration (FAC). Compound solutions were then prepared by adding 999 ul of 'Assay Neurobasal media' (as described in above section) to 1 ul of DMSO compound stock. The total amount of the medium was removed from each of the cell plate wells, and 140 μL/well of 'Assay Neurobasal media' was added followed by 60 ul of compound solution. The final DMSO concentration was 0.1%.

(3) Sampling

The cells were cultured for either 1 or 3 days after addition of the compound for ABx-40 and ABx-42 assays respectively. 150 μl of sample medium was collected and used as the ELISA sample.

(4) Evaluation of Cell Survival

Cell survival was evaluated using an Alamar assay according to the following procedure. After collecting the sample to be used in the ELISA assay, 50 μl of 20% Alamar blue solution (Invitrogen #DAL1100) in assay Neurobasal media, was added to 50 μl of remaining sample within each well. Cells were then incubated at 37° C. in 5% $CO_2$-95% air for 1 hr.

Measurement of fluorescence intensity for each well was the carried out at 540/590 nm using a Pherastar plus plate reader (BMG labtech). Upon measurement, wells having no cells plated and containing only the medium and Alamar solution were set as background (bkg).

(5) Aβ ELISA

Human/Rat β Amyloid (42) ELISA Kit Wako (#290-62601) and Human/Rat β Amyloid (40) ELISA Kit Wako (#294-62501) from Wako Pure Chemical Industries, Ltd. were used for Aβ ELISA. Aβ ELISA was carried out according to the protocols recommended by the manufacturers, described in the documents accompanying the kits. The results were shown as percentage of the control groups and $IC_{50}$ values for each compound were determined using four parameter logistic fit model using the XLFITS software package (IDBS).

The compounds of the present invention have an Aβ42 production reducing effect.

The compound of the general formula (I) or pharmaceutically acceptable salt thereof according to the present invention has an Aβ42 production reducing effect. Thus, the present invention can particularly provide a prophylactic or therapeutic agent for a neurodegenerative disease caused by Aβ such as Alzheimer-type dementia or Down's syndrome.

As measured by the above in vitro assay, compound Examples 1 to 18 showed $IC_{50}$ values of less than 0.1 μM as shown in Table 5:

TABLE 5

| Example | $IC_{50}$ (uM) |
|---|---|
| 1 | 0.008 |
| 2 | 0.004 |
| 3 | 0.004 |
| 4 | 0.008 |
| 5 | 0.012 |
| 6 | 0.006 |
| 7 | 0.008 |
| 8 | 0.006 |
| 9 | 0.007 |
| 10 | 0.010 |
| 11 | 0.010 |
| 12 | 0.006 |
| 13 | 0.044 |
| 14 | 0.002 |
| 15 | 0.007 |
| 16 | 0.009 |
| 17 | 0.051 |
| 18 | 0.015 |

The invention claimed is:

1. A compound which is N-(3-((4aS,5S,7aS)-2-amino-5-(trifluoromethyl)-4a,5,7,7a-tetrahydro-4H-furo[3,4-d][1,3]thiazin-7a-yl)-4-fluorophenyl)-5-methoxypyrazine-2-carboxamide, or a pharmaceutically acceptable salt thereof.

2. A pharmaceutical composition comprising the compound according to claim 1, or a pharmaceutically acceptable salt thereof, as an active ingredient in association with a pharmaceutically acceptable carrier.

3. A method of treating Down's syndrome, comprising administering to a human subject suffering from Down's syndrome an effective amount of the compound according to claim 1, or a pharmaceutically acceptable salt thereof.

4. A method of treating Alzheimer-type dementia, comprising administering to a human subject suffering from Alzheimer-type dementia an effective amount of the compound according to claim 1, or a pharmaceutically acceptable salt thereof.

* * * * *